US006635473B1

(12) United States Patent
Foster et al.

(10) Patent No.: US 6,635,473 B1
(45) Date of Patent: Oct. 21, 2003

(54) POLYPEPTIDES AND POLYNUCLEOTIDES FROM COAGULASE-NEGATIVE STAPHYLOCOCCI

(75) Inventors: Timothy J. Foster, Dublin (IE); Kirk McCrea, Houston, TX (US); Magnus A. O. Hook, Houston, TX (US); Stacy Davis, Houston, TX (US); Deirdre Ni Eidhin, Dublin (IE); Orla Hartford, Meath (IE)

(73) Assignees: The Provost Fellows and Scholars of the College of the Holy and Undivided Trinity of Queen Elizabeth Near Dublin, Dublin (IE); The Texas A&M University System, College Station, TX (US)

( * ) Notice: Subject to any disclaimer, the term of this patent is extended or adjusted under 35 U.S.C. 154(b) by 0 days.

(21) Appl. No.: 09/386,962

(22) Filed: Aug. 31, 1999

Related U.S. Application Data

(60) Provisional application No. 60/117,119, filed on Jan. 25, 1999, and provisional application No. 60/098,443, filed on Aug. 31, 1998.

(51) Int. Cl.$^7$ ........................ C07H 21/04; C12N 15/11; C12N 15/63; C12N 1/20

(52) U.S. Cl. .................. 435/320.1; 536/23.1; 536/23.4; 536/23.2; 536/24.3; 536/24.32; 435/325; 435/252.3

(58) Field of Search .............................. 536/23.1, 23.4, 536/23.2, 24.3, 24.32; 435/320.1, 325, 252.3

(56) References Cited

U.S. PATENT DOCUMENTS 5,055,455 A 10/1991 Pier

FOREIGN PATENT DOCUMENTS

WO WO 97/48727 12/1997
WO WO 00/12131 3/2000

OTHER PUBLICATIONS

McCrea et al., "The serine–aspartate repeat (Sdr) protein family in *Staphylococcus epidermidis*", Microbiology (2000), 146, pp. 1535–1546.

Cockayne et al., "Molecular Cloning of a 32–Kilodalton Lipoprotein Component of a Novel Iron–Regulated *Staphylococcus epidermidis*", Infection and Immunity, Aug. 1998, pp. 3767–3774.

McDevitt et al., "Molecular characterization of the clumping factor (fibrinogen receptor) of *Staphylococcus aureus*", Molecular Microbiology (1994), 11(2), pp. 237–248.

McCrea et al., "A Family of Putative Adherence Proteins Related to the Clumping Factor of *Staphyloccus aureus*", Abstracts of the General Meeting of the American Society for Microbiology, American Society of Microbiology, vol. 98, May 17, 1998, pp. 63–AbstrB47.

Nilsson et al.—"Afibrinogen–binding proteing of Staphylococcus epidermidis"; Infect. Immun. vol. 66, No. 6, pp. 2666–2673, especially abstract.

Database EMBL, Jun. 5, 1998, retrieved from EBI, Database accession no. y17116, XP002235437.

Database EMBL, Jun. 22, 1998, retrieved from EBI, Database accession no. AAV04279, XP002235438.

Database EMBL, Aug. 3, 1998, Foster, "Staphylococcus aureus strain Newman clumping Factor B(clfB) gene", retrieved from EMBL, Database accession no. AJ224764, XP002205878.

*Primary Examiner*—Sean McGarry
(74) *Attorney, Agent, or Firm*—Larson & Taylor PLC

(57) ABSTRACT

Isolated proteins, designated SdrF, SdrG and SdrH, and their corresponding amino acid and nucleic acid sequences are provided which are useful in the prevention and treatment of infection caused by coagulase-negative staphylococcal bacteria such as *S. epidermidis*. The SdrF, SdrG and SdrH proteins are cell-wall associated proteins that specifically bind host proteins and which each have a highly conserved motif of which the consensus sequence is TYTFTDYVD (SEQ ID NO:16). The proteins, antigenic portions thereof and anti-SdrF, SdrG and SdrH antibodies are also useful for the identification and diagnosis of coagulase-negative staphylococcal infections. In particular, the proteins are advantageous because they may be used as vaccine components or antibodies thereof, and they may be administered to wounds or used to coat biomaterials to act as blocking agents to prevent or inhibit the binding of coagulase-negative staphylococci to wounds or biomaterials.

10 Claims, 28 Drawing Sheets

S.EPIDERMIDIS STRAIN K28 SdrG

CODING SEQUENCE FOR SdrF - INCLUDES FLANKING SEQUENCES

```
tattggataaattatgcttataaagtatttacataaaaatgtaaatgcaatttacaagta
 Y  W  I  N  Y  A  Y  K  V  F  T  -  K  C  K  C  N  L  Q  V
aatattcaaattatttccttgtaaaatatttattttaactggaggtatagtatgaaaaag
 N  I  Q  I  I  S  L  -  N  I  Y  F  N  W  R  Y  S  M  K  K
agaagacaaggaccaattaacaagagagtggattttctatccaacaaggtaaacaagtac
 R  R  Q  G  P  I  N  K  R  V  D  F  L  S  N  K  V  N  K  Y
tcgattaggaagttcacagtaggtacagcttcaatactcgtgggtgctacgttaatgttt
 S  I  R  K  F  T  V  G  T  A  S  I  L  V  G  A  T  L  M  F
ggtgccgcagacaatgaggctaaagcggctgaagacaatcaattagaatcagcttcaaaa
 G  A  A  D  N  E  A  K  A  A  E  D  N  Q  L  E  S  A  S  K
gaagaacagaaaggtagtcgtgataatgaaaactcaaaacttaatcaagtcgatttagac
 E  E  Q  K  G  S  R  D  N  E  N  S  K  L  N  Q  V  D  L  D
aacggatcacatagttctgagaaaacaacaaatgtaaacaatgcaactgaagtaaaaaaa
 N  G  S  H  S  S  E  K  T  T  N  V  N  N  A  T  E  V  K  K
gttgaagcaccaacgacaagtgacgtatctaagcctaaagctaatgaagcagtagtgacg
 V  E  A  P  T  T  S  D  V  S  K  P  K  A  N  E  A  V  V  T
aatgagtcaactaaaccaaaaacaacagaagcaccaactgttaatgaggaatcaatagct
 N  E  S  T  K  P  K  T  T  E  A  P  T  V  N  E  E  S  I  A
```

FIG. 2

```
gaaacacccaaaacctcaactacacaacaagattcgactgagaagaataatccatcttta
 E  T  P  K  T  S  T  T  Q  Q  D  S  T  E  K  N  N  P  S  L
aaagataatttaaattcatcctcaacgacatctaaagaaagtaaaacagacgaacattct
 K  D  N  L  N  S  S  S  T  T  S  K  E  S  K  T  D  E  H  S
actaagcaagctcaaatgtctactaataaatcaaatttagacacaaatgactctccaact
 T  K  Q  A  Q  M  S  T  N  K  S  N  L  D  T  N  D  S  P  T
caaagtgagaaaacttcatcacaagcaaataacgacagtacagataatcagtcagcacct
 Q  S  E  K  T  S  S  Q  A  N  N  D  S  T  D  N  Q  S  A  P
tctaaacaattagattcaaaaccatcagaacaaaaagtatataaaacaaaatttaatgat
 S  K  Q  L  D  S  K  P  S  E  Q  K  V  Y  K  T  K  F  N  D
gaacctactcaagatgttgaacacacgacaactaaattaaaaacaccttctgtttcaaca
 E  P  T  Q  D  V  E  H  T  T  T  K  L  K  T  P  S  V  S  T
gatagttcagtcaatgataagcaagattacacacgaagtgctgtagctagtttaggtgtt
 D  S  S  V  N  D  K  Q  D  Y  T  R  S  A  V  A  S  L  G  V
gattctaatgaaacagaagcaattacaaatgcagttagagacaatttagatttaaaagct
 D  S  N  E  T  E  A  I  T  N  A  V  R  D  N  L  D  L  K  A
gcatctagagaacaaatcaatgaagcaatcattgctgaagcactaaaaaaagacttttct
 A  S  R  E  Q  I  N  E  A  I  I  A  E  A  L  K  K  D  F  S
aaccctgattatggtgtcgatacgccattagctctaaacagatctcaatcaaaaaattca
 N  P  D  Y  G  V  D  T  P  L  A  L  N  R  S  Q  S  K  N  S
```

FIG. 2(cont'd)

```
ccacataagagtgcaagtccacgcatgaatttaatgagtttagctgctgagcctaatagt
 P  H  K  S  A  S  P  R  M  N  L  M  S  L  A  A  E  P  N  S
ggtaaaaatgtgaatgataaagttaaaatcacaaaccctacgctttcacttaataagagt
 G  K  N  V  N  D  K  V  K  I  T  N  P  T  L  S  L  N  K  S
aataatcacgctaataacgtaatatggccaacaagtaacgaacaatttaatttaaaagca
 N  N  H  A  N  N  V  I  W  P  T  S  N  E  Q  F  N  L  K  A
aattatgaattagatgacagcataaaagagggagatacttttactattaagtatggtcag
 N  Y  E  L  D  D  S  I  K  E  G  D  T  F  T  I  K  Y  G  Q
tatattagaccgggtggtttagaacttcctgcaataaaaactcaactacgtagtaaggat
 Y  I  R  P  G  G  L  E  L  P  A  I  K  T  Q  L  R  S  K  D
ggctctattgtagctaatggtgtatatgataaaactacaaatacgacgacttatacattt
 G  S  I  V  A  N  G  V  Y  D  K  T  T  N  T  T  T  Y  T  F
```

FIG. 2(cont'd)

```
actaactatgttgatcaatatcaaaatattacaggtagttttgatttaattgcgacgcct
 T  N  Y  V  D  Q  Y  Q  N  I  T  G  S  F  D  L  I  A  T  P
aagagggaaacagcaattaaggataatcagaattatcctatggaagtgacgattgctaac
 K  R  E  T  A  I  K  D  N  Q  N  Y  P  M  E  V  T  I  A  N
gaagtagtcaaaaaagacttcattgtggattatggtaataaaaaggacaatacaactaca
 E  V  V  K  K  D  F  I  V  D  Y  G  N  K  K  D  N  T  T  T
gcagcggtagcaaatgtggataatgtaaataataaacataacgaagttgtttatctaaac
 A  A  V  A  N  V  D  N  V  N  N  K  H  N  E  V  V  Y  L  N
caaaataaccaaaaccctaaatatgctaaatatttctcaacagtaaaaaatggtgaattt
 Q  N  N  Q  N  P  K  Y  A  K  Y  F  S  T  V  K  N  G  E  F
ataccaggtgaagtgaaagtttacgaagtgacggataccaatgcgatggtagatagcttc
 I  P  G  E  V  K  V  Y  E  V  T  D  T  N  A  M  V  D  S  F
aatcctgatttaaatagttctaatgtaaaagatgtgacaagtcaatttgcacctaaagta
 N  P  D  L  N  S  S  N  V  K  D  V  T  S  Q  F  A  P  K  V
agtgcagatggtactagagttgatatcaattttgctagaagtatggcaaatggtaaaaag
 S  A  D  G  T  R  V  D  I  N  F  A  R  S  M  A  N  G  K  K
tatattgtaactcaagcagtgagaccaacgggaactggaaatgtttataccgaatattgg
 Y  I  V  T  Q  A  V  R  P  T  G  T  G  N  V  Y  T  E  Y  W
ttaacaagagatggtactaccaatacaaatgatttttaccgtggaacgaagtctacaacg
 L  T  R  D  G  T  T  N  T  N  D  F  Y  R  G  T  K  S  T  T
```

FIG. 2(cont'd)

```
gtgacttatctcaatggttcttcaacagcacagggggataatcctacatatagtctaggt
 V  T  Y  L  N  G  S  S  T  A  Q  G  D  N  P  T  Y  S  L  G
gactatgtatggttagataaaaataaaaacggtgttcaagatgatgatgagaaaggttta
 D  Y  V  W  L  D  K  N  K  N  G  V  Q  D  D  D  E  K  G  L
gcaggtgtttatgttactcttaaagacagtaacaatagagaattacaacgtgtaactact
 A  G  V  Y  V  T  L  K  D  S  N  N  R  E  L  Q  R  V  T  T
gatcaatctggacattatcaatttgataatttacaaaatggaacgtacacagtcgagttt
 D  Q  S  G  H  Y  Q  F  D  N  L  Q  N  G  T  Y  T  V  E  F
gcgattcctgataattatacgccatctcccgcaaataattctacaaatgatgcaatagat
 A  I  P  D  N  Y  T  P  S  P  A  N  N  S  T  N  D  A  I  D
tcagatggtgaacgtgatggtacacgtaaagtagttgttgccaaaggaacaattaataat
 S  D  G  E  R  D  G  T  R  K  V  V  V  A  K  G  T  I  N  N
gctgataatatgactgtagatactggctttatttaactcctaaatacaatgtcggagat
 A  D  N  M  T  V  D  T  G  F  Y  L  T  P  K  Y  N  V  G  D
tatgtatgggaagatacaaataaagatggtatccaagatgacaatgaaaaaggaatttct
 Y  V  W  E  D  T  N  K  D  G  I  Q  D  D  N  E  K  G  I  S
ggtgttaaagtaacgttaaaaaataaaaatggagatactattggcacaacgacaacagat
 G  V  K  V  T  L  K  N  K  N  G  D  T  I  G  T  T  T  T  D
tcaaatggtaaatatgaattcacaggtttagagaacggggattacacaatagaatttgag
 S  N  G  K  Y  E  F  T  G  L  E  N  G  D  Y  T  I  E  F  E
```

FIG. 2(cont'd)

```
acgccggaaggctacacaccgactaaacaaaactcgggaagtgacgaaggtaaagattca
 T  P  E  G  Y  T  P  T  K  Q  N  S  G  S  D  E  G  K  D  S
aacggtacgaaaacaacagtcacagtcaaagatgcagataataaaacaatagactcaggt
 N  G  T  K  T  T  V  T  V  K  D  A  D  N  K  T  I  D  S  G
ttctacaagccaacatataacttaggtgactatgtatgggaagatacaaataaagatggt
 F  Y  K  P  T  Y  N  L  G  D  Y  V  W  E  D  T  N  K  D  G
attcaagacgacagtgaaaaagggatttctggggttaaagtgacgttaaaagataaaaat
 I  Q  D  D  S  E  K  G  I  S  G  V  K  V  T  L  K  D  K  N
ggaaatgccattgggacaacgacaacagacgcaagtggtcattatcaatttaaaggatta
 G  N  A  I  G  T  T  T  T  D  A  S  G  H  Y  Q  F  K  G  L
gaaaatggaagctacacagttgagtttgagacaccatcaggttatacaccgacaaaagcg
 E  N  G  S  Y  T  V  E  F  E  T  P  S  G  Y  T  P  T  K  A
```

FIG. 2(cont'd)

```
aattcaggtcaagatataactgtagattccaacggtataacaacaacaggtatcattaac
 N  S  G  Q  D  I  T  V  D  S  N  G  I  T  T  T  G  I  I  N
ggagctgataatctcacaattgatagtggtttctacaaaacaccaaaatatagtgtcgga
 G  A  D  N  L  T  I  D  S  G  F  Y  K  T  P  K  Y  S  V  G
gattatgtatgggaagatacaaataaagatggtatccaagatgacaatgaaaagggaatt
 D  Y  V  W  E  D  T  N  K  D  G  I  Q  D  D  N  E  K  G  I
tctggtgttaaagtaacgttaaaggatgaaaagggaaatataattagcactacaacaact
 S  G  V  K  V  T  L  K  D  E  K  G  N  I  I  S  T  T  T  T
gatgaaaatggaaagtatcaatttgataatttagatagtggtaattacattattcatttt
 D  E  N  G  K  Y  Q  F  D  N  L  D  S  G  N  Y  I  I  H  F
gagaaaccggaaggcatgactcaaactacagcaaattctggaaatgatgatgaaaaagat
 E  K  P  E  G  M  T  Q  T  T  A  N  S  G  N  D  D  E  K  D
gctgatggggaagatgttcgtgttacgattactgatcatgatgactttagtatagataat
 A  D  G  E  D  V  R  V  T  I  T  D  H  D  D  F  S  I  D  N
ggttattttgacgatgattcagacagtgactcagacgcagatagtgattcagactcagac
 G  Y  F  D  D  D  S  D  S  D  S  D  A  D  S  D  S  D  S  D
agtgactcggacgcagacagcgattctgacgcagacagtgactcagacgcagatagtgat
 S  D  S  D  A  D  S  D  S  D  A  D  S  D  S  D  A  D  S  D
tctgactcagacagcgactcagacgcagatagtgattccgattcagacagcgactcggat
 S  D  S  D  S  D  S  D  A  D  S  D  S  D  S  D  S  D  S  D
```

FIG. 2(cont'd)

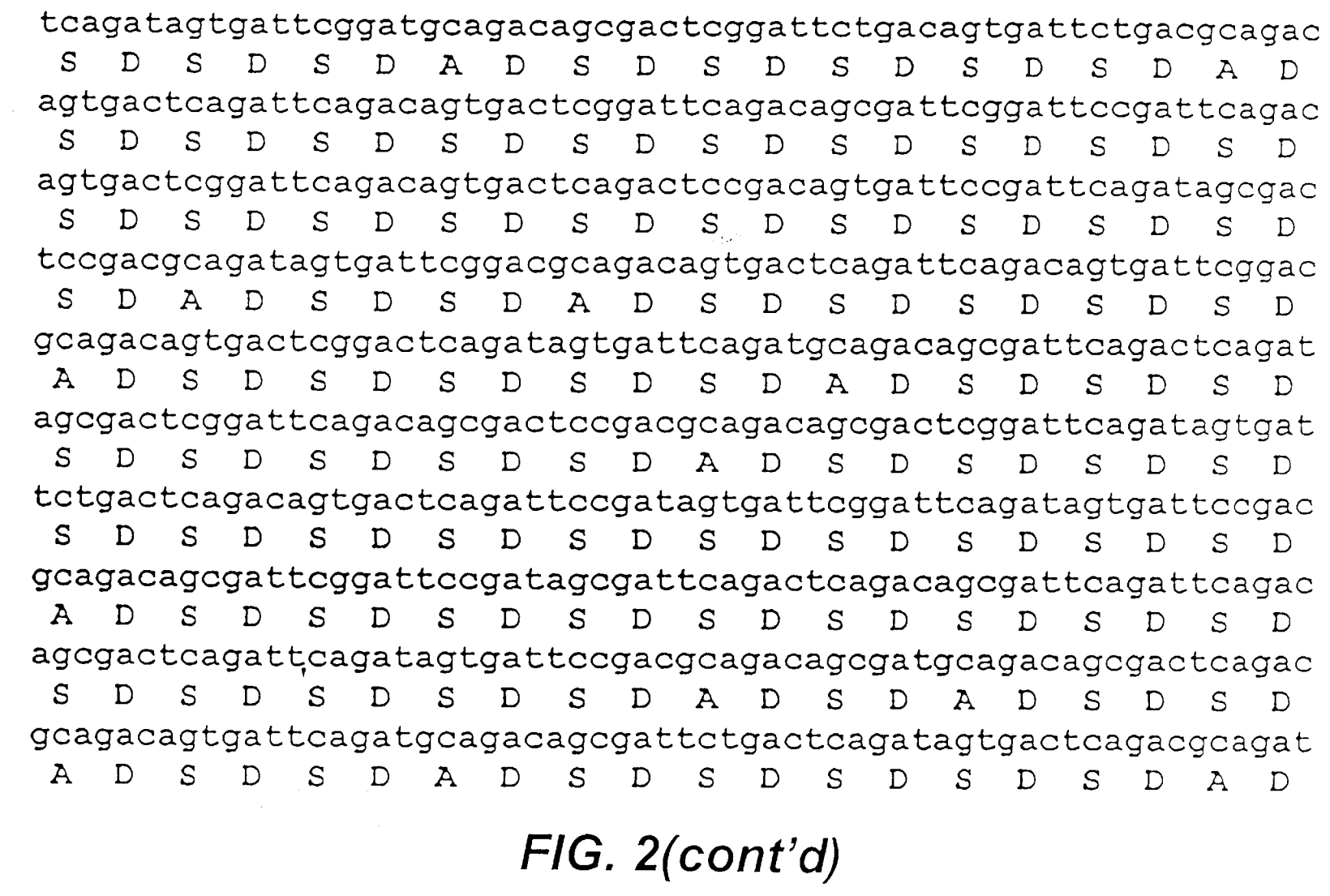

```
tcagatagtgattcggatgcagacagcgactcggattctgacagtgattctgacgcagac
 S  D  S  D  S  D  A  D  S  D  S  D  S  D  S  D  S  D  A  D
agtgactcagattcagacagtgactcggattcagacagcgattcggattccgattcagac
 S  D  S  D  S  D  S  D  S  D  S  D  S  D  S  D  S  D  S  D
agtgactcggattcagacagtgactcagactccgacagtgattccgattcagatagcgac
 S  D  S  D  S  D  S  D  S  D  S  D  S  D  S  D  S  D  S  D
tccgacgcagatagtgattcggacgcagacagtgactcagattcagacagtgattcggac
 S  D  A  D  S  D  S  D  A  D  S  D  S  D  S  D  S  D  S  D
gcagacagtgactcggactcagatagtgattcagatgcagacagcgattcagactcagat
 A  D  S  D  S  D  S  D  S  D  S  D  A  D  S  D  S  D  S  D
agcgactcggattcagacagcgactccgacgcagacagcgactcggattcagatagtgat
 S  D  S  D  S  D  S  D  S  D  A  D  S  D  S  D  S  D  S  D
tctgactcagacagtgactcagattccgatagtgattcggattcagatagtgattccgac
 S  D  S  D  S  D  S  D  S  D  S  D  S  D  S  D  S  D  S  D
gcagacagcgattcggattccgatagcgattcagactcagacagcgattcagattcagac
 A  D  S  D  S  D  S  D  S  D  S  D  S  D  S  D  S  D  S  D
agcgactcagattcagatagtgattccgacgcagacagcgatgcagacagcgactcagac
 S  D  S  D  S  D  S  D  S  D  A  D  S  D  A  D  S  D  S  D
gcagacagtgattcagatgcagacagcgattctgactcagatagtgactcagacgcagat
 A  D  S  D  S  D  A  D  S  D  S  D  S  D  S  D  S  D  A  D
```

FIG. 2(cont'd)

```
agtgattccgattccgatagcgattcagattctgatagtgactcagactcagacagtgac
 S  D  S  D  S  D  S  D  S  D  S  D  S  D  S  D  S  D  S  D
tcagattccgatagcgactcggattcagatagtgattccgacgcagacagtgactcagac
 S  D  S  D  S  D  S  D  S  D  S  D  S  D  A  D  S  D  S  D
tcagatagtgactcggattccgatagtgattccgacgcagacagcgattctgactcagat
 S  D  S  D  S  D  S  D  S  D  S  D  A  D  S  D  S  D  S  D
agtgactcagacgcagatagtgattccgattccgatagcgattcggatgcagacagcgac
 S  D  S  D  A  D  S  D  S  D  S  D  S  D  S  D  A  D  S  D
tcggattcagatagtgattccgacgcagacagtgactcagactcagatagtgactcggat
 S  D  S  D  S  D  S  D  A  D  S  D  S  D  S  D  S  D  S  D
tccgatagtgattccgacgcagacagcgattcggattccgatagcgattcagactccgac
 S  D  S  D  S  D  A  D  S  D  S  D  S  D  S  D  S  D  S  D
```

FIG. 2(cont'd)

```
agcgattcagattcagacagcgactcagattccgatagtgattccgattcagacagtgac
 S  D  S  D  S  D  S  D  S  D  S  D  S  D  S  D  S  D  S  D
tcggattccgatagtgactcagactcagacagtgactcagattcagatagcgactcagat
 S  D  S  D  S  D  S  D  S  D  S  D  S  D  S  D  S  D  S  D
tcagacagtgattcggactcagatagtgactccgattcagacagtgattcggattccgat
 S  D  S  D  S  D  S  D  S  D  S  D  S  D  S  D  S  D  S  D
agcgattcggattccgatagtgactcggattcagacagtgattcggactcagacagcgac
 S  D  S  D  S  D  S  D  S  D  S  D  S  D  S  D  S  D  S  D
tccgattcagatagtgattccgactcagacagcgattcggattccgatagtgactcggat
 S  D  S  D  S  D  S  D  S  D  S  D  S  D  S  D  S  D  S  D
tcagacagtgattcggactcagacagcgactccgattcagatagtgattccgacgcagac
 S  D  S  D  S  D  S  D  S  D  S  D  S  D  S  D  S  D  A  D
agcgactccgattcagatagtgattcggacgcagacagcgattccgatagtgactcggat
 S  D  S  D  S  D  S  D  S  D  A  D  S  D  S  D  S  D  S  D
tcagacagtgattcggactcagacagcgattccgattcagacagtgactcggactcagat
 S  D  S  D  S  D  S  D  S  D  S  D  S  D  S  D  S  D  S  D
agcgactcggattcagacagtgactcggactcagatagtgactccgattcagacagcgac
 S  D  S  D  S  D  S  D  S  D  S  D  S  D  S  D  S  D  S  D
tcggattctgataaaaatgcaaaagataaattacctgatacaggagcaaatgaagatcat
 S  D  S  D  K  N  A  K  D  K  L  P  D  T  G  A  N  E  D  H
```

*FIG. 2(cont'd)*

```
gattctaaaggcacattacttggaactttatttgcaggtttaggagcattattattagga
 D  S  K  G  T  L  L  G  T  L  F  A  G  L  G  A  L  L  L  G
agacgtcgtaaaaaagataataaagaaaaatagcactattgattcattcataagttattt
 R  R  R  K  K  D  N  K  E  K  *  H  Y  -  F  I  H  K  L  F
caagccaggtctatatggcctggtttgaaatcatattaaattgaaaggagaaaaagatga
 Q  A  R  S  I  W  P  G  L  K  S  Y  -  I  E  R  R  K  R  -
gtatgg
 V  W
```

FIG. 2(cont'd)

SdrG coding and flanking sequences.

```
atattgcaaaaagacttatatactatattgtattttactctagaaacgattttacttgaa
  I  A  K  K  T  Y  I  L  Y  C  I  L  L  -  K  R  F  L  L  E
aattacattgaaatagtcaaagataaggagttttatgattaaaaaaaataatttacta
 N  Y  I  E  I  V  K  D  K  E  F  L  -  L  K  K  N  N  L  L
actaaaaagaaacctatagcaaataaatccaataaatatgcaattagaaaattcacagta
 T  K  K  K  P  I  A  N  K  S  N  K  Y  A  I  R  K  F  T  V
ggtacagcgtctattgtaataggtgcagcattattgtttggtttaggtcataatgaggcc
 G  T  A  S  I  V  I  G  A  A  L  L  F  G  L  G  H  N  E  A
aaagctgaggagaatacagtacaagacgttaaagattcgaatatggatgatgaattatca
 K  A  E  E  N  T  V  Q  D  V  K  D  S  N  M  D  D  E  L  S
gatagcaatgatcagtccagtaatgaagaaaagaatgatgtaatcaataatagtcagtca
 D  S  N  D  Q  S  S  N  E  E  K  N  D  V  I  N  N  S  Q  S
ataaacaccgatgatgataaccaaataaaaaaagaagaaacgaatagcaacgatgccata
 I  N  T  D  D  D  N  Q  I  K  K  E  E  T  N  S  N  D  A  I
gaaaatcgctctaaagatataacacagtcaacaacaaatgtagatgaaaacgaagcaaca
 E  N  R  S  K  D  I  T  Q  S  T  T  N  V  D  E  N  E  A  T
tttttacaaaagaccctcaagataatactcagcttaaagaagaagtggtaaaagaaccc
 F  L  Q  K  T  P  Q  D  N  T  Q  L  K  E  E  V  V  K  E  P
tcatcagtcgaatcctcaaattcatcaatggatactgcccaacaaccatctcatacaaca
 S  S  V  E  S  S  N  S  S  M  D  T  A  Q  Q  P  S  H  T  T
```

*FIG. 3*

```
ataaatagtgaagcatctattcaaacaagtgataatgaagaaaattcccgcgtatcagat
 I  N  S  E  A  S  I  Q  T  S  D  N  E  E  N  S  R  V  S  D
tttgctaactctaaaataatagagagtaacactgaatccaataaagaagagaatactata
 F  A  N  S  K  I  I  E  S  N  T  E  S  N  K  E  E  N  T  I
gagcaacctaacaaagtaagagaagattcaataacaagtcaaccgtctagctataaaaat
 E  Q  P  N  K  V  R  E  D  S  I  T  S  Q  P  S  S  Y  K  N
atagatgaaaaaatttcaaatcaagatgagttattaaatttaccaataaatgaatatgaa
 I  D  E  K  I  S  N  Q  D  E  L  L  N  L  P  I  N  E  Y  E
aataaggttagaccgttatctacaacatctgcccaaccatcgagtaagcgtgtaaccgta
 N  K  V  R  P  L  S  T  T  S  A  Q  P  S  S  K  R  V  T  V
aatcaattagcggcagaacaaggttcgaatgttaatcatttaattaaagttactgatcaa
 N  Q  L  A  A  E  Q  G  S  N  V  N  H  L  I  K  V  T  D  Q
agtattactgaaggatatgatgatagtgatggtattattaaagcacatgatgctgaaaac
 S  I  T  E  G  Y  D  D  S  D  G  I  I  K  A  H  D  A  E  N
ttaatctatgatgtaacttttgaagtagatgataaggtgaaatctggtgatacgatgaca
 L  I  Y  D  V  T  F  E  V  D  D  K  V  K  S  G  D  T  M  T
gtgaatatagataaaaatacagttccatcagatttaaccgatagttttgcaataccaaaa
 V  N  I  D  K  N  T  V  P  S  D  L  T  D  S  F  A  I  P  K
ataaaagataattctggagaaatcatcgctacaggtacttatgacaacacaaataaacaa
 I  K  D  N  S  G  E  I  I  A  T  G  T  Y  D  N  T  N  K  Q
```

FIG. 3(cont'd)

```
attacctacacttttacagattatgtagataaatatgaaaatattaaagcgcaccttaaa
 I  T  Y  T  F  T  D  Y  V  D  K  Y  E  N  I  K  A  H  L  K
ttaacatcatacattgataaatcaaaggttccaaataataacactaagttagatgtagaa
 L  T  S  Y  I  D  K  S  K  V  P  N  N  N  T  K  L  D  V  E
tataagacggccctttcatcagtaaataaaacaattacggttgaatatcaaaaacctaac
 Y  K  T  A  L  S  S  V  N  K  T  I  T  V  E  Y  Q  K  P  N
gaaaatcggactgctaaccttcaaagtatgttcacaaacatagatacgaaaaaccataca
 E  N  R  T  A  N  L  Q  S  M  F  T  N  I  D  T  K  N  H  T
gttgagcaaacgatttatattaaccctcttcgttattcagccaaagaaacaaatgtaaat
 V  E  Q  T  I  Y  I  N  P  L  R  Y  S  A  K  E  T  N  V  N
atttcagggaatggcgatgaaggttcaacaattatcgacgatagtacaatcattaaagtt
```

*FIG. 3(cont'd)*

```
 I   S   G   N   G   D   E   G   S   T   I   I   D   D   S   T   I   I   K   V
tataaggttggagataatcaaaatttaccagatagtaacagaatttatgattacagtgaa
 Y   K   V   G   D   N   Q   N   L   P   D   S   N   R   I   Y   D   Y   S   E
tatgaagatgtcacaaatgatgattatgcccaattaggaaataataatgacgtgaatatt
 Y   E   D   V   T   N   D   D   Y   A   Q   L   G   N   N   N   D   V   N   I
aattttggtaatatagattcaccatatattattaaagttattagtaaatatgaccctaat
 N   F   G   N   I   D   S   P   Y   I   I   K   V   I   S   K   Y   D   P   N
aaggacgattacacgacgatacagcaaactgtgacaatgcaaacgactataaatgagtat
 K   D   D   Y   T   T   I   Q   Q   T   V   T   M   Q   T   T   I   N   E   Y
actggtgagtttagaacagcatcctatgataatacaattgctttctctacaagttcaggt
 T   G   E   F   R   T   A   S   Y   D   N   T   I   A   F   S   T   S   S   G
caaggacaaggtgacttgcctcctgaaaaaacttataaaatcggagattacgtatgggaa
 Q   G   Q   G   D   L   P   P   E   K   T   Y   K   I   G   D   Y   V   W   E
gatgtagataaagatggtattcaaaatacaaatgataatgaaaaaccgcttagtaatgta
 D   V   D   K   D   G   I   Q   N   T   N   D   N   E   K   P   L   S   N   V
ttggtaactttgacgtatcctgatggaacttcaaaatcagtcagaacagatgaagagggg
 L   V   T   L   T   Y   P   D   G   T   S   K   S   V   R   T   D   E   E   G
aaatatcaatttgatgggttaaaaaacggattgacttataaaattacattcgaaacaccg
 K   Y   Q   F   D   G   L   K   N   G   L   T   Y   K   I   T   F   E   T   P
gaaggatatacgccgacgcttaaacattcaggaacaaatcctgcactagactcagaaggc
 E   G   Y   T   P   T   L   K   H   S   G   T   N   P   A   L   D   S   E   G
```

*FIG. 3(cont'd)*

```
aattctgtatgggtaactattaacggacaagacgatatgactattgatagcggattttat
 N  S  V  W  V  T  I  N  G  Q  D  D  M  T  I  D  S  G  F  Y
caaacacctaaatatagcttagggaactatgtatggtatgacactaataaagatggtatt
 Q  T  P  K  Y  S  L  G  N  Y  V  W  Y  D  T  N  K  D  G  I
caaggtgatgatgaaaaaggaatctctggagtaaaagtgacgttaaaagatgaaaacgga
 Q  G  D  D  E  K  G  I  S  G  V  K  V  T  L  K  D  E  N  G
aatatcattagtacaacaacaactgatgaaaatggaaagtatcaatttgataatttaaat
 N  I  I  S  T  T  T  T  D  E  N  G  K  Y  Q  F  D  N  L  N
agtggtaattatattgttcattttgataaaccttcaggtatgactcaaacaacaacagat
 S  G  N  Y  I  V  H  F  D  K  P  S  G  M  T  Q  T  T  T  D
tctggtgatgatgacgaacaggatgctgatggggaagaagtccatgtaacaattactgat
 S  G  D  D  D  E  Q  D  A  D  G  E  E  V  H  V  T  I  T  D
catgatgactttagtatagataacggatactatgatgacgactcagattcagatagtgat
 H  D  D  F  S  I  D  N  G  Y  Y  D  D  D  S  D  S  D  S  D
tcagactcagatagcgacgactcagactccgatagcgattccgactcagacagcgactca
 S  D  S  D  S  D  D  S  D  S  D  S  D  S  D  S  D  S  D  S
gattccgatagtgattcagattcagacagtgactcagactcagatagtgattcagattca
 D  S  D  S  D  S  D  S  D  S  D  S  D  S  D  S  D  S  D  S
gacagcgattccgactcagacagtgactcaggattagacaatagctcagataagaataca
 D  S  D  S  D  S  D  S  D  S  G  L  D  N  S  S  D  K  N  T
```

FIG. 3(cont'd)

```
aaagataaattaccggatacaggagctaatgaagatcatgattctaaaggcacattactt
 K  D  K  L  P  D  T  G  A  N  E  D  H  D  S  K  G  T  L  L
ggagctttatttgcaggtttaggagcgttattattagggaagcgtcgcaaaaatagaaaa
 G  A  L  F  A  G  L  G  A  L  L  L  G  K  R  R  K  N  R  K
aataaaaattaaattattcaaatgaaattagtgaaagaagcagatacgacatttgaatag
 N  K  N  *  I  I  Q  M  K  L  V  K  E  A  D  T  T  F  E  -
aaagtatatttagtccaacaaatataaggtgttg
 K  V  Y  L  V  Q  Q  I  -  G  V
```

FIG. 3(cont'd)

SdrH coding region

```
atgaaaaagtttaacattaaacattcatttatgcttacgggctttgctttcatggtaact
 M  K  K  F  N  I  K  H  S  F  M  L  T  G  F  A  F  M  V  T
acatcattattcagtcaccaagcacatgctgaaggtaatcatcctattgacattaatttt
 T  S  L  F  S  H  Q  A  H  A  E  G  N  H  P  I  D  I  N  F
tctaaagatcaaattgatagaaatacagctaagagcaatattatcaatcgagtgaatgac
 S  K  D  Q  I  D  R  N  T  A  K  S  N  I  I  N  R  V  N  D
actagtcgcacaggaattagtatgaattcggataatgatttagatacagatatcgtttca
 T  S  R  T  G  I  S  M  N  S  D  N  D  L  D  T  D  I  V  S
aatagtgactcagaaaatgacacatatttagatagtgattcagattcagacagtgactca
 N  S  D  S  E  N  D  T  Y  L  D  S  D  S  D  S  D  S  D  S
gattcagatagtgactcagattcagatagtgactcagattcagatagtgactcagattca
 D  S  D  S  D  S  D  S  D  S  D  S  D  S  D  S  D  S  D  S
gacagtgattcagactcagatagtgactcagattcagacagtgattcagactcagatagt
 D  S  D  S  D  S  D  S  D  S  D  S  D  S  D  S  D  S  D  S
gattcagattcagacagtgattcagattcagacagtgactcagactcagacagtgattca
 D  S  D  S  D  S  D  S  D  S  D  S  D  S  D  S  D  S  D  S
gattcagatagtgattcagattcagatagtgattcagattcagatagtgattcagattca
 D  S  D  S  D  S  D  S  D  S  D  S  D  S  D  S  D  S  D  S
gacagtgactcagactcagacagtgattcagattcagatagtgattcagactcagatagt
 D  S  D  S  D  S  D  S  D  S  D  S  D  S  D  S  D  S  D  S
```

*FIG. 4*

```
gactcagattcagatagtgattcagactctggtacaagttcaggtaagggttcacatacc
 D  S  D  S  D  S  D  S  D  S  G  T  S  S  G  K  G  S  H  T
ggaaaaaaacctggtaaccctaaaggaaatacaaatagaccttctcaaagacatacgaat
 G  K  K  P  G  N  P  K  G  N  T  N  R  P  S  Q  R  H  T  N
caaccccaaaggcctaaatacaatcaaacaaatcaaaacaatataaacaatataaaccat
 Q  P  Q  R  P  K  Y  N  Q  T  N  Q  N  N  I  N  N  I  N  H
aatattaatcatacacgtactagtggagatggtgcgcctttaaacgtcaacaaaatatt
 N  I  N  H  T  R  T  S  G  D  G  A  P  F  K  R  Q  Q  N  I
attaattctaattcaggtcatagaaatcaaaataatataaatcaatttatatggaacaaa
 I  N  S  N  S  G  H  R  N  Q  N  N  I  N  Q  F  I  W  N  K
aatggctttttaaatctcaaaataataccgaacatagaatgaatagtagcgataatacc
 N  G  F  F  K  S  Q  N  N  T  E  H  R  M  N  S  S  D  N  T
aattcattaattagcagattcagacaattagccacgggtgcttataagtacaatccgttt
 N  S  L  I  S  R  F  R  Q  L  A  T  G  A  Y  K  Y  N  P  F
ttgattaatcaagtaaaaaatttgaatcaattagatggaaaggtgacagatagtgacatt
 L  I  N  Q  V  K  N  L  N  Q  L  D  G  K  V  T  D  S  D  I
tatagcttgtttagaaagcaatcatttagaggaaatgaatatttaaattcattacaaaaa
 Y  S  L  F  R  K  Q  S  F  R  G  N  E  Y  L  N  S  L  Q  K
gggacaagctatttcagatttcaatattttaatccacttaattctagtaaatactatgaa
 G  T  S  Y  F  R  F  Q  Y  F  N  P  L  N  S  S  K  Y  Y  E
```

FIG. 4(cont'd)

```
aatttagatgatcaggttttagctttaattacaggagaaatcggctcaatgccagaactt
 N  L  D  D  Q  V  L  A  L  I  T  G  E  I  G  S  M  P  E  L
aaaaaacctacggataaagaagataaaaatcatagcgccttcaaaaaccatagtgcagat
 K  K  P  T  D  K  E  D  K  N  H  S  A  F  K  N  H  S  A  D
gagataacaacaaataatgatggacactccaaagattatgataagaaaaagaaaatacat
 E  I  T  T  N  N  D  G  H  S  K  D  Y  D  K  K  K  K  I  H
cgaagtcttttatcgttaagtattgcaataattggaatttttctaggagtcactggacta
 R  S  L  L  S  L  S  I  A  I  I  G  I  F  L  G  V  T  G  L
tatatctttagaagaaaaaagtaa
 Y  I  F  R  R  K  K  *
```

FIG. 4(cont'd)

C
SdrF SDSDSDSDSDSDSDKNAKDKLPDTGANEDHDSKGTLLGTLFAGLGALLLGRRRKKDNKEK
SdrG SDSDSDSGLDNSSDKNTKDKLPDTGANEDHDSKGTLLGALFAGLGALLLGKRRKNRKNKN
SdrH DKNHSAFKNHSADEITTNNDGHSKDYDKKKKIHRSLLSLSIAIIGIFLGVTGLYIFRRKK

SEQUENCE LISTING

```
<160> NUMBER OF SEQ ID NOS: 38

<210> SEQ ID NO 1
<211> LENGTH: 5406
<212> TYPE: DNA
<213> ORGANISM: Staphylococcus epidermidis
<220> FEATURE:
<221> NAME/KEY: CDS
<222> LOCATION: (1)..(5406)

<400> SEQUENCE: 1

tat tgg ata aat tat gct tat aaa gta ttt aca taa aaa tgt aaa tgc       48
Tyr Trp Ile Asn Tyr Ala Tyr Lys Val Phe Thr     Lys Cys Lys Cys
1               5                   10                  15

aat tta caa gta aat att caa att att tcc ttg taa aat att tat ttt       96
Asn Leu Gln Val Asn Ile Gln Ile Ile Ser Leu     Asn Ile Tyr Phe
                20                  25                  30

aac tgg agg tat agt atg aaa aag aga aga caa gga cca att aac aag      144
Asn Trp Arg Tyr Ser Met Lys Lys Arg Arg Gln Gly Pro Ile Asn Lys
                35                  40                  45

aga gtg gat ttt cta tcc aac aag gta aac aag tac tcg att agg aag      192
Arg Val Asp Phe Leu Ser Asn Lys Val Asn Lys Tyr Ser Ile Arg Lys
        50                  55                  60

ttc aca gta ggt aca gct tca ata ctc gtg ggt gct acg tta atg ttt      240
Phe Thr Val Gly Thr Ala Ser Ile Leu Val Gly Ala Thr Leu Met Phe
    65                  70                  75

ggt gcc gca gac aat gag gct aaa gcg gct gaa gac aat caa tta gaa      288
```

-continued

```
Gly Ala Ala Asp Asn Glu Ala Lys Ala Ala Glu Asp Asn Gln Leu Glu
    80                  85                  90

tca gct tca aaa gaa gaa cag aaa ggt agt cgt gat aat gaa aac tca      336
Ser Ala Ser Lys Glu Glu Gln Lys Gly Ser Arg Asp Asn Glu Asn Ser
95                  100                 105                 110

aaa ctt aat caa gtc gat tta gac aac gga tca cat agt tct gag aaa      384
Lys Leu Asn Gln Val Asp Leu Asp Asn Gly Ser His Ser Ser Glu Lys
                115                 120                 125

aca aca aat gta aac aat gca act gaa gta aaa aaa gtt gaa gca cca      432
Thr Thr Asn Val Asn Asn Ala Thr Glu Val Lys Lys Val Glu Ala Pro
            130                 135                 140

acg aca agt gac gta tct aag cct aaa gct aat gaa gca gta gtg acg      480
Thr Thr Ser Asp Val Ser Lys Pro Lys Ala Asn Glu Ala Val Val Thr
        145                 150                 155

aat gag tca act aaa cca aaa aca aca gaa gca cca act gtt aat gag      528
Asn Glu Ser Thr Lys Pro Lys Thr Thr Glu Ala Pro Thr Val Asn Glu
    160                 165                 170

gaa tca ata gct gaa aca ccc aaa acc tca act aca caa caa gat tcg      576
Glu Ser Ile Ala Glu Thr Pro Lys Thr Ser Thr Thr Gln Gln Asp Ser
175                 180                 185                 190

act gag aag aat aat cca tct tta aaa gat aat tta aat tca tcc tca      624
Thr Glu Lys Asn Asn Pro Ser Leu Lys Asp Asn Leu Asn Ser Ser Ser
                195                 200                 205

acg aca tct aaa gaa agt aaa aca gac gaa cat tct act aag caa gct      672
Thr Thr Ser Lys Glu Ser Lys Thr Asp Glu His Ser Thr Lys Gln Ala
            210                 215                 220

caa atg tct act aat aaa tca aat tta gac aca aat gac tct cca act      720
Gln Met Ser Thr Asn Lys Ser Asn Leu Asp Thr Asn Asp Ser Pro Thr
        225                 230                 235

caa agt gag aaa act tca tca caa gca aat aac gac agt aca gat aat      768
Gln Ser Glu Lys Thr Ser Ser Gln Ala Asn Asn Asp Ser Thr Asp Asn
    240                 245                 250

cag tca gca cct tct aaa caa tta gat tca aaa cca tca gaa caa aaa      816
Gln Ser Ala Pro Ser Lys Gln Leu Asp Ser Lys Pro Ser Glu Gln Lys
255                 260                 265                 270

gta tat aaa aca aaa ttt aat gat gaa cct act caa gat gtt gaa cac      864
Val Tyr Lys Thr Lys Phe Asn Asp Glu Pro Thr Gln Asp Val Glu His
                275                 280                 285

acg aca act aaa tta aaa aca cct tct gtt tca aca gat agt tca gtc      912
Thr Thr Thr Lys Leu Lys Thr Pro Ser Val Ser Thr Asp Ser Ser Val
            290                 295                 300

aat gat aag caa gat tac aca cga agt gct gta gct agt tta ggt gtt      960
Asn Asp Lys Gln Asp Tyr Thr Arg Ser Ala Val Ala Ser Leu Gly Val
        305                 310                 315

gat tct aat gaa aca gaa gca att aca aat gca gtt aga gac aat tta     1008
Asp Ser Asn Glu Thr Glu Ala Ile Thr Asn Ala Val Arg Asp Asn Leu
    320                 325                 330

gat tta aaa gct gca tct aga gaa caa atc aat gaa gca atc att gct     1056
Asp Leu Lys Ala Ala Ser Arg Glu Gln Ile Asn Glu Ala Ile Ile Ala
335                 340                 345                 350

gaa gca cta aaa aaa gac ttt tct aac cct gat tat ggt gtc gat acg     1104
Glu Ala Leu Lys Lys Asp Phe Ser Asn Pro Asp Tyr Gly Val Asp Thr
                355                 360                 365

cca tta gct cta aac aga tct caa tca aaa aat tca cca cat aag agt     1152
Pro Leu Ala Leu Asn Arg Ser Gln Ser Lys Asn Ser Pro His Lys Ser
            370                 375                 380

gca agt cca cgc atg aat tta atg agt tta gct gct gag cct aat agt     1200
Ala Ser Pro Arg Met Asn Leu Met Ser Leu Ala Ala Glu Pro Asn Ser
        385                 390                 395
```

-continued

```
ggt aaa aat gtg aat gat aaa gtt aaa atc aca aac cct acg ctt tca     1248
Gly Lys Asn Val Asn Asp Lys Val Lys Ile Thr Asn Pro Thr Leu Ser
    400                 405                 410

ctt aat aag agt aat aat cac gct aat aac gta ata tgg cca aca agt     1296
Leu Asn Lys Ser Asn Asn His Ala Asn Asn Val Ile Trp Pro Thr Ser
415                 420                 425                 430

aac gaa caa ttt aat tta aaa gca aat tat gaa tta gat gac agc ata     1344
Asn Glu Gln Phe Asn Leu Lys Ala Asn Tyr Glu Leu Asp Asp Ser Ile
                435                 440                 445

aaa gag gga gat act ttt act att aag tat ggt cag tat att aga ccg     1392
Lys Glu Gly Asp Thr Phe Thr Ile Lys Tyr Gly Gln Tyr Ile Arg Pro
            450                 455                 460

ggt ggt tta gaa ctt cct gca ata aaa act caa cta cgt agt aag gat     1440
Gly Gly Leu Glu Leu Pro Ala Ile Lys Thr Gln Leu Arg Ser Lys Asp
        465                 470                 475

ggc tct att gta gct aat ggt gta tat gat aaa act aca aat acg acg     1488
Gly Ser Ile Val Ala Asn Gly Val Tyr Asp Lys Thr Thr Asn Thr Thr
    480                 485                 490

act tat aca ttt act aac tat gtt gat caa tat caa aat att aca ggt     1536
Thr Tyr Thr Phe Thr Asn Tyr Val Asp Gln Tyr Gln Asn Ile Thr Gly
495                 500                 505                 510

agt ttt gat tta att gcg acg cct aag agg gaa aca gca att aag gat     1584
Ser Phe Asp Leu Ile Ala Thr Pro Lys Arg Glu Thr Ala Ile Lys Asp
                515                 520                 525

aat cag aat tat cct atg gaa gtg acg att gct aac gaa gta gtc aaa     1632
Asn Gln Asn Tyr Pro Met Glu Val Thr Ile Ala Asn Glu Val Val Lys
            530                 535                 540

aaa gac ttc att gtg gat tat ggt aat aaa aag gac aat aca act aca     1680
Lys Asp Phe Ile Val Asp Tyr Gly Asn Lys Lys Asp Asn Thr Thr Thr
        545                 550                 555

gca gcg gta gca aat gtg gat aat gta aat aat aaa cat aac gaa gtt     1728
Ala Ala Val Ala Asn Val Asp Asn Val Asn Asn Lys His Asn Glu Val
    560                 565                 570

gtt tat cta aac caa aat aac caa aac cct aaa tat gct aaa tat ttc     1776
Val Tyr Leu Asn Gln Asn Asn Gln Asn Pro Lys Tyr Ala Lys Tyr Phe
575                 580                 585                 590

tca aca gta aaa aat ggt gaa ttt ata cca ggt gaa gtg aaa gtt tac     1824
Ser Thr Val Lys Asn Gly Glu Phe Ile Pro Gly Glu Val Lys Val Tyr
                595                 600                 605

gaa gtg acg gat acc aat gcg atg gta gat agc ttc aat cct gat tta     1872
Glu Val Thr Asp Thr Asn Ala Met Val Asp Ser Phe Asn Pro Asp Leu
            610                 615                 620

aat agt tct aat gta aaa gat gtg aca agt caa ttt gca cct aaa gta     1920
Asn Ser Ser Asn Val Lys Asp Val Thr Ser Gln Phe Ala Pro Lys Val
        625                 630                 635

agt gca gat ggt act aga gtt gat atc aat ttt gct aga agt atg gca     1968
Ser Ala Asp Gly Thr Arg Val Asp Ile Asn Phe Ala Arg Ser Met Ala
    640                 645                 650

aat ggt aaa aag tat att gta act caa gca gtg aga cca acg gga act     2016
Asn Gly Lys Lys Tyr Ile Val Thr Gln Ala Val Arg Pro Thr Gly Thr
655                 660                 665                 670

gga aat gtt tat acc gaa tat tgg tta aca aga gat ggt act acc aat     2064
Gly Asn Val Tyr Thr Glu Tyr Trp Leu Thr Arg Asp Gly Thr Thr Asn
                675                 680                 685

aca aat gat ttt tac cgt gga acg aag tct aca acg gtg act tat ctc     2112
Thr Asn Asp Phe Tyr Arg Gly Thr Lys Ser Thr Thr Val Thr Tyr Leu
            690                 695                 700

aat ggt tct tca aca gca cag ggg gat aat cct aca tat agt cta ggt     2160
Asn Gly Ser Ser Thr Ala Gln Gly Asp Asn Pro Thr Tyr Ser Leu Gly
        705                 710                 715
```

-continued

```
gac tat gta tgg tta gat aaa aat aaa aac ggt gtt caa gat gat gat     2208
Asp Tyr Val Trp Leu Asp Lys Asn Lys Asn Gly Val Gln Asp Asp Asp
    720                 725                 730

gag aaa ggt tta gca ggt gtt tat gtt act ctt aaa gac agt aac aat     2256
Glu Lys Gly Leu Ala Gly Val Tyr Val Thr Leu Lys Asp Ser Asn Asn
735                 740                 745                 750

aga gaa tta caa cgt gta act act gat caa tct gga cat tat caa ttt     2304
Arg Glu Leu Gln Arg Val Thr Thr Asp Gln Ser Gly His Tyr Gln Phe
                755                 760                 765

gat aat tta caa aat gga acg tac aca gtc gag ttt gcg att cct gat     2352
Asp Asn Leu Gln Asn Gly Thr Tyr Thr Val Glu Phe Ala Ile Pro Asp
            770                 775                 780

aat tat acg cca tct ccc gca aat aat tct aca aat gat gca ata gat     2400
Asn Tyr Thr Pro Ser Pro Ala Asn Asn Ser Thr Asn Asp Ala Ile Asp
        785                 790                 795

tca gat ggt gaa cgt gat ggt aca cgt aaa gta gtt gtt gcc aaa gga     2448
Ser Asp Gly Glu Arg Asp Gly Thr Arg Lys Val Val Val Ala Lys Gly
    800                 805                 810

aca att aat aat gct gat aat atg act gta gat act ggc ttt tat tta     2496
Thr Ile Asn Asn Ala Asp Asn Met Thr Val Asp Thr Gly Phe Tyr Leu
815                 820                 825                 830

act cct aaa tac aat gtc gga gat tat gta tgg gaa gat aca aat aaa     2544
Thr Pro Lys Tyr Asn Val Gly Asp Tyr Val Trp Glu Asp Thr Asn Lys
                835                 840                 845

gat ggt atc caa gat gac aat gaa aaa gga att tct ggt gtt aaa gta     2592
Asp Gly Ile Gln Asp Asp Asn Glu Lys Gly Ile Ser Gly Val Lys Val
            850                 855                 860

acg tta aaa aat aaa aat gga gat act att ggc aca acg aca aca gat     2640
Thr Leu Lys Asn Lys Asn Gly Asp Thr Ile Gly Thr Thr Thr Thr Asp
        865                 870                 875

tca aat ggt aaa tat gaa ttc aca ggt tta gag aac ggg gat tac aca     2688
Ser Asn Gly Lys Tyr Glu Phe Thr Gly Leu Glu Asn Gly Asp Tyr Thr
    880                 885                 890

ata gaa ttt gag acg ccg gaa ggc tac aca ccg act aaa caa aac tcg     2736
Ile Glu Phe Glu Thr Pro Glu Gly Tyr Thr Pro Thr Lys Gln Asn Ser
895                 900                 905                 910

gga agt gac gaa ggt aaa gat tca aac ggt acg aaa aca aca gtc aca     2784
Gly Ser Asp Glu Gly Lys Asp Ser Asn Gly Thr Lys Thr Thr Val Thr
                915                 920                 925

gtc aaa gat gca gat aat aaa aca ata gac tca ggt ttc tac aag cca     2832
Val Lys Asp Ala Asp Asn Lys Thr Ile Asp Ser Gly Phe Tyr Lys Pro
            930                 935                 940

aca tat aac tta ggt gac tat gta tgg gaa gat aca aat aaa gat ggt     2880
Thr Tyr Asn Leu Gly Asp Tyr Val Trp Glu Asp Thr Asn Lys Asp Gly
        945                 950                 955

att caa gac gac agt gaa aaa ggg att tct ggg gtt aaa gtg acg tta     2928
Ile Gln Asp Asp Ser Glu Lys Gly Ile Ser Gly Val Lys Val Thr Leu
    960                 965                 970

aaa gat aaa aat gga aat gcc att ggg aca acg aca aca gac gca agt     2976
Lys Asp Lys Asn Gly Asn Ala Ile Gly Thr Thr Thr Thr Asp Ala Ser
975                 980                 985                 990

ggt cat tat caa ttt aaa gga tta gaa aat  gga agc tac aca gtt  gag   3024
Gly His Tyr Gln Phe Lys Gly Leu Glu Asn  Gly Ser Tyr Thr Val  Glu
                995                 1000                1005

ttt gag aca cca  tca ggt tat aca ccg  aca aaa gcg aat tca  ggt      3069
Phe Glu Thr Pro  Ser Gly Tyr Thr Pro  Thr Lys Ala Asn Ser  Gly
            1010                1015                1020

caa gat ata act  gta gat tcc aac ggt  ata aca aca aca ggt  atc      3114
Gln Asp Ile Thr  Val Asp Ser Asn Gly  Ile Thr Thr Thr Gly  Ile
```

-continued

```
            1025                1030                1035

att aac gga gct  gat aat ctc aca att  gat agt ggt ttc tac  aaa      3159
Ile Asn Gly Ala  Asp Asn Leu Thr Ile  Asp Ser Gly Phe Tyr  Lys
            1040                1045                1050

aca cca aaa tat  agt gtc gga gat tat  gta tgg gaa gat aca  aat      3204
Thr Pro Lys Tyr  Ser Val Gly Asp Tyr  Val Trp Glu Asp Thr  Asn
            1055                1060                1065

aaa gat ggt atc  caa gat gac aat gaa  aag gga att tct ggt  gtt      3249
Lys Asp Gly Ile  Gln Asp Asp Asn Glu  Lys Gly Ile Ser Gly  Val
            1070                1075                1080

aaa gta acg tta  aag gat gaa aaa gga  aat ata att agc act  aca      3294
Lys Val Thr Leu  Lys Asp Glu Lys Gly  Asn Ile Ile Ser Thr  Thr
            1085                1090                1095

aca act gat gaa  aat ggg aag tat caa  ttt gat aat tta gat  agt      3339
Thr Thr Asp Glu  Asn Gly Lys Tyr Gln  Phe Asp Asn Leu Asp  Ser
            1100                1105                1110

ggt aat tac att  att cat ttt gag aaa  ccg gaa ggc atg act  caa      3384
Gly Asn Tyr Ile  Ile His Phe Glu Lys  Pro Glu Gly Met Thr  Gln
            1115                1120                1125

act aca gca aat  tct gga aat gat gat  gaa aaa gat gct gat  ggg      3429
Thr Thr Ala Asn  Ser Gly Asn Asp Asp  Glu Lys Asp Ala Asp  Gly
            1130                1135                1140

gaa gat gtt cgt  gtt acg att act gat  cat gat gac ttt agt  ata      3474
Glu Asp Val Arg  Val Thr Ile Thr Asp  His Asp Asp Phe Ser  Ile
            1145                1150                1155

gat aat ggt tat  ttt gac gat gat tca  gac agt gac tca gac  gca      3519
Asp Asn Gly Tyr  Phe Asp Asp Asp Ser  Asp Ser Asp Ser Asp  Ala
            1160                1165                1170

gat agt gat tca  gac tca gac agt gac  tcg gac gca gac agc  gat      3564
Asp Ser Asp Ser  Asp Ser Asp Ser Asp  Ser Asp Ala Asp Ser  Asp
            1175                1180                1185

tct gac gca gac  agt gac tca gac gca  gat agt gat tct gac  tca      3609
Ser Asp Ala Asp  Ser Asp Ser Asp Ala  Asp Ser Asp Ser Asp  Ser
            1190                1195                1200

gac agc gac tca  gac gca gat agt gat  tcc gat tca gac agc  gac      3654
Asp Ser Asp Ser  Asp Ala Asp Ser Asp  Ser Asp Ser Asp Ser  Asp
            1205                1210                1215

tcg gat tca gat  agt gat tcg gat gca  gac agc gac tcg gat  tct      3699
Ser Asp Ser Asp  Ser Asp Ser Asp Ala  Asp Ser Asp Ser Asp  Ser
            1220                1225                1230

gac agt gat tct  gac gca gac agt gac  tca gat tca gac agt  gac      3744
Asp Ser Asp Ser  Asp Ala Asp Ser Asp  Ser Asp Ser Asp Ser  Asp
            1235                1240                1245

tcg gat tca gac  agc gat tcg gat tcc  gat tca gac agt gac  tcg      3789
Ser Asp Ser Asp  Ser Asp Ser Asp Ser  Asp Ser Asp Ser Asp  Ser
            1250                1255                1260

gat tca gac agt  gac tca gac tcc gac  agt gat tcc gat tca  gat      3834
Asp Ser Asp Ser  Asp Ser Asp Ser Asp  Ser Asp Ser Asp Ser  Asp
            1265                1270                1275

agc gac tcc gac  gca gat agt gat tcg  gac gca gac agt gac  tca      3879
Ser Asp Ser Asp  Ala Asp Ser Asp Ser  Asp Ala Asp Ser Asp  Ser
            1280                1285                1290

gat tca gac agt  gat tcg gac gca gac  agt gac tcg gac tca  gat      3924
Asp Ser Asp Ser  Asp Ser Asp Ala Asp  Ser Asp Ser Asp Ser  Asp
            1295                1300                1305

agt gat tca gat  gca gac agc gat tca  gac tca gat agc gac  tcg      3969
Ser Asp Ser Asp  Ala Asp Ser Asp Ser  Asp Ser Asp Ser Asp  Ser
            1310                1315                1320

gat tca gac agc  gac tcc gac gca gac  agc gac tcg gat tca  gat      4014
```

-continued

```
Asp Ser Asp Ser  Asp Ser Asp Ala Asp  Ser Asp Ser Asp Ser  Asp
            1325                 1330                 1335

agt gat tct gac  tca gac agt gac tca  gat tcc gat agt gat  tcg      4059
Ser Asp Ser Asp  Ser Asp Ser Asp Ser  Asp Ser Asp Ser Asp  Ser
            1340                 1345                 1350

gat tca gat agt  gat tcc gac gca gac  agc gat tcg gat tcc  gat      4104
Asp Ser Asp Ser  Asp Ser Asp Ala Asp  Ser Asp Ser Asp Ser  Asp
            1355                 1360                 1365

agc gat tca gac  tca gac agc gat tca  gat tca gac agc gac  tca      4149
Ser Asp Ser Asp  Ser Asp Ser Asp Ser  Asp Ser Asp Ser Asp  Ser
            1370                 1375                 1380

gat tca gat agt  gat tcc gac gca gac  agc gat gca gac agc  gac      4194
Asp Ser Asp Ser  Asp Ser Asp Ala Asp  Ser Asp Ala Asp Ser  Asp
            1385                 1390                 1395

tca gac gca gac  agt gat tca gat gca  gac agc gat tct gac  tca      4239
Ser Asp Ala Asp  Ser Asp Ser Asp Ala  Asp Ser Asp Ser Asp  Ser
            1400                 1405                 1410

gat agt gac tca  gac gca gat agt gat  tcc gat tcc gat agc  gat      4284
Asp Ser Asp Ser  Asp Ala Asp Ser Asp  Ser Asp Ser Asp Ser  Asp
            1415                 1420                 1425

tca gat tct gat  agt gac tca gac tca  gac agt gac tca gat  tcc      4329
Ser Asp Ser Asp  Ser Asp Ser Asp Ser  Asp Ser Asp Ser Asp  Ser
            1430                 1435                 1440

gat agc gac tcg  gat tca gat agt gat  tcc gac gca gac agt  gac      4374
Asp Ser Asp Ser  Asp Ser Asp Ser Asp  Ser Asp Ala Asp Ser  Asp
            1445                 1450                 1455

tca gac tca gat  agt gac tcg gat tcc  gat agt gat tcc gac  gca      4419
Ser Asp Ser Asp  Ser Asp Ser Asp Ser  Asp Ser Asp Ser Asp  Ala
            1460                 1465                 1470

gac agc gat tct  gac tca gat agt gac  tca gac gca gat agt  gat      4464
Asp Ser Asp Ser  Asp Ser Asp Ser Asp  Ser Asp Ala Asp Ser  Asp
            1475                 1480                 1485

tcc gat tcc gat  agc gat tcg gat gca  gac agc gac tcg gat  tca      4509
Ser Asp Ser Asp  Ser Asp Ser Asp Ala  Asp Ser Asp Ser Asp  Ser
            1490                 1495                 1500

gat agt gat tcc  gac gca gac agt gac  tca gac tca gat agt  gac      4554
Asp Ser Asp Ser  Asp Ala Asp Ser Asp  Ser Asp Ser Asp Ser  Asp
            1505                 1510                 1515

tcg gat tcc gat  agt gat tcc gac gca  gac agc gat tcg gat  tcc      4599
Ser Asp Ser Asp  Ser Asp Ser Asp Ala  Asp Ser Asp Ser Asp  Ser
            1520                 1525                 1530

gat agc gat tca  gac tcc gac agc gat  tca gat tca gac agc  gac      4644
Asp Ser Asp Ser  Asp Ser Asp Ser Asp  Ser Asp Ser Asp Ser  Asp
            1535                 1540                 1545

tca gat tcc gat  agt gat tcc gat tca  gac agt gac tcg gat  tcc      4689
Ser Asp Ser Asp  Ser Asp Ser Asp Ser  Asp Ser Asp Ser Asp  Ser
            1550                 1555                 1560

gat agt gac tca  gac tca gac agt gac  tca gat tca gat agc  gac      4734
Asp Ser Asp Ser  Asp Ser Asp Ser Asp  Ser Asp Ser Asp Ser  Asp
            1565                 1570                 1575

tca gat tca gac  agt gat tcg gac tca  gat agt gac tcc gat  tca      4779
Ser Asp Ser Asp  Ser Asp Ser Asp Ser  Asp Ser Asp Ser Asp  Ser
            1580                 1585                 1590

gac agt gat tcg  gat tcc gat agc gat  tcg gat tcc gat agt  gac      4824
Asp Ser Asp Ser  Asp Ser Asp Ser Asp  Ser Asp Ser Asp Ser  Asp
            1595                 1600                 1605

tcg gat tca gac  agt gat tcg gac tca  gac agc gac tcc gat  tca      4869
Ser Asp Ser Asp  Ser Asp Ser Asp Ser  Asp Ser Asp Ser Asp  Ser
            1610                 1615                 1620
```

-continued

```
gat agt gat tcc  gac tca gac agc gat  tcg gat tcc gat agt  gac      4914
Asp Ser Asp Ser  Asp Ser Asp Ser Asp  Ser Asp Ser Asp Ser  Asp
            1625                 1630                 1635

tcg gat tca gac  agt gat tcg gac tca  gac agc gac tcc gat  tca      4959
Ser Asp Ser Asp  Ser Asp Ser Asp Ser  Asp Ser Asp Ser Asp  Ser
            1640                 1645                 1650

gat agt gat tcc  gac gca gac agc gac  tcc gat tca gat agt  gat      5004
Asp Ser Asp Ser  Asp Ala Asp Ser Asp  Ser Asp Ser Asp Ser  Asp
            1655                 1660                 1665

tcg gac gca gac  agc gat tcc gat agt  gac tcg gat tca gac  agt      5049
Ser Asp Ala Asp  Ser Asp Ser Asp Ser  Asp Ser Asp Ser Asp  Ser
            1670                 1675                 1680

gat tcg gac tca  gac agc gat tcc gat  tca gac agt gac tcg  gac      5094
Asp Ser Asp Ser  Asp Ser Asp Ser Asp  Ser Asp Ser Asp Ser  Asp
            1685                 1690                 1695

tca gat agc gac  tcg gat tca gac agt  gac tcg gac tca gat  agt      5139
Ser Asp Ser Asp  Ser Asp Ser Asp Ser  Asp Ser Asp Ser Asp  Ser
            1700                 1705                 1710

gac tcc gat tca  gac agc gac tcg gat  tct gat aaa aat gca  aaa      5184
Asp Ser Asp Ser  Asp Ser Asp Ser Asp  Ser Asp Lys Asn Ala  Lys
            1715                 1720                 1725

gat aaa tta cct  gat aca gga gca aat  gaa gat cat gat tct  aaa      5229
Asp Lys Leu Pro  Asp Thr Gly Ala Asn  Glu Asp His Asp Ser  Lys
            1730                 1735                 1740

ggc aca tta ctt  gga act tta ttt gca  ggt tta gga gca tta  tta      5274
Gly Thr Leu Leu  Gly Thr Leu Phe Ala  Gly Leu Gly Ala Leu  Leu
            1745                 1750                 1755

tta gga aga cgt  cgt aaa aaa gat aat  aaa gaa aaa tag cac tat      5319
Leu Gly Arg Arg  Arg Lys Lys Asp Asn  Lys Glu Lys     His Tyr
            1760                 1765                     1770

tga ttc att cat aag tta  ttt caa gcc agg tct  ata tgg cct ggt      5364
    Phe Ile His Lys Leu  Phe Gln Ala Arg Ser  Ile Trp Pro Gly
                    1775                 1780

ttg  aaa tca tat taa att gaa  agg aga aaa aga tga gta  tgg          5406
Leu  Lys Ser Tyr     Ile Glu  Arg Arg Lys Arg     Val  Trp
1785                     1790                 1795
```

<210> SEQ ID NO 2
<211> LENGTH: 11
<212> TYPE: PRT
<213> ORGANISM: Staphylococcus epidermidis

<400> SEQUENCE: 2

```
Tyr Trp Ile Asn Tyr Ala Tyr Lys Val Phe Thr
1               5                   10
```

<210> SEQ ID NO 3
<211> LENGTH: 15
<212> TYPE: PRT
<213> ORGANISM: Staphylococcus epidermidis

<400> SEQUENCE: 3

```
Lys Cys Lys Cys Asn Leu Gln Val Asn Ile Gln Ile Ile Ser Leu
1               5                   10                  15
```

<210> SEQ ID NO 4
<211> LENGTH: 1742
<212> TYPE: PRT
<213> ORGANISM: Staphylococcus epidermidis

<400> SEQUENCE: 4

```
Asn Ile Tyr Phe Asn Trp Arg Tyr Ser Met Lys Lys Arg Arg Gln Gly
```

-continued

```
1               5                   10                  15

Pro Ile Asn Lys Arg Val Asp Phe Leu Ser Asn Lys Val Asn Lys Tyr
            20                  25                  30

Ser Ile Arg Lys Phe Thr Val Gly Thr Ala Ser Ile Leu Val Gly Ala
        35                  40                  45

Thr Leu Met Phe Gly Ala Ala Asp Asn Glu Ala Lys Ala Ala Glu Asp
    50                  55                  60

Asn Gln Leu Glu Ser Ala Ser Lys Glu Glu Gln Lys Gly Ser Arg Asp
65                  70                  75                  80

Asn Glu Asn Ser Lys Leu Asn Gln Val Asp Leu Asp Asn Gly Ser His
                85                  90                  95

Ser Ser Glu Lys Thr Thr Asn Val Asn Asn Ala Thr Glu Val Lys Lys
            100                 105                 110

Val Glu Ala Pro Thr Thr Ser Asp Val Ser Lys Pro Lys Ala Asn Glu
        115                 120                 125

Ala Val Val Thr Asn Glu Ser Thr Lys Pro Lys Thr Thr Glu Ala Pro
    130                 135                 140

Thr Val Asn Glu Glu Ser Ile Ala Glu Thr Pro Lys Thr Ser Thr Thr
145                 150                 155                 160

Gln Gln Asp Ser Thr Glu Lys Asn Asn Pro Ser Leu Lys Asp Asn Leu
                165                 170                 175

Asn Ser Ser Ser Thr Thr Ser Lys Glu Ser Lys Thr Asp Glu His Ser
            180                 185                 190

Thr Lys Gln Ala Gln Met Ser Thr Asn Lys Ser Asn Leu Asp Thr Asn
        195                 200                 205

Asp Ser Pro Thr Gln Ser Glu Lys Thr Ser Ser Gln Ala Asn Asn Asp
    210                 215                 220

Ser Thr Asp Asn Gln Ser Ala Pro Ser Lys Gln Leu Asp Ser Lys Pro
225                 230                 235                 240

Ser Glu Gln Lys Val Tyr Lys Thr Lys Phe Asn Asp Glu Pro Thr Gln
                245                 250                 255

Asp Val Glu His Thr Thr Thr Lys Leu Lys Thr Pro Ser Val Ser Thr
            260                 265                 270

Asp Ser Ser Val Asn Asp Lys Gln Asp Tyr Thr Arg Ser Ala Val Ala
        275                 280                 285

Ser Leu Gly Val Asp Ser Asn Glu Thr Glu Ala Ile Thr Asn Ala Val
    290                 295                 300

Arg Asp Asn Leu Asp Leu Lys Ala Ala Ser Arg Glu Gln Ile Asn Glu
305                 310                 315                 320

Ala Ile Ile Ala Glu Ala Leu Lys Lys Asp Phe Ser Asn Pro Asp Tyr
                325                 330                 335

Gly Val Asp Thr Pro Leu Ala Leu Asn Arg Ser Gln Ser Lys Asn Ser
            340                 345                 350

Pro His Lys Ser Ala Ser Pro Arg Met Asn Leu Met Ser Leu Ala Ala
        355                 360                 365

Glu Pro Asn Ser Gly Lys Asn Val Asn Asp Lys Val Lys Ile Thr Asn
    370                 375                 380

Pro Thr Leu Ser Leu Asn Lys Ser Asn Asn His Ala Asn Asn Val Ile
385                 390                 395                 400

Trp Pro Thr Ser Asn Glu Gln Phe Asn Leu Lys Ala Asn Tyr Glu Leu
                405                 410                 415

Asp Asp Ser Ile Lys Glu Gly Asp Thr Phe Thr Ile Lys Tyr Gly Gln
            420                 425                 430
```

-continued

```
Tyr Ile Arg Pro Gly Gly Leu Glu Leu Pro Ala Ile Lys Thr Gln Leu
        435                 440                 445

Arg Ser Lys Asp Gly Ser Ile Val Ala Asn Gly Val Tyr Asp Lys Thr
    450                 455                 460

Thr Asn Thr Thr Thr Tyr Thr Phe Thr Asn Tyr Val Asp Gln Tyr Gln
465                 470                 475                 480

Asn Ile Thr Gly Ser Phe Asp Leu Ile Ala Thr Pro Lys Arg Glu Thr
                485                 490                 495

Ala Ile Lys Asp Asn Gln Asn Tyr Pro Met Glu Val Thr Ile Ala Asn
            500                 505                 510

Glu Val Val Lys Lys Asp Phe Ile Val Asp Tyr Gly Asn Lys Lys Asp
        515                 520                 525

Asn Thr Thr Thr Ala Ala Val Ala Asn Val Asp Asn Val Asn Asn Lys
    530                 535                 540

His Asn Glu Val Val Tyr Leu Asn Gln Asn Asn Gln Asn Pro Lys Tyr
545                 550                 555                 560

Ala Lys Tyr Phe Ser Thr Val Lys Asn Gly Glu Phe Ile Pro Gly Glu
                565                 570                 575

Val Lys Val Tyr Glu Val Thr Asp Thr Asn Ala Met Val Asp Ser Phe
            580                 585                 590

Asn Pro Asp Leu Asn Ser Ser Asn Val Lys Asp Val Thr Ser Gln Phe
        595                 600                 605

Ala Pro Lys Val Ser Ala Asp Gly Thr Arg Val Asp Ile Asn Phe Ala
    610                 615                 620

Arg Ser Met Ala Asn Gly Lys Lys Tyr Ile Val Thr Gln Ala Val Arg
625                 630                 635                 640

Pro Thr Gly Thr Gly Asn Val Tyr Thr Glu Tyr Trp Leu Thr Arg Asp
                645                 650                 655

Gly Thr Thr Asn Thr Asn Asp Phe Tyr Arg Gly Thr Lys Ser Thr Thr
            660                 665                 670

Val Thr Tyr Leu Asn Gly Ser Ser Thr Ala Gln Gly Asp Asn Pro Thr
        675                 680                 685

Tyr Ser Leu Gly Asp Tyr Val Trp Leu Asp Lys Asn Lys Asn Gly Val
    690                 695                 700

Gln Asp Asp Asp Glu Lys Gly Leu Ala Gly Val Tyr Val Thr Leu Lys
705                 710                 715                 720

Asp Ser Asn Asn Arg Glu Leu Gln Arg Val Thr Thr Asp Gln Ser Gly
                725                 730                 735

His Tyr Gln Phe Asp Asn Leu Gln Asn Gly Thr Tyr Thr Val Glu Phe
            740                 745                 750

Ala Ile Pro Asp Asn Tyr Thr Pro Ser Pro Ala Asn Asn Ser Thr Asn
        755                 760                 765

Asp Ala Ile Asp Ser Asp Gly Glu Arg Asp Gly Thr Arg Lys Val Val
    770                 775                 780

Val Ala Lys Gly Thr Ile Asn Asn Ala Asp Asn Met Thr Val Asp Thr
785                 790                 795                 800

Gly Phe Tyr Leu Thr Pro Lys Tyr Asn Val Gly Asp Tyr Val Trp Glu
                805                 810                 815

Asp Thr Asn Lys Asp Gly Ile Gln Asp Asp Asn Glu Lys Gly Ile Ser
            820                 825                 830

Gly Val Lys Val Thr Leu Lys Asn Lys Asn Gly Asp Thr Ile Gly Thr
        835                 840                 845
```

-continued

```
Thr Thr Thr Asp Ser Asn Gly Lys Tyr Glu Phe Thr Gly Leu Glu Asn
    850                 855                 860

Gly Asp Tyr Thr Ile Glu Phe Glu Thr Pro Glu Gly Tyr Thr Pro Thr
865                 870                 875                 880

Lys Gln Asn Ser Gly Ser Asp Glu Gly Lys Asp Ser Asn Gly Thr Lys
                885                 890                 895

Thr Thr Val Thr Val Lys Asp Ala Asp Asn Lys Thr Ile Asp Ser Gly
            900                 905                 910

Phe Tyr Lys Pro Thr Tyr Asn Leu Gly Asp Tyr Val Trp Glu Asp Thr
        915                 920                 925

Asn Lys Asp Gly Ile Gln Asp Asp Ser Glu Lys Gly Ile Ser Gly Val
    930                 935                 940

Lys Val Thr Leu Lys Asp Lys Asn Gly Asn Ala Ile Gly Thr Thr Thr
945                 950                 955                 960

Thr Asp Ala Ser Gly His Tyr Gln Phe Lys Gly Leu Glu Asn Gly Ser
                965                 970                 975

Tyr Thr Val Glu Phe Glu Thr Pro Ser Gly Tyr Thr Pro Thr Lys Ala
            980                 985                 990

Asn Ser Gly Gln Asp Ile Thr Val  Asp Ser Asn Gly Ile  Thr Thr Thr
        995                 1000                1005

Gly Ile  Ile Asn Gly Ala Asp  Asn Leu Thr Ile Asp  Ser Gly Phe
    1010                1015                1020

Tyr Lys  Thr Pro Lys Tyr Ser  Val Gly Asp Tyr Val  Trp Glu Asp
    1025                1030                1035

Thr Asn  Lys Asp Gly Ile Gln  Asp Asp Asn Glu Lys  Gly Ile Ser
    1040                1045                1050

Gly Val  Lys Val Thr Leu Lys  Asp Glu Lys Gly Asn  Ile Ile Ser
    1055                1060                1065

Thr Thr  Thr Thr Asp Glu Asn  Gly Lys Tyr Gln Phe  Asp Asn Leu
    1070                1075                1080

Asp Ser  Gly Asn Tyr Ile Ile  His Phe Glu Lys Pro  Glu Gly Met
    1085                1090                1095

Thr Gln  Thr Thr Ala Asn Ser  Gly Asn Asp Asp Glu  Lys Asp Ala
    1100                1105                1110

Asp Gly  Glu Asp Val Arg Val  Thr Ile Thr Asp His  Asp Asp Phe
    1115                1120                1125

Ser Ile  Asp Asn Gly Tyr Phe  Asp Asp Asp Ser Asp  Ser Asp Ser
    1130                1135                1140

Asp Ala  Asp Ser Asp Ser Asp  Ser Asp Ser Asp Ser  Asp Ala Asp
    1145                1150                1155

Ser Asp  Ser Asp Ala Asp Ser  Asp Ser Asp Ala Asp  Ser Asp Ser
    1160                1165                1170

Asp Ser  Asp Ser Asp Ser Asp  Ala Asp Ser Asp Ser  Asp Ser Asp
    1175                1180                1185

Ser Asp  Ser Asp Ser Asp Ser  Asp Ser Asp Ala Asp  Ser Asp Ser
    1190                1195                1200

Asp Ser  Asp Ser Asp Ser Asp  Ala Asp Ser Asp Ser  Asp Ser Asp
    1205                1210                1215

Ser Asp  Ser Asp Ser Asp Ser  Asp Ser Asp Ser Asp  Ser Asp Ser
    1220                1225                1230

Asp Ser  Asp Ser Asp Ser Asp  Ser Asp Ser Asp Ser  Asp Ser Asp
    1235                1240                1245

Ser Asp  Ser Asp Ser Asp Ala  Asp Ser Asp Ser Asp  Ala Asp Ser
```

-continued

```
    1250                1255                1260

Asp Ser  Asp Ser Asp Ser Asp  Ser Asp Ala Asp Ser  Asp Ser Asp
    1265                1270                1275

Ser Asp  Ser Asp Ser Asp Ala  Asp Ser Asp Ser Asp  Ser Asp Ser
    1280                1285                1290

Asp Ser  Asp Ser Asp Ser Asp  Ser Asp Ala Asp Ser  Asp Ser Asp
    1295                1300                1305

Ser Asp  Ser Asp Ser Asp Ser  Asp Ser Asp Ser Asp  Ser Asp Ser
    1310                1315                1320

Asp Ser  Asp Ser Asp Ser Asp  Ser Asp Ala Asp Ser  Asp Ser Asp
    1325                1330                1335

Ser Asp  Ser Asp Ser Asp Ser  Asp Ser Asp Ser Asp  Ser Asp Ser
    1340                1345                1350

Asp Ser  Asp Ser Asp Ser Asp  Ser Asp Ala Asp Ser  Asp Ala Asp
    1355                1360                1365

Ser Asp  Ser Asp Ala Asp Ser  Asp Ser Asp Ala Asp  Ser Asp Ser
    1370                1375                1380

Asp Ser  Asp Ser Asp Ser Asp  Ala Asp Ser Asp Ser  Asp Ser Asp
    1385                1390                1395

Ser Asp  Ser Asp Ser Asp Ser  Asp Ser Asp Ser Asp  Ser Asp Ser
    1400                1405                1410

Asp Ser  Asp Ser Asp Ser Asp  Ser Asp Ser Asp Ser  Asp Ala Asp
    1415                1420                1425

Ser Asp  Ser Asp Ser Asp Ser  Asp Ser Asp Ser Asp  Ser Asp Ser
    1430                1435                1440

Asp Ala  Asp Ser Asp Ser Asp  Ser Asp Ser Asp Ser  Asp Ala Asp
    1445                1450                1455

Ser Asp  Ser Asp Ser Asp Ser  Asp Ser Asp Ala Asp  Ser Asp Ser
    1460                1465                1470

Asp Ser  Asp Ser Asp Ser Asp  Ala Asp Ser Asp Ser  Asp Ser Asp
    1475                1480                1485

Ser Asp  Ser Asp Ser Asp Ser  Asp Ser Asp Ala Asp  Ser Asp Ser
    1490                1495                1500

Asp Ser  Asp Ser Asp Ser Asp  Ser Asp Ser Asp Ser  Asp Ser Asp
    1505                1510                1515

Ser Asp  Ser Asp Ser Asp Ser  Asp Ser Asp Ser Asp  Ser Asp Ser
    1520                1525                1530

Asp Ser  Asp Ser Asp Ser Asp  Ser Asp Ser Asp Ser  Asp Ser Asp
    1535                1540                1545

Ser Asp  Ser Asp Ser Asp Ser  Asp Ser Asp Ser Asp  Ser Asp Ser
    1550                1555                1560

Asp Ser  Asp Ser Asp Ser Asp  Ser Asp Ser Asp Ser  Asp Ser Asp
    1565                1570                1575

Ser Asp  Ser Asp Ser Asp Ser  Asp Ser Asp Ser Asp  Ser Asp Ser
    1580                1585                1590

Asp Ser  Asp Ser Asp Ser Asp  Ser Asp Ser Asp Ser  Asp Ser Asp
    1595                1600                1605

Ser Asp  Ser Asp Ser Asp Ser  Asp Ser Asp Ser Asp  Ser Asp Ser
    1610                1615                1620

Asp Ser  Asp Ser Asp Ser Asp  Ala Asp Ser Asp Ser  Asp Ser Asp
    1625                1630                1635

Ser Asp  Ser Asp Ala Asp Ser  Asp Ser Asp Ser Asp  Ser Asp Ser
    1640                1645                1650
```

-continued

```
Asp Ser  Asp Ser Asp Ser Asp  Ser Asp Ser Asp Ser  Asp Ser Asp
    1655                1660                1665

Ser Asp  Ser Asp Ser Asp Ser  Asp Ser Asp Ser Asp  Ser Asp Ser
    1670                1675                1680

Asp Ser  Asp Ser Asp Ser Asp  Ser Asp Ser Asp Ser  Asp Lys Asn
    1685                1690                1695

Ala Lys  Asp Lys Leu Pro Asp  Thr Gly Ala Asn Glu  Asp His Asp
    1700                1705                1710

Ser Lys  Gly Thr Leu Leu Gly  Thr Leu Phe Ala Gly  Leu Gly Ala
    1715                1720                1725

Leu Leu  Leu Gly Arg Arg Arg  Lys Lys Asp Asn Lys  Glu Lys
    1730                1735                1740


<210> SEQ ID NO 5
<211> LENGTH: 18
<212> TYPE: PRT
<213> ORGANISM: Staphylococcus epidermidis

<400> SEQUENCE: 5

Phe Ile His Lys Leu Phe Gln Ala Arg Ser Ile Trp Pro Gly Leu Lys
1               5                   10                  15

Ser Tyr


<210> SEQ ID NO 6
<211> LENGTH: 6
<212> TYPE: PRT
<213> ORGANISM: Staphylococcus epidermidis

<400> SEQUENCE: 6

Ile Glu Arg Arg Lys Arg
1               5


<210> SEQ ID NO 7
<211> LENGTH: 2976
<212> TYPE: DNA
<213> ORGANISM: Staphylococcus epidermidis
<220> FEATURE:
<221> NAME/KEY: CDS
<222> LOCATION: (3)..(2975)

<400> SEQUENCE: 7

at att gca aaa aag act tat ata cta tat tgt att tta ctc tag aaa        47
   Ile Ala Lys Lys Thr Tyr Ile Leu Tyr Cys Ile Leu Leu     Lys
   1               5                   10

cga ttt tta ctt gaa aat tac att gaa ata gtc aaa gat aag gag ttt       95
Arg Phe Leu Leu Glu Asn Tyr Ile Glu Ile Val Lys Asp Lys Glu Phe
15                  20                  25                  30

tta tga tta aaa aaa aat aat tta cta act aaa aag aaa cct ata gca      143
Leu     Leu Lys Lys Asn Asn Leu Leu Thr Lys Lys Lys Pro Ile Ala
                    35                  40                  45

aat aaa tcc aat aaa tat gca att aga aaa ttc aca gta ggt aca gcg      191
Asn Lys Ser Asn Lys Tyr Ala Ile Arg Lys Phe Thr Val Gly Thr Ala
                50                  55                  60

tct att gta ata ggt gca gca tta ttg ttt ggt tta ggt cat aat gag      239
Ser Ile Val Ile Gly Ala Ala Leu Leu Phe Gly Leu Gly His Asn Glu
            65                  70                  75

gcc aaa gct gag gag aat aca gta caa gac gtt aaa gat tcg aat atg      287
Ala Lys Ala Glu Glu Asn Thr Val Gln Asp Val Lys Asp Ser Asn Met
        80                  85                  90

gat gat gaa tta tca gat agc aat gat cag tcc agt aat gaa gaa aag      335
```

-continued

```
Asp Asp Glu Leu Ser Asp Ser Asn Asp Gln Ser Ser Asn Glu Glu Lys
    95                  100                 105

aat gat gta atc aat aat agt cag tca ata aac acc gat gat gat aac      383
Asn Asp Val Ile Asn Asn Ser Gln Ser Ile Asn Thr Asp Asp Asp Asn
110                 115                 120                 125

caa ata aaa aaa gaa gaa acg aat agc aac gat gcc ata gaa aat cgc      431
Gln Ile Lys Lys Glu Glu Thr Asn Ser Asn Asp Ala Ile Glu Asn Arg
                130                 135                 140

tct aaa gat ata aca cag tca aca aca aat gta gat gaa aac gaa gca      479
Ser Lys Asp Ile Thr Gln Ser Thr Thr Asn Val Asp Glu Asn Glu Ala
            145                 150                 155

aca ttt tta caa aag acc cct caa gat aat act cag ctt aaa gaa gaa      527
Thr Phe Leu Gln Lys Thr Pro Gln Asp Asn Thr Gln Leu Lys Glu Glu
        160                 165                 170

gtg gta aaa gaa ccc tca tca gtc gaa tcc tca aat tca tca atg gat      575
Val Val Lys Glu Pro Ser Ser Val Glu Ser Ser Asn Ser Ser Met Asp
    175                 180                 185

act gcc caa caa cca tct cat aca aca ata aat agt gaa gca tct att      623
Thr Ala Gln Gln Pro Ser His Thr Thr Ile Asn Ser Glu Ala Ser Ile
190                 195                 200                 205

caa aca agt gat aat gaa gaa aat tcc cgc gta tca gat ttt gct aac      671
Gln Thr Ser Asp Asn Glu Glu Asn Ser Arg Val Ser Asp Phe Ala Asn
                210                 215                 220

tct aaa ata ata gag agt aac act gaa tcc aat aaa gaa gag aat act      719
Ser Lys Ile Ile Glu Ser Asn Thr Glu Ser Asn Lys Glu Glu Asn Thr
            225                 230                 235

ata gag caa cct aac aaa gta aga gaa gat tca ata aca agt caa ccg      767
Ile Glu Gln Pro Asn Lys Val Arg Glu Asp Ser Ile Thr Ser Gln Pro
        240                 245                 250

tct agc tat aaa aat ata gat gaa aaa att tca aat caa gat gag tta      815
Ser Ser Tyr Lys Asn Ile Asp Glu Lys Ile Ser Asn Gln Asp Glu Leu
    255                 260                 265

tta aat tta cca ata aat gaa tat gaa aat aag gtt aga ccg tta tct      863
Leu Asn Leu Pro Ile Asn Glu Tyr Glu Asn Lys Val Arg Pro Leu Ser
270                 275                 280                 285

aca aca tct gcc caa cca tcg agt aag cgt gta acc gta aat caa tta      911
Thr Thr Ser Ala Gln Pro Ser Ser Lys Arg Val Thr Val Asn Gln Leu
                290                 295                 300

gcg gca gaa caa ggt tcg aat gtt aat cat tta att aaa gtt act gat      959
Ala Ala Glu Gln Gly Ser Asn Val Asn His Leu Ile Lys Val Thr Asp
            305                 310                 315

caa agt att act gaa gga tat gat gat agt gat ggt att att aaa gca     1007
Gln Ser Ile Thr Glu Gly Tyr Asp Asp Ser Asp Gly Ile Ile Lys Ala
        320                 325                 330

cat gat gct gaa aac tta atc tat gat gta act ttt gaa gta gat gat     1055
His Asp Ala Glu Asn Leu Ile Tyr Asp Val Thr Phe Glu Val Asp Asp
    335                 340                 345

aag gtg aaa tct ggt gat acg atg aca gtg aat ata gat aag aat aca     1103
Lys Val Lys Ser Gly Asp Thr Met Thr Val Asn Ile Asp Lys Asn Thr
350                 355                 360                 365

gtt cca tca gat tta acc gat agt ttt gca ata cca aaa ata aaa gat     1151
Val Pro Ser Asp Leu Thr Asp Ser Phe Ala Ile Pro Lys Ile Lys Asp
                370                 375                 380

aat tct gga gaa atc atc gct aca ggt act tat gac aac aca aat aaa     1199
Asn Ser Gly Glu Ile Ile Ala Thr Gly Thr Tyr Asp Asn Thr Asn Lys
            385                 390                 395

caa att acc tac act ttt aca gat tat gta gat aaa tat gaa aat att     1247
Gln Ile Thr Tyr Thr Phe Thr Asp Tyr Val Asp Lys Tyr Glu Asn Ile
        400                 405                 410
```

-continued

```
aaa gcg cac ctt aaa tta aca tca tac att gat aaa tca aag gtt cca      1295
Lys Ala His Leu Lys Leu Thr Ser Tyr Ile Asp Lys Ser Lys Val Pro
    415                 420                 425

aat aat aac act aag tta gat gta gaa tat aag acg gcc ctt tca tca      1343
Asn Asn Asn Thr Lys Leu Asp Val Glu Tyr Lys Thr Ala Leu Ser Ser
430                 435                 440                 445

gta aat aaa aca att acg gtt gaa tat caa aaa cct aac gaa aat cgg      1391
Val Asn Lys Thr Ile Thr Val Glu Tyr Gln Lys Pro Asn Glu Asn Arg
                450                 455                 460

act gct aac ctt caa agt atg ttc aca aac ata gat acg aaa aac cat      1439
Thr Ala Asn Leu Gln Ser Met Phe Thr Asn Ile Asp Thr Lys Asn His
            465                 470                 475

aca gtt gag caa acg att tat att aac cct ctt cgt tat tca gcc aaa      1487
Thr Val Glu Gln Thr Ile Tyr Ile Asn Pro Leu Arg Tyr Ser Ala Lys
        480                 485                 490

gaa aca aat gta aat att tca ggg aat ggc gat gaa ggt tca aca att      1535
Glu Thr Asn Val Asn Ile Ser Gly Asn Gly Asp Glu Gly Ser Thr Ile
    495                 500                 505

atc gac gat agt aca atc att aaa gtt tat aag gtt gga gat aat caa      1583
Ile Asp Asp Ser Thr Ile Ile Lys Val Tyr Lys Val Gly Asp Asn Gln
510                 515                 520                 525

aat tta cca gat agt aac aga att tat gat tac agt gaa tat gaa gat      1631
Asn Leu Pro Asp Ser Asn Arg Ile Tyr Asp Tyr Ser Glu Tyr Glu Asp
                530                 535                 540

gtc aca aat gat gat tat gcc caa tta gga aat aat aat gac gtg aat      1679
Val Thr Asn Asp Asp Tyr Ala Gln Leu Gly Asn Asn Asn Asp Val Asn
            545                 550                 555

att aat ttt ggt aat ata gat tca cca tat att att aaa gtt att agt      1727
Ile Asn Phe Gly Asn Ile Asp Ser Pro Tyr Ile Ile Lys Val Ile Ser
        560                 565                 570

aaa tat gac cct aat aag gac gat tac acg acg ata cag caa act gtg      1775
Lys Tyr Asp Pro Asn Lys Asp Asp Tyr Thr Thr Ile Gln Gln Thr Val
    575                 580                 585

aca atg caa acg act ata aat gag tat act ggt gag ttt aga aca gca      1823
Thr Met Gln Thr Thr Ile Asn Glu Tyr Thr Gly Glu Phe Arg Thr Ala
590                 595                 600                 605

tcc tat gat aat aca att gct ttc tct aca agt tca ggt caa gga caa      1871
Ser Tyr Asp Asn Thr Ile Ala Phe Ser Thr Ser Ser Gly Gln Gly Gln
                610                 615                 620

ggt gac ttg cct cct gaa aaa act tat aaa atc gga gat tac gta tgg      1919
Gly Asp Leu Pro Pro Glu Lys Thr Tyr Lys Ile Gly Asp Tyr Val Trp
            625                 630                 635

gaa gat gta gat aaa gat ggt att caa aat aca aat gat aat gaa aaa      1967
Glu Asp Val Asp Lys Asp Gly Ile Gln Asn Thr Asn Asp Asn Glu Lys
        640                 645                 650

ccg ctt agt aat gta ttg gta act ttg acg tat cct gat gga act tca      2015
Pro Leu Ser Asn Val Leu Val Thr Leu Thr Tyr Pro Asp Gly Thr Ser
    655                 660                 665

aaa tca gtc aga aca gat gaa gag ggg aaa tat caa ttt gat ggg tta      2063
Lys Ser Val Arg Thr Asp Glu Glu Gly Lys Tyr Gln Phe Asp Gly Leu
670                 675                 680                 685

aaa aac gga ttg act tat aaa att aca ttc gaa aca ccg gaa gga tat      2111
Lys Asn Gly Leu Thr Tyr Lys Ile Thr Phe Glu Thr Pro Glu Gly Tyr
                690                 695                 700

acg ccg acg ctt aaa cat tca gga aca aat cct gca cta gac tca gaa      2159
Thr Pro Thr Leu Lys His Ser Gly Thr Asn Pro Ala Leu Asp Ser Glu
            705                 710                 715

ggc aat tct gta tgg gta act att aac gga caa gac gat atg act att      2207
Gly Asn Ser Val Trp Val Thr Ile Asn Gly Gln Asp Asp Met Thr Ile
        720                 725                 730
```

-continued

```
gat agc gga ttt tat caa aca cct aaa tat agc tta ggg aac tat gta     2255
Asp Ser Gly Phe Tyr Gln Thr Pro Lys Tyr Ser Leu Gly Asn Tyr Val
    735                 740                 745

tgg tat gac act aat aaa gat ggt att caa ggt gat gat gaa aaa gga     2303
Trp Tyr Asp Thr Asn Lys Asp Gly Ile Gln Gly Asp Asp Glu Lys Gly
750                 755                 760                 765

atc tct gga gta aaa gtg acg tta aaa gat gaa aac gga aat atc att     2351
Ile Ser Gly Val Lys Val Thr Leu Lys Asp Glu Asn Gly Asn Ile Ile
                770                 775                 780

agt aca aca aca act gat gaa aat gga aag tat caa ttt gat aat tta     2399
Ser Thr Thr Thr Thr Asp Glu Asn Gly Lys Tyr Gln Phe Asp Asn Leu
            785                 790                 795

aat agt ggt aat tat att gtt cat ttt gat aaa cct tca ggt atg act     2447
Asn Ser Gly Asn Tyr Ile Val His Phe Asp Lys Pro Ser Gly Met Thr
        800                 805                 810

caa aca aca aca gat tct ggt gat gat gac gaa cag gat gct gat ggg     2495
Gln Thr Thr Thr Asp Ser Gly Asp Asp Asp Glu Gln Asp Ala Asp Gly
    815                 820                 825

gaa gaa gtc cat gta aca att act gat cat gat gac ttt agt ata gat     2543
Glu Glu Val His Val Thr Ile Thr Asp His Asp Asp Phe Ser Ile Asp
830                 835                 840                 845

aac gga tac tat gat gac gac tca gat tca gat agt gat tca gac tca     2591
Asn Gly Tyr Tyr Asp Asp Asp Ser Asp Ser Asp Ser Asp Ser Asp Ser
                850                 855                 860

gat agc gac gac tca gac tcc gat agc gat tcc gac tca gac agc gac     2639
Asp Ser Asp Asp Ser Asp Ser Asp Ser Asp Ser Asp Ser Asp Ser Asp
            865                 870                 875

tca gat tcc gat agt gat tca gat tca gac agt gac tca gac tca gat     2687
Ser Asp Ser Asp Ser Asp Ser Asp Ser Asp Ser Asp Ser Asp Ser Asp
        880                 885                 890

agt gat tca gat tca gac agc gat tcc gac tca gac agt gac tca gga     2735
Ser Asp Ser Asp Ser Asp Ser Asp Ser Asp Ser Asp Ser Asp Ser Gly
    895                 900                 905

tta gac aat agc tca gat aag aat aca aaa gat aaa tta ccg gat aca     2783
Leu Asp Asn Ser Ser Asp Lys Asn Thr Lys Asp Lys Leu Pro Asp Thr
910                 915                 920                 925

gga gct aat gaa gat cat gat tct aaa ggc aca tta ctt gga gct tta     2831
Gly Ala Asn Glu Asp His Asp Ser Lys Gly Thr Leu Leu Gly Ala Leu
                930                 935                 940

ttt gca ggt tta gga gcg tta tta tta ggg aag cgt cgc aaa aat aga     2879
Phe Ala Gly Leu Gly Ala Leu Leu Leu Gly Lys Arg Arg Lys Asn Arg
            945                 950                 955

aaa aat aaa aat taa att att caa atg aaa tta gtg aaa gaa gca gat     2927
Lys Asn Lys Asn     Ile Ile Gln Met Lys Leu Val Lys Glu Ala Asp
        960                 965                 970

acg aca ttt gaa tag aaa gta tat tta gtc caa caa ata taa ggt gtt g   2976
Thr Thr Phe Glu     Lys Val Tyr Leu Val Gln Gln Ile     Gly Val
        975                 980                 985
```

<210> SEQ ID NO 8
<211> LENGTH: 13
<212> TYPE: PRT
<213> ORGANISM: Staphylococcus epidermidis

<400> SEQUENCE: 8

```
Ile Ala Lys Lys Thr Tyr Ile Leu Tyr Cys Ile Leu Leu
1               5                   10
```

<210> SEQ ID NO 9
<211> LENGTH: 18

-continued

<212> TYPE: PRT
<213> ORGANISM: Staphylococcus epidermidis

<400> SEQUENCE: 9

```
Lys Arg Phe Leu Leu Glu Asn Tyr Ile Glu Ile Val Lys Asp Lys Glu
1               5                   10                  15

Phe Leu
```

<210> SEQ ID NO 10
<211> LENGTH: 930
<212> TYPE: PRT
<213> ORGANISM: Staphylococcus epidermidis

<400> SEQUENCE: 10

```
Leu Lys Lys Asn Asn Leu Leu Thr Lys Lys Lys Pro Ile Ala Asn Lys
1               5                   10                  15

Ser Asn Lys Tyr Ala Ile Arg Lys Phe Thr Val Gly Thr Ala Ser Ile
            20                  25                  30

Val Ile Gly Ala Ala Leu Leu Phe Gly Leu Gly His Asn Glu Ala Lys
        35                  40                  45

Ala Glu Glu Asn Thr Val Gln Asp Val Lys Asp Ser Asn Met Asp Asp
    50                  55                  60

Glu Leu Ser Asp Ser Asn Asp Gln Ser Ser Asn Glu Glu Lys Asn Asp
65                  70                  75                  80

Val Ile Asn Asn Ser Gln Ser Ile Asn Thr Asp Asp Asp Asn Gln Ile
                85                  90                  95

Lys Lys Glu Glu Thr Asn Ser Asn Asp Ala Ile Glu Asn Arg Ser Lys
            100                 105                 110

Asp Ile Thr Gln Ser Thr Thr Asn Val Asp Glu Asn Glu Ala Thr Phe
        115                 120                 125

Leu Gln Lys Thr Pro Gln Asp Asn Thr Gln Leu Lys Glu Glu Val Val
    130                 135                 140

Lys Glu Pro Ser Ser Val Glu Ser Ser Asn Ser Ser Met Asp Thr Ala
145                 150                 155                 160

Gln Gln Pro Ser His Thr Thr Ile Asn Ser Glu Ala Ser Ile Gln Thr
                165                 170                 175

Ser Asp Asn Glu Glu Asn Ser Arg Val Ser Asp Phe Ala Asn Ser Lys
            180                 185                 190

Ile Ile Glu Ser Asn Thr Glu Ser Asn Lys Glu Glu Asn Thr Ile Glu
        195                 200                 205

Gln Pro Asn Lys Val Arg Glu Asp Ser Ile Thr Ser Gln Pro Ser Ser
    210                 215                 220

Tyr Lys Asn Ile Asp Glu Lys Ile Ser Asn Gln Asp Glu Leu Leu Asn
225                 230                 235                 240

Leu Pro Ile Asn Glu Tyr Glu Asn Lys Val Arg Pro Leu Ser Thr Thr
                245                 250                 255

Ser Ala Gln Pro Ser Ser Lys Arg Val Thr Val Asn Gln Leu Ala Ala
            260                 265                 270

Glu Gln Gly Ser Asn Val Asn His Leu Ile Lys Val Thr Asp Gln Ser
        275                 280                 285

Ile Thr Glu Gly Tyr Asp Asp Ser Asp Gly Ile Ile Lys Ala His Asp
    290                 295                 300

Ala Glu Asn Leu Ile Tyr Asp Val Thr Phe Glu Val Asp Asp Lys Val
305                 310                 315                 320

Lys Ser Gly Asp Thr Met Thr Val Asn Ile Asp Lys Asn Thr Val Pro
```

-continued

```
                325                 330                 335

Ser Asp Leu Thr Asp Ser Phe Ala Ile Pro Lys Ile Lys Asp Asn Ser
            340                 345                 350

Gly Glu Ile Ile Ala Thr Gly Thr Tyr Asp Asn Thr Asn Lys Gln Ile
        355                 360                 365

Thr Tyr Thr Phe Thr Asp Tyr Val Asp Lys Tyr Glu Asn Ile Lys Ala
    370                 375                 380

His Leu Lys Leu Thr Ser Tyr Ile Asp Lys Ser Lys Val Pro Asn Asn
385                 390                 395                 400

Asn Thr Lys Leu Asp Val Glu Tyr Lys Thr Ala Leu Ser Ser Val Asn
                405                 410                 415

Lys Thr Ile Thr Val Glu Tyr Gln Lys Pro Asn Glu Asn Arg Thr Ala
            420                 425                 430

Asn Leu Gln Ser Met Phe Thr Asn Ile Asp Thr Lys Asn His Thr Val
        435                 440                 445

Glu Gln Thr Ile Tyr Ile Asn Pro Leu Arg Tyr Ser Ala Lys Glu Thr
    450                 455                 460

Asn Val Asn Ile Ser Gly Asn Gly Asp Glu Gly Ser Thr Ile Ile Asp
465                 470                 475                 480

Asp Ser Thr Ile Ile Lys Val Tyr Lys Val Gly Asp Asn Gln Asn Leu
                485                 490                 495

Pro Asp Ser Asn Arg Ile Tyr Asp Tyr Ser Glu Tyr Glu Asp Val Thr
            500                 505                 510

Asn Asp Asp Tyr Ala Gln Leu Gly Asn Asn Asn Asp Val Asn Ile Asn
        515                 520                 525

Phe Gly Asn Ile Asp Ser Pro Tyr Ile Ile Lys Val Ile Ser Lys Tyr
    530                 535                 540

Asp Pro Asn Lys Asp Asp Tyr Thr Thr Ile Gln Gln Thr Val Thr Met
545                 550                 555                 560

Gln Thr Thr Ile Asn Glu Tyr Thr Gly Glu Phe Arg Thr Ala Ser Tyr
                565                 570                 575

Asp Asn Thr Ile Ala Phe Ser Thr Ser Ser Gly Gln Gly Gln Gly Asp
            580                 585                 590

Leu Pro Pro Glu Lys Thr Tyr Lys Ile Gly Asp Tyr Val Trp Glu Asp
        595                 600                 605

Val Asp Lys Asp Gly Ile Gln Asn Thr Asn Asp Asn Glu Lys Pro Leu
    610                 615                 620

Ser Asn Val Leu Val Thr Leu Thr Tyr Pro Asp Gly Thr Ser Lys Ser
625                 630                 635                 640

Val Arg Thr Asp Glu Glu Gly Lys Tyr Gln Phe Asp Gly Leu Lys Asn
                645                 650                 655

Gly Leu Thr Tyr Lys Ile Thr Phe Glu Thr Pro Glu Gly Tyr Thr Pro
            660                 665                 670

Thr Leu Lys His Ser Gly Thr Asn Pro Ala Leu Asp Ser Glu Gly Asn
        675                 680                 685

Ser Val Trp Val Thr Ile Asn Gly Gln Asp Asp Met Thr Ile Asp Ser
    690                 695                 700

Gly Phe Tyr Gln Thr Pro Lys Tyr Ser Leu Gly Asn Tyr Val Trp Tyr
705                 710                 715                 720

Asp Thr Asn Lys Asp Gly Ile Gln Gly Asp Asp Glu Lys Gly Ile Ser
                725                 730                 735

Gly Val Lys Val Thr Leu Lys Asp Glu Asn Gly Asn Ile Ile Ser Thr
            740                 745                 750
```

-continued

```
Thr Thr Thr Asp Glu Asn Gly Lys Tyr Gln Phe Asp Asn Leu Asn Ser
        755                 760                 765

Gly Asn Tyr Ile Val His Phe Asp Lys Pro Ser Gly Met Thr Gln Thr
    770                 775                 780

Thr Thr Asp Ser Gly Asp Asp Asp Glu Gln Asp Ala Asp Gly Glu Glu
785                 790                 795                 800

Val His Val Thr Ile Thr Asp His Asp Asp Phe Ser Ile Asp Asn Gly
                805                 810                 815

Tyr Tyr Asp Asp Asp Ser Asp Ser Asp Ser Asp Ser Asp Ser Asp Ser
            820                 825                 830

Asp Asp Ser Asp Ser Asp Ser Asp Ser Asp Ser Asp Ser Asp Ser Asp
        835                 840                 845

Ser Asp Ser Asp Ser Asp Ser Asp Ser Asp Ser Asp Ser Asp Ser Asp
    850                 855                 860

Ser Asp Ser Asp Ser Asp Ser Asp Ser Asp Ser Asp Ser Gly Leu Asp
865                 870                 875                 880

Asn Ser Ser Asp Lys Asn Thr Lys Asp Lys Leu Pro Asp Thr Gly Ala
                885                 890                 895

Asn Glu Asp His Asp Ser Lys Gly Thr Leu Leu Gly Ala Leu Phe Ala
            900                 905                 910

Gly Leu Gly Ala Leu Leu Leu Gly Lys Arg Arg Lys Asn Arg Lys Asn
        915                 920                 925

Lys Asn
    930


<210> SEQ ID NO 11
<211> LENGTH: 15
<212> TYPE: PRT
<213> ORGANISM: Staphylococcus epidermidis

<400> SEQUENCE: 11

Ile Ile Gln Met Lys Leu Val Lys Glu Ala Asp Thr Thr Phe Glu
1               5                   10                  15


<210> SEQ ID NO 12
<211> LENGTH: 8
<212> TYPE: PRT
<213> ORGANISM: Staphylococcus epidermidis

<400> SEQUENCE: 12

Lys Val Tyr Leu Val Gln Gln Ile
1               5


<210> SEQ ID NO 13
<211> LENGTH: 1464
<212> TYPE: DNA
<213> ORGANISM: Staphylococcus epidermidis
<220> FEATURE:
<221> NAME/KEY: CDS
<222> LOCATION: (1)..(1464)

<400> SEQUENCE: 13

atg aaa aag ttt aac att aaa cat tca ttt atg ctt acg ggc ttt gct       48
Met Lys Lys Phe Asn Ile Lys His Ser Phe Met Leu Thr Gly Phe Ala
1               5                   10                  15

ttc atg gta act aca tca tta ttc agt cac caa gca cat gct gaa ggt       96
Phe Met Val Thr Thr Ser Leu Phe Ser His Gln Ala His Ala Glu Gly
            20                  25                  30

aat cat cct att gac att aat ttt tct aaa gat caa att gat aga aat      144
```

-continued

```
Asn His Pro Ile Asp Ile Asn Phe Ser Lys Asp Gln Ile Asp Arg Asn
        35                  40                  45

aca gct aag agc aat att atc aat cga gtg aat gac act agt cgc aca      192
Thr Ala Lys Ser Asn Ile Ile Asn Arg Val Asn Asp Thr Ser Arg Thr
    50                  55                  60

gga att agt atg aat tcg gat aat gat tta gat aca gat atc gtt tca      240
Gly Ile Ser Met Asn Ser Asp Asn Asp Leu Asp Thr Asp Ile Val Ser
65                  70                  75                  80

aat agt gac tca gaa aat gac aca tat tta gat agt gat tca gat tca      288
Asn Ser Asp Ser Glu Asn Asp Thr Tyr Leu Asp Ser Asp Ser Asp Ser
                85                  90                  95

gac agt gac tca gat tca gat agt gac tca gat tca gat agt gac tca      336
Asp Ser Asp Ser Asp Ser Asp Ser Asp Ser Asp Ser Asp Ser Asp Ser
            100                 105                 110

gat tca gat agt gac tca gat tca gac agt gat tca gac tca gat agt      384
Asp Ser Asp Ser Asp Ser Asp Ser Asp Ser Asp Ser Asp Ser Asp Ser
        115                 120                 125

gac tca gat tca gac agt gat tca gac tca gat agt gat tca gat tca      432
Asp Ser Asp Ser Asp Ser Asp Ser Asp Ser Asp Ser Asp Ser Asp Ser
    130                 135                 140

gac agt gat tca gat tca gac agt gac tca gac tca gac agt gat tca      480
Asp Ser Asp Ser Asp Ser Asp Ser Asp Ser Asp Ser Asp Ser Asp Ser
145                 150                 155                 160

gat tca gat agt gat tca gat tca gat agt gat tca gat tca gat agt      528
Asp Ser Asp Ser Asp Ser Asp Ser Asp Ser Asp Ser Asp Ser Asp Ser
                165                 170                 175

gat tca gat tca gac agt gac tca gac tca gac agt gat tca gat tca      576
Asp Ser Asp Ser Asp Ser Asp Ser Asp Ser Asp Ser Asp Ser Asp Ser
            180                 185                 190

gat agt gat tca gac tca gat agt gac tca gat tca gat agt gat tca      624
Asp Ser Asp Ser Asp Ser Asp Ser Asp Ser Asp Ser Asp Ser Asp Ser
        195                 200                 205

gac tct ggt aca agt tca ggt aag ggt tca cat acc gga aaa aaa cct      672
Asp Ser Gly Thr Ser Ser Gly Lys Gly Ser His Thr Gly Lys Lys Pro
    210                 215                 220

ggt aac cct aaa gga aat aca aat aga cct tct caa aga cat acg aat      720
Gly Asn Pro Lys Gly Asn Thr Asn Arg Pro Ser Gln Arg His Thr Asn
225                 230                 235                 240

caa ccc caa agg cct aaa tac aat caa aca aat caa aac aat ata aac      768
Gln Pro Gln Arg Pro Lys Tyr Asn Gln Thr Asn Gln Asn Asn Ile Asn
                245                 250                 255

aat ata aac cat aat att aat cat aca cgt act agt gga gat ggt gcg      816
Asn Ile Asn His Asn Ile Asn His Thr Arg Thr Ser Gly Asp Gly Ala
            260                 265                 270

cct ttt aaa cgt caa caa aat att att aat tct aat tca ggt cat aga      864
Pro Phe Lys Arg Gln Gln Asn Ile Ile Asn Ser Asn Ser Gly His Arg
        275                 280                 285

aat caa aat aat ata aat caa ttt ata tgg aac aaa aat ggc ttt ttt      912
Asn Gln Asn Asn Ile Asn Gln Phe Ile Trp Asn Lys Asn Gly Phe Phe
    290                 295                 300

aaa tct caa aat aat acc gaa cat aga atg aat agt agc gat aat acc      960
Lys Ser Gln Asn Asn Thr Glu His Arg Met Asn Ser Ser Asp Asn Thr
305                 310                 315                 320

aat tca tta att agc aga ttc aga caa tta gcc acg ggt gct tat aag     1008
Asn Ser Leu Ile Ser Arg Phe Arg Gln Leu Ala Thr Gly Ala Tyr Lys
                325                 330                 335

tac aat ccg ttt ttg att aat caa gta aaa aat ttg aat caa tta gat     1056
Tyr Asn Pro Phe Leu Ile Asn Gln Val Lys Asn Leu Asn Gln Leu Asp
            340                 345                 350
```

-continued

```
gga aag gtg aca gat agt gac att tat agc ttg ttt aga aag caa tca      1104
Gly Lys Val Thr Asp Ser Asp Ile Tyr Ser Leu Phe Arg Lys Gln Ser
        355                 360                 365

ttt aga gga aat gaa tat tta aat tca tta caa aaa ggg aca agc tat      1152
Phe Arg Gly Asn Glu Tyr Leu Asn Ser Leu Gln Lys Gly Thr Ser Tyr
    370                 375                 380

ttc aga ttt caa tat ttt aat cca ctt aat tct agt aaa tac tat gaa      1200
Phe Arg Phe Gln Tyr Phe Asn Pro Leu Asn Ser Ser Lys Tyr Tyr Glu
385                 390                 395                 400

aat tta gat gat cag gtt tta gct tta att aca gga gaa atc ggc tca      1248
Asn Leu Asp Asp Gln Val Leu Ala Leu Ile Thr Gly Glu Ile Gly Ser
                405                 410                 415

atg cca gaa ctt aaa aaa cct acg gat aaa gaa gat aaa aat cat agc      1296
Met Pro Glu Leu Lys Lys Pro Thr Asp Lys Glu Asp Lys Asn His Ser
            420                 425                 430

gcc ttc aaa aac cat agt gca gat gag ata aca aca aat aat gat gga      1344
Ala Phe Lys Asn His Ser Ala Asp Glu Ile Thr Thr Asn Asn Asp Gly
        435                 440                 445

cac tcc aaa gat tat gat aag aaa aag aaa ata cat cga agt ctt tta      1392
His Ser Lys Asp Tyr Asp Lys Lys Lys Lys Ile His Arg Ser Leu Leu
    450                 455                 460

tcg tta agt att gca ata att gga att ttt cta gga gtc act gga cta      1440
Ser Leu Ser Ile Ala Ile Ile Gly Ile Phe Leu Gly Val Thr Gly Leu
465                 470                 475                 480

tat atc ttt aga aga aaa aag taa                                      1464
Tyr Ile Phe Arg Arg Lys Lys
                485


<210> SEQ ID NO 14
<211> LENGTH: 487
<212> TYPE: PRT
<213> ORGANISM: Staphylococcus epidermidis

<400> SEQUENCE: 14

Met Lys Lys Phe Asn Ile Lys His Ser Phe Met Leu Thr Gly Phe Ala
1               5                   10                  15

Phe Met Val Thr Thr Ser Leu Phe Ser His Gln Ala His Ala Glu Gly
            20                  25                  30

Asn His Pro Ile Asp Ile Asn Phe Ser Lys Asp Gln Ile Asp Arg Asn
        35                  40                  45

Thr Ala Lys Ser Asn Ile Ile Asn Arg Val Asn Asp Thr Ser Arg Thr
    50                  55                  60

Gly Ile Ser Met Asn Ser Asp Asn Asp Leu Asp Thr Asp Ile Val Ser
65                  70                  75                  80

Asn Ser Asp Ser Glu Asn Asp Thr Tyr Leu Asp Ser Asp Ser Asp Ser
                85                  90                  95

Asp Ser Asp Ser Asp Ser Asp Ser Asp Ser Asp Ser Asp Ser Asp Ser
            100                 105                 110

Asp Ser Asp Ser Asp Ser Asp Ser Asp Ser Asp Ser Asp Ser Asp Ser
        115                 120                 125

Asp Ser Asp Ser Asp Ser Asp Ser Asp Ser Asp Ser Asp Ser Asp Ser
    130                 135                 140

Asp Ser Asp Ser Asp Ser Asp Ser Asp Ser Asp Ser Asp Ser Asp Ser
145                 150                 155                 160

Asp Ser Asp Ser Asp Ser Asp Ser Asp Ser Asp Ser Asp Ser Asp Ser
                165                 170                 175

Asp Ser Asp Ser Asp Ser Asp Ser Asp Ser Asp Ser Asp Ser Asp Ser
            180                 185                 190
```

-continued

```
Asp Ser Asp Ser Asp Ser Asp Ser Asp Ser Asp Ser Asp Ser Asp Ser
        195                 200                 205

Asp Ser Gly Thr Ser Ser Gly Lys Gly Ser His Thr Gly Lys Lys Pro
    210                 215                 220

Gly Asn Pro Lys Gly Asn Thr Asn Arg Pro Ser Gln Arg His Thr Asn
225                 230                 235                 240

Gln Pro Gln Arg Pro Lys Tyr Asn Gln Thr Asn Gln Asn Asn Ile Asn
                245                 250                 255

Asn Ile Asn His Asn Ile Asn His Thr Arg Thr Ser Gly Asp Gly Ala
            260                 265                 270

Pro Phe Lys Arg Gln Gln Asn Ile Ile Asn Ser Asn Ser Gly His Arg
        275                 280                 285

Asn Gln Asn Asn Ile Asn Gln Phe Ile Trp Asn Lys Asn Gly Phe Phe
    290                 295                 300

Lys Ser Gln Asn Asn Thr Glu His Arg Met Asn Ser Ser Asp Asn Thr
305                 310                 315                 320

Asn Ser Leu Ile Ser Arg Phe Arg Gln Leu Ala Thr Gly Ala Tyr Lys
                325                 330                 335

Tyr Asn Pro Phe Leu Ile Asn Gln Val Lys Asn Leu Asn Gln Leu Asp
            340                 345                 350

Gly Lys Val Thr Asp Ser Asp Ile Tyr Ser Leu Phe Arg Lys Gln Ser
        355                 360                 365

Phe Arg Gly Asn Glu Tyr Leu Asn Ser Leu Gln Lys Gly Thr Ser Tyr
    370                 375                 380

Phe Arg Phe Gln Tyr Phe Asn Pro Leu Asn Ser Ser Lys Tyr Tyr Glu
385                 390                 395                 400

Asn Leu Asp Asp Gln Val Leu Ala Leu Ile Thr Gly Glu Ile Gly Ser
                405                 410                 415

Met Pro Glu Leu Lys Lys Pro Thr Asp Lys Glu Asp Lys Asn His Ser
            420                 425                 430

Ala Phe Lys Asn His Ser Ala Asp Glu Ile Thr Thr Asn Asn Asp Gly
        435                 440                 445

His Ser Lys Asp Tyr Asp Lys Lys Lys Lys Ile His Arg Ser Leu Leu
    450                 455                 460

Ser Leu Ser Ile Ala Ile Ile Gly Ile Phe Leu Gly Val Thr Gly Leu
465                 470                 475                 480

Tyr Ile Phe Arg Arg Lys Lys
                485


<210> SEQ ID NO 15
<211> LENGTH: 18
<212> TYPE: DNA
<213> ORGANISM: Staphylococcus epidermidis
<220> FEATURE:
<221> NAME/KEY: misc_feature
<222> LOCATION: (6)..()
<223> OTHER INFORMATION: n=(a or c or t or g)
<221> NAME/KEY: misc_feature
<222> LOCATION: (12)..()
<223> OTHER INFORMATION: n=(a or c or t or g)

<400> SEQUENCE: 15

gaytcngayt cngayagy                                                18


<210> SEQ ID NO 16
<211> LENGTH: 9
<212> TYPE: PRT
```

-continued

<213> ORGANISM: Staphylococcus epidermidis

<400> SEQUENCE: 16

Thr Tyr Thr Phe Thr Asp Tyr Val Asp
1               5

<210> SEQ ID NO 17
<211> LENGTH: 5
<212> TYPE: PRT
<213> ORGANISM: Staphylococcus epidermidis
<220> FEATURE:
<221> NAME/KEY: UNSURE
<222> LOCATION: (3)..(3)
<223> OTHER INFORMATION: Xaa can be any amino acid

<400> SEQUENCE: 17

Leu Pro Xaa Thr Gly
1               5

<210> SEQ ID NO 18
<211> LENGTH: 60
<212> TYPE: PRT
<213> ORGANISM: Staphylococcus epidermidis

<400> SEQUENCE: 18

Ser Asp Ser Asp Ser Asp Ser Asp Ser Asp Ser Asp Ser Asp Lys Asn
1               5                   10                  15

Ala Lys Asp Lys Leu Pro Asp Thr Gly Ala Asn Glu Asp His Asp Ser
            20                  25                  30

Lys Gly Thr Leu Leu Gly Thr Leu Phe Ala Gly Leu Gly Ala Leu Leu
        35                  40                  45

Leu Gly Arg Arg Arg Lys Lys Asp Asn Lys Glu Lys
    50                  55                  60

<210> SEQ ID NO 19
<211> LENGTH: 60
<212> TYPE: PRT
<213> ORGANISM: Staphylococcus epidermidis

<400> SEQUENCE: 19

Ser Asp Ser Asp Ser Asp Ser Gly Leu Asp Asn Ser Ser Asp Lys Asn
1               5                   10                  15

Thr Lys Asp Lys Leu Pro Asp Thr Gly Ala Asn Glu Asp His Asp Ser
            20                  25                  30

Lys Gly Thr Leu Leu Gly Ala Leu Phe Ala Gly Leu Gly Ala Leu Leu
        35                  40                  45

Leu Gly Lys Arg Arg Lys Asn Arg Lys Asn Lys Asn
    50                  55                  60

<210> SEQ ID NO 20
<211> LENGTH: 60
<212> TYPE: PRT
<213> ORGANISM: Staphylococcus epidermidis

<400> SEQUENCE: 20

Asp Lys Asn His Ser Ala Phe Lys Asn His Ser Ala Asp Glu Ile Thr
1               5                   10                  15

Thr Asn Asn Asp Gly His Ser Lys Asp Tyr Asp Lys Lys Lys Lys Ile
            20                  25                  30

His Arg Ser Leu Leu Ser Leu Ser Ile Ala Ile Ile Gly Ile Phe Leu
        35                  40                  45

-continued

```
Gly Val Thr Gly Leu Tyr Ile Phe Arg Arg Lys Lys
    50                  55                  60


<210> SEQ ID NO 21
<211> LENGTH: 18
<212> TYPE: DNA
<213> ORGANISM: Staphylococcus epidermidis

<400> SEQUENCE: 21

gatgatgaat tatcagac                                                    18


<210> SEQ ID NO 22
<211> LENGTH: 19
<212> TYPE: DNA
<213> ORGANISM: Staphylococcus epidermidis

<400> SEQUENCE: 22

caggaggcaa gtcaccttg                                                   19


<210> SEQ ID NO 23
<211> LENGTH: 27
<212> TYPE: DNA
<213> ORGANISM: Staphylococcus epidermidis

<400> SEQUENCE: 23

gccggatccc caattccaga ggattca                                          27


<210> SEQ ID NO 24
<211> LENGTH: 27
<212> TYPE: DNA
<213> ORGANISM: Staphylococcus epidermidis

<400> SEQUENCE: 24

gccaagctta ttgttagaac ctgactc                                          27


<210> SEQ ID NO 25
<211> LENGTH: 17
<212> TYPE: DNA
<213> ORGANISM: Staphylococcus epidermidis

<400> SEQUENCE: 25

gattcagata gccattc                                                     17


<210> SEQ ID NO 26
<211> LENGTH: 17
<212> TYPE: DNA
<213> ORGANISM: Staphylococcus epidermidis

<400> SEQUENCE: 26

ctgagtcact gtctgag                                                     17


<210> SEQ ID NO 27
<211> LENGTH: 28
<212> TYPE: DNA
<213> ORGANISM: Staphylococcus epidermidis

<400> SEQUENCE: 27

cccggatccg ctgaagacaa tcaattag                                         28


<210> SEQ ID NO 28
<211> LENGTH: 27
<212> TYPE: DNA
<213> ORGANISM: Staphylococcus epidermidis
```

-continued

<400> SEQUENCE: 28
cccaagctta attatccccc tgtgctg 27

<210> SEQ ID NO 29
<211> LENGTH: 31
<212> TYPE: DNA
<213> ORGANISM: Staphylococcus epidermidis

<400> SEQUENCE: 29
cccggatccg aggagaatac agtacaagac g 31

<210> SEQ ID NO 30
<211> LENGTH: 33
<212> TYPE: DNA
<213> ORGANISM: Staphylococcus epidermidis

<400> SEQUENCE: 30
cccggtacct agtttttcag gaggcaagtc acc 33

<210> SEQ ID NO 31
<211> LENGTH: 30
<212> TYPE: DNA
<213> ORGANISM: Staphylococcus epidermidis

<400> SEQUENCE: 31
cccggatccg aaggtaatca tcctattgac 30

<210> SEQ ID NO 32
<211> LENGTH: 37
<212> TYPE: DNA
<213> ORGANISM: Staphylococcus epidermidis

<400> SEQUENCE: 32
cccaagctta ctttttcttt ctaaagatat atagtcc 37

<210> SEQ ID NO 33
<211> LENGTH: 30
<212> TYPE: DNA
<213> ORGANISM: Staphylococcus epidermidis

<400> SEQUENCE: 33
cccgaattca attatccccc tgtgctgttg 30

<210> SEQ ID NO 34
<211> LENGTH: 33
<212> TYPE: DNA
<213> ORGANISM: Staphylococcus epidermidis

<400> SEQUENCE: 34
cccgaattct agtttttcag gaggcaagtc acc 33

<210> SEQ ID NO 35
<211> LENGTH: 28
<212> TYPE: DNA
<213> ORGANISM: Staphylococcus epidermidis

<400> SEQUENCE: 35
ggcggatccg aaggtaatca tcctattg 28

<210> SEQ ID NO 36
<211> LENGTH: 28
<212> TYPE: DNA
<213> ORGANISM: Staphylococcus epidermidis -continued

```
<400> SEQUENCE: 36

ggcaagcttc taaatatgtg tcattttc                                        28


<210> SEQ ID NO 37
<211> LENGTH: 4
<212> TYPE: PRT
<213> ORGANISM: Staphylococcus epidermidis

<400> SEQUENCE: 37

Gly Gly Ala Gly
1


<210> SEQ ID NO 38
<211> LENGTH: 13
<212> TYPE: PRT
<213> ORGANISM: Staphylococcus epidermidis

<400> SEQUENCE: 38

Asp Tyr Ser Glu Tyr Glu Asp Val Thr Asn Asp Asp Tyr
1               5                   10
```

POLYPEPTIDES AND POLYNUCLEOTIDES FROM COAGULASE-NEGATIVE STAPHYLOCOCCI

CROSS-REFERENCE TO RELATED APPLICATIONS

The present application claims the benefit of U.S. Provisional Applications Ser. No. 60/117,119, filed Jan. 25, 1999, and Ser. No. 60/098,443, filed Aug. 31, 1998.

FIELD OF THE INVENTION

The present invention is in the fields of microbiology and molecular biology and more particularly is in the field of biological products for the prevention, treatment or diagnosis of coagulase negative staphylococcal infections in man and animals.

BACKGROUND OF THE INVENTION

Staphylococci are Gram-positive spherical cells, usually arranged in grape-like irregular clusters. Some are members of the normal flora of the skin and mucous membranes of humans, others cause suppuration, abscess formation, a variety of pyogenic infections, and even fatal septicemia. Pathogenic staphylococci often hemolyze blood, coagulate plasma, and produce a variety of extracellular enzymes and toxins. The most common type of food poisoning is caused by a heat-stable staphylococcal enterotoxin. The genus Staphylococcus has at least 30 species. The three main species of clinical importance are *Staphylococcus aureus, Staphylococcus epidermidis*, and *Staphylococcus saprophyticus. Staphylococcus aureus* is coagulase-positive, which differentiates it from the other species. *S. aureus* is a major pathogen for humans. Almost every person has some type of *S. aureus* infection during a lifetime, ranging in severity from food poisoning or minor skin infections to severe life-threatening infections.

The coagulase-negative staphylococci are normal human flora which sometimes cause infection, often associated with implanted devices especially in very young, old and immunocompromised patients. Approximately 75% of the infections caused by coagulase-negative staphylococci are due to *S. epidermidis*. Infections due to *Staphylococcus warneri, Staphylococcus hominis*, and other species are less common. *S. saprophyticus* is a relatively common cause of urinary tract infections in young women. The staphylococci produce catalase, which differentiates them from the streptococci.

Both *Staphylococcus aureus* and *Staphylococcus epidermidis* have a characteristic propensity for invading skin and adjacent tissues at the site of prosthetic medical devices, including intravascular catheters, cerebrospinal fluid shunts, hemodialysis shunts, vascular grafts, and extended wear contact lenses. Within 48 to 72 hours, relatively large numbers of staphylococci are demonstrable at the site of insertion of these foreign bodies. (Archer, G. L., in Remington, J. S., et al., Current Clinical Topics in Infectious Diseases, McGraw-Hill, New York, 25–46, 1986.)

*Staphylococcus epidermidis* is a generally avirulent commensal organism of the human skin, and is the principal etiologic agent of infections of peripheral and central venous catheters, prosthetic heart valves, artificial joints, and other prosthetic devices. It has been demonstrated that *S. epidermidis* cells attach and proliferate on the inner or outer surfaces of catheters, irrespective of their composition—whether polyethylene, polyvinylchloride, polyvinylfluoride or polyester based.

Initial localized infections of indwelling medical devices can lead to more serious invasive infections such as septicemia, osteomyelitis, and endocarditis. Vascular catheters are thought to become infected when microorganisms gain access to the device, and hence the bloodstream, by migration from the skin surface down the transcutaneous portion of the catheter. In infections associated with medical devices, plastic and metal surfaces become coated with host plasma and matrix proteins such as fibrinogen, vitronectin and fibronectin shortly after implantation. *S. epidermidis* bacteremia can result in an excess hospital stay of 8 days, which is quite expensive.

Although the virulence of coagulase-negative staphylococci is enhanced in the presence of a foreign body, the microbial factors that permit these normal skin commensals to become nosocomial pathogens have not been well characterized. The ability of coagulase-negative *S. epidermidis* to adhere to these proteins is of crucial importance for initiating infection. As adherence is believed to be the critical first step in the pathogenesis of coagulase-negative staphylococcal foreign-body infections, attention has focused on surface properties of these organisms that might mediate adherence to, and then colonization of, polymeric prosthetic materials.

A number of factors influence an organism's ability to adhere to prosthetic material. These include characteristics of the microorganism and the biomaterial, and the nature of the surrounding environment. The initial attraction between the organism and the host is influenced by nonspecific forces such as surface charge, polarity, Van der Waal forces and hydrophobic interactions. The critical stage of adherence involves specific interactions between cell surface adhesins and immobilized host proteins. To date, investigation concerning the adherence of *S. epidermidis* to biomaterials has concerned itself primarily with the role of the extracellular polysaccharide or glycocalyx, also known as slime. Despite intensive study, however, the proposed role of slime in the pathogenesis of disease or even its composition remain debated. (Drewry et al., *Clin. Microbiol* 28:1292–1296, 1990) Currently, extracellular slime is thought to play a role in the later stages of adherence and persistence of infection. It may serve as an ion exchange resin to optimize a local nutritional environment, prevent penetration of antibiotics into the macro-colony or protect bacteria from phagocytic host defense cells. Peters et al. have shown by electron microscopy studies that extracellular polysaccharide appears in the later stages of attachment and is not present during the initial phase of adherence. (*J. Infect. Dis*., 65146:479–482, 1982) Hogt et al. demonstrated that removal of the extracellular slime layer by repeated washing does not diminish the ability of *S. epidermidis* to adhere to biomaterials. (*J. Gen. Microbiol.* 129:2959–2968, 1983)

Thus far, study of exopolysaccharide has lent little to prevention of initial adherence by the bacteria. Several other studies have identified other potential adhesins of *S. epidermidis* including the polysaccharide adhesin (PS/A) observed by Tojo et al. (*J. Infect. Dis.* 157:713–722, 1988) and the slime associated antigen (SAA) of Christensen et al. (*Infect Immun*, 58:2906–2911, 1990).

It has been demonstrated that PS/A is a complex mixture of monosaccharide adhesins which blocks adherence of PS/A producing strains of *S. epidermidis.* In an animal model of endocarditis antibodies directed against PS/A were protective. However, it is not clear whether this protective effect was specific, related to anti-adhesive effects of the antibody or due to a more generalized increase in the efficiency of opsonophagocytosis of blood borne bacteria. It has been hypothesized that each adhesin functions in different stages of the adherence process with one or more of these adhesins responsible for initial attraction while others are needed for aggregation in the macro-colonies.

Despite many studies, factors involved in the initial adherence of *S. epidermidis* to biomaterials remain largely unknown. Further unknown is a practical method for preventing the first stage of infection, adherence or adhesion. Therefore, a great need remains for the discovery and characterization of bacterial adhesin proteins and the genes that encode them.

Accordingly, it is an object of the present invention to provide cell-wall associated extracellular matrix binding proteins of coagulase-negative staphylococci.

It is a further object of the present invention to provide coagulase-negative staphylococcal surface proteins that are able to inhibit staphylococcal adhesion to the immobilized extracellular matrix or host cells present on the surface of implanted biomaterials.

It is a further object of the present invention to provide a coagulase-negative staphylococci vaccine, to generate antisera and antibodies to coagulase-negative staphylococcal proteins, and to isolate antibodies to coagulase-negative staphylococci.

It is a further object of the present invention to provide improved materials and methods for detecting and differentiating coagulase-negative staphylococcal organisms in clinical and laboratory settings.

It is a further object of the invention to provide nucleic acid probes and primers specific for coagulase-negative staphylococci.

It is a further object of the invention to provide methods for detecting, diagnosing, treating or monitoring the progress of therapy for bacterial infections that are sensitive and specific for coagulase-negative staphylococci.

These and other objects, features and advantages of the present invention will become apparent after a-review of the following detailed description of the disclosed embodiments and the appended claims.

SUMMARY OF THE INVENTION

Isolated proteins from coagulase-negative staphylococci and their corresponding amino acid and nucleic acid sequences are provided. The proteins are designated SdrF, SdrG and SdrH. The DNA sequence of sdrF and the amino acid sequence of the protein SdrF (in bold) are shown in FIG. 2 along with their flanking sequences. The DNA sequence of sdrG and the amino acid sequence of the protein SdrG (in bold) are shown in FIG. 3 along with their flanking sequences. Finally, the SdrH coding region including DNA and amino acid sequence is shown in FIG. 4.

It has also been discovered that in the A region of SdrF and SdrG there is highly conserved amino acid sequence that can be used to derive a consensus TYTFTDYVD (SEQ ID NO:16) motif. The motif can be used in multicomponent vaccines to impart broad spectrum immunity to bacterial infections, and also can be used to produce monoclonal or polyclonal antibodies that impart broad spectrum passive immunity. In an alternative embodiment, any combination of the variable sequence motif derived from the Sdr protein family, (T) (Y) (T) (F) (T) (D/N) (Y) (V) (D), can be used to impart immunity or to induce protective antibodies. The proteins, or antigenic portions thereof, are used to produce antibodies for the diagnosis of coagulase-negative staphylococcal bacterial infections or for the development of anti-coagulase-negative staphylococcal vaccines for active or passive immunization. When administered to a wound or used to coat polymeric biomaterials in vitro and in vivo, both the protein and antibodies thereof are also useful as blocking agents to prevent or inhibit the binding of coagulase-negative staphylococci to the wound site or to any biomaterials. The SdrF, SdrG and SdrH proteins are further useful as scientific research tools to understand of the mechanisms of bacterial pathology and the development of antibacterial therapies.

The sdrF, sdrG and sdrH gene sequences are useful as nucleic acid probes for the detection and identification of coagulase-negative staphylococcal cell surface proteins. The nucleic acid sequences may also be inserted into a vector and placed in a microorganism for the production of recombinant SdrF, SdrG and SdrH proteins. The amino acid sequences of these Sdr proteins are useful as well, for example, in the production of synthetic SdrF, SdrG and SdrH proteins or portions thereof, such as consensus or variable sequence amino acid motifs.

Antisera and antibodies raised against the SdrF, SdrG and SdrH proteins or portions thereof, such as consensus or variable sequence amino acid motifs, and vaccines or other pharmaceutical compositions containing the proteins are also provided herein.

In addition, diagnostic kits containing nucleic acid molecules, the proteins, antibodies or antisera raised against SdrF, SdrG and SdrH or portions thereof, such as consensus or variable sequence amino acid motifs, and the appropriate reagents for reaction with a sample are also provided.

In a first embodiment of this invention the polynucleotide comprises a region encoding SdrF polypeptides comprising the sequence set out in FIG. 2, or a variant thereof.

In accordance with this aspect of the invention there is provided an isolated nucleic acid molecule encoding a mature polypeptide expressible by the *Staphylococcus epidermidis* strain 9491.

In a second embodiment of this invention the polynucleotide comprises a region encoding SdrG polypeptides comprising the sequence set out in FIG. 3, or a variant thereof.

In accordance with this aspect of the invention there is provided an isolated nucleic acid molecule encoding a mature polypeptide expressible by the *Staphylococcus epidermidis* strain K28.

In a third embodiment of this invention the polynucleotide comprises a region encoding SdrH polypeptides comprising the sequence set out in FIG. 4, or a variant thereof.

In accordance with this aspect of the invention there is provided an isolated nucleic acid molecule encoding a mature polypeptide expressible by the *Staphylococcus epidermidis* strain 9491.

In a fourth embodiment of the invention there is a novel protein from *Staphylococcus epidermidis* comprising the SdrF amino acid sequence as shown in FIG. 2, or a variant thereof.

In a fifth embodiment of the invention there is a novel protein from *Staphylococcus epidermidis* comprising the SdrG amino acid sequence as shown in FIG. 3, or a variant thereof.

In a sixth embodiment of the invention there is a novel protein from *Staphylococcus epidermidis* comprising the SdrH amino acid sequence as shown in FIG. 4, or a variant thereof.

In accordance with the fourth, fifth and sixth embodiments of the invention there are provided isolated nucleic acid molecules encoding SdrF, SdrG or SdrH proteins, particularly *Staphylococcus epidermidis* proteins, including mRNAs, cDNAs, genomic DNAs. Further embodiments of this aspect of the invention include biologically, diagnostically, prophylactically, clinically or therapeutically useful variants thereof, and compositions comprising the same.

In a seventh embodiment of the invention, there is provided the use of a polynucleotide of the invention for therapeutic or prophylactic purposes, in particular genetic immunization.

In an eighth embodiment of the invention are variants of SdrF, SdrG or SdrH polypeptide or portions thereof, such as consensus or variable sequence amino acid motifs, encoded by naturally occurring alleles of the sdrF, sdrG or sdrH gene.

In accordance with this embodiment of the invention there are provided novel polypeptides of *Staphylococcus epidermidis* referred to herein as SdrF, SdrG or SdrH or portions thereof, such as consensus or variable sequence amino acid motifs, as well as biologically, diagnostically, prophylactically, clinically or therapeutically useful variants thereof, and compositions comprising the same.

In a ninth embodiment of the invention, there are provided methods for producing the aforementioned SdrF, SdrG or SdrH polypeptides or portions thereof, such as consensus or variable sequence amino acid motifs.

In a tenth embodiment of the invention, there are provided antibodies against SdrF, SdrG or SdrH polypeptides or polynucleotides or portions thereof, such as consensus or variable sequence amino acid motifs or the nucleic acids which encode such motifs.

In an eleventh embodiment of the invention there are provided polynucleotides that hybridize to SdrF, SdrG or SdrH polynucleotide sequences or portions thereof, such as consensus or variable sequence amino acid motifs, particularly under stringent conditions.

In a twelfth embodiment of the invention there are provided compositions comprising an SdrF, SdrG or SdrH polynucleotide or a SdrF, SdrG or SdrH polypeptide or portions there of, such as consensus or variable sequence amino acid motifs, for administration to a cell or to a multicellular organism.

Various changes and modifications within the spirit and scope of the disclosed invention will become readily apparent to those skilled in the art from reading the following descriptions and from reading the other part s of the present disclosure.

BRIEF DESCRIPTION OF THE FIGURES

FIG. 2 is the DNA sequence of (Seq. ID No. 1) and the amino acid sequence of the SdrF protein (in bold) along with their flanking sequences (Seq. ID Nos. 2–6).

FIG. 3 is the DNA sequences sdrG (Seq. ID No. 7) and the amino acid sequence of the SdrG protein (in bold) along with their flanking sequenes (Seq. ID Nos. 8–12).

FIG. 4 is the DNA sequence of the sdrH (Seq. ID No. 13) coding region along with the amino acid sequence of the SdrH protein (Seq. ID No. 14).

FIG. 5A is a schematic representation of previously described *S. aureus* Sdr proteins;

FIG. 5B is a schematic representation of SdrF, SdrG, and SdrH showing the relative position and/or size of their signal sequences (S), region As (A), region B repeats ($B_n$), SD-repeat region (SD), region C (C) (SdrH only), and wall/membrane spanning regions (WM); and FIG. 5C rerepresents the C-terminal amino acid sequences of SdrF (Seq. ID No. 18), SdrG (Seq. ID No. 19), and SdrH (Seq. ID No. 20) showing the positions of the SD repeats, LPXTG motif (underlined), hydrophobic membrane-spauiing regions (bold), and charged terminal residues.

DETAILED DESCRIPTION OF THE INVENTION

Figure 1:
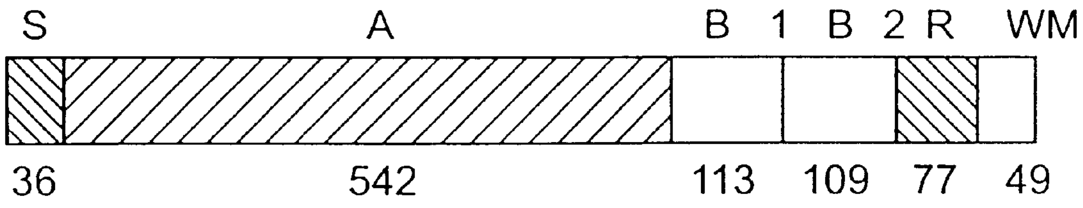
FIG. 1 is a representation of the SdrG protein of *S. epidermidis* strain K28. The regions are labeled along the top of the construct, with the number of amino acids found in each region of the protein disclosed immediately below the corresponding region in the drawing.

Isolated Sdr proteins and their corresponding amino acid and nucleic acid sequences are described herein. The proteins are designated SdrF, SdrG, and SdrH. The DNA sequence of sdrF and the amino acid sequence of the protein SdrF (in bold) are shown in FIG. 2 along with their flanking sequences. The DNA sequence of sdrG and the amino acid sequence of the protein SdrG (in bold) are shown in FIG. 3 along with their flanking sequences. Finally, the SdrH coding region including DNA and amino acid sequence is shown in FIG. 4.

The SdrF, SdrG, and SdrH proteins are related in primary sequence and structural organization to the extracellular matrix-binding Sdr family of proteins from *Staphylococcus aureus* and are localized on the cell surface. The SdrF, SdrG, and SdrH proteins are cell wall-associated proteins, with a signal sequence at the N-terminus and an LPXTG motif (Seq. ID No. 17) a hydrophobic domain and positively charged residues at the C-terminus. Each also has an SD repeat containing region R of sufficient length to allow efficient expression of the ligand binding domain region A on the cell surface. With the A region of the SdrF, SdrG, and SdrH proteins located on the cell surface, the proteins can interact with proteins in plasma, the extracellular matrix or with molecules on the surface of host cells. SdrG, for example, binds the N-terminal one-half of the beta chain of fibrinogen.

The disclosed extracellular matrix-binding proteins share a unique dipeptide repeat region (region R) including predominately aspartate and serine residues. This DS repeat is encoded by 18 nucleotide repeats with the consensus GAY TCN GAY TCN GAY AGY (Seq. ID No. 15), with TCN as the first and second serine codons and AGY as the third serine codon. The R region is near the C-terminus of the proteins and typically contains between 40 and 300 DS residues, or more particularly, greater than 60, 80, 100, 120, 150, 200 or 250 repeating units, of which greater than 90, 95 or even 98% are the amino acids D or S. The R region DS repeat varies in length between proteins, and while the region R itself does not bind extracellular matrix proteins, the R region enables the presentation of the binding regions of the protein on the cell surface of *S. aureus*. Thus, probes to the consensus DNA encoding the DS repeat (see above) can be used to identify other genes encoding different binding proteins essential to the attachment of *S. aureus* to host tissues. Antibodies to an R region can also be used to identify such additional binding proteins.

It has been discovered that in the A region of SdrF and SdrG there is highly conserved amino acid sequence that can be used to derive a consensus TYTFTDYVD (Seq. ID No. 16) motif. The motif can be used in multicomponent vaccines to impart broad spectrum immunity to bacterial infections, and also can be used to produce monoclonal or polyclonal antibodies that impart broad spectrum passive immunity. In an alternative embodiment, any combination of the variable sequence motif derived from the Sdr protein family, (T) (Y) (T) (F) (T) (D/N) (Y) (V) (D), can be used to impart immunity or to induce protective antibodies.

It has further been discovered that SdrG has an open reading frame of 2736 nucleotides that encode a protein of 913 amino acid residues. The protein has a signal sequence of 30 amino acids, a ligand binding A region of 542 amino acids, and two repeated motifs termed B regions. B1 is 113 amino acids and B2 is 110 amino acids, and the R region is 77 amino acids. B regions contain EF hand motifs that signify $Ca^{++}$ binding, and are similar to those found in other $Ca^{++}$ binding proteins such as calmodulin and troponin. An additional more degenerate form of the EF hand motif was found in the A region of SdrG between the residues 459–471. A significant decrease in the binding of SdrG A to Fibrinogen was noted in the presence of EDTA, demonstrating a metal-ion dependence for binding.

I. Definitions

The terms "SdrF protein", "SdrG protein" and "SdrH protein" are defined herein to include SdrF, SdrG, and SdrH subdomains, and active or antigenic fragments of SdrF, SdrG, and SdrH proteins, such as consensus or variable sequence amino acid motifs.

As used herein, "pg" means picogram, "ng" means nanogram, "ug" or "μg" mean microgram, "mg" means milligram, "ul" or "μl" mean microliter, "ml" means milliliter, "l" means liter.

"Active fragments" of SdrF, SdrG, and SdrH proteins are defined herein as peptides or polypeptides capable of blocking the binding of coagulase-negative staphylococci to immobilized or soluble host proteins.

The term "adhesin" as used herein includes naturally occurring and synthetic or recombinant proteins and peptides which can bind to extracellular matrix proteins and/or mediate adherence to host cells.

The term "amino acid" as used herein includes naturally occurring and synthetic amino acids and includes, but is not limited to, alanine, valine, leucine, isoleucine, proline, phenylalanine, tryptophan, methionine, glycine, serine, threonine, cysteine, tyrosine, asparagine, glutamate, aspartic acid, glutamic acid, lysine, arginine, and histidine.

An "antibody" is any immunoglobulin, including antibodies and fragments thereof, that binds a specific epitope. The term as used herein includes monoclonal antibodies, polyclonal, chimeric, single chain, bispecific, simianized, and humanized antibodies as well as Fab fragments, including the products of an Fab immunoglobulin expression library.

The phrase "antibody molecule" in its various grammatical forms as used herein contemplates both an intact immunoglobulin molecule and an immunologically active portion of an immunoglobulin molecule.

"Antigenic fragments" of SdrF, SdrG, and SdrH proteins are defined herein as peptides or polypeptides capable of producing an immunological response.

As used herein, an "antigenically functional equivalent" protein or peptide is one that incorporates an epitope that is immunologically cross-reactive with one or more epitopes of the particular proteins disclosed. Antigenically functional equivalents, or epitopic sequences, may be first designed or predicted and then tested, or may simply be directly tested for cross-reactivity.

A "cell line" is a clone of a primary cell that is capable of stable growth in vitro for many generations.

A "clone" is a population of cells derived from a single cell or common ancestor by mitosis.

A DNA "coding sequence" is a double-stranded DNA sequence which is transcribed and translated into a polypeptide in vivo when placed under the control of appropriate regulatory sequences. The boundaries of the sequence are determined by a start codon at the 5' (amino) terminus and a translation stop codon at the 3' (carboxyl) terminus. A coding sequence can include, but is not limited to, prokaryotic sequences, cDNA from eukaryotic MRNA, genetic DNA sequences from eukaryotic (e.g., mammalian) DNA, and even synthetic DNA sequences. A polyadenylation signal and transcription termination sequence will usually be located 3' to the coding sequence.

"DNA molecule" refers to the polymeric form of deoxyribonucleotides (adenine, guanine, thymine, or cytosine) in either its single stranded form, or a double stranded helix. This term refers only to the primary and secondary structure of the molecule, and does not limit it to any particular tertiary forms. Thus, this term includes double-stranded DNA found, inter alia, in linear DNA molecules (e.g, restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA.

Transcriptional and translational control sequences are "DNA regulatory sequences", such as promoters, enhancers, polyadenylation signals, terminators, and the like, that provide for the expression of a coding sequence in a host cell.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

As used herein, the term "extracellular matrix proteins," or ECM, refers to four general families of macromolecules, collagens, structural glycoproteins, proteoglycans and elastins, including fibronectin, and fibrinogen, that provide support and modulate cellular behavior.

As used herein, a "host cell" is a cell which has been transformed or transfected, or is capable of transformation or transfection by an exogenous polynucleotide sequence.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences.

"Identity" and "similarity" can be readily calculated by known methods (*Computational Molecular Biology*, Lesk, A. M., ed., Oxford University Press, New York, 1988; *Biocomputing: Informatics and Genome Projects*, Smith, D. W., ed., Academic Press, New York, 1993). While there exist a number of methods to measure identity and similarity between two sequences, both terms are well known to skilled artisans. Methods commonly employed to determine identity or similarity between sequences include, but are not limited to those disclosed in Carillo, H., and Lipman, D., *SIAM J. Applied Math.*, 48:1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, GCG program package (Devereux et al., *Nucleic Acids Research* 12(1): 387, 1984), BLASTP, BLASTN, and FASTA (Atschul et al., *J. Molec. Biol.* 215: 403–410, 1990). The BLAST X program is publicly available from NCBI and other sources (BLAST Manual, Altschul et al., NCBI NLM NIH Bethesda, Md. 20894; Altschul et al., *J. Mol. Biol.* 215: 403–410, 1990).

By "immunologically effective amount" is meant an amount of a peptide composition that is capable of generating an immune response in the recipient animal. This includes both the generation of an antibody response (B cell response), and/or the stimulation of a cytotoxic immune response (T cell response). The generation of such an immune response will have utility in both the production of useful bioreagents, e.g., CTLs and, more, particularly, reactive antibodies, for use in diagnostic embodiments, and will also have utility in various prophylactic or therapeutic embodiments.

As used herein, the term "in vivo vaccine" refers to immunization of animals with proteins so as to elicit a humoral and cellular response that protects against later exposure to the pathogen.

The term "isolated" is defined herein as free from at least some of the components with which it naturally occurs. "Isolated" as used herein also means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein.

The term "ligand" is used to include molecules, including those within host tissues, to which pathogenic bacteria attach.

The phrase "monoclonal antibody" in its various grammatical forms refers to an antibody having only one species of antibody combining site capable of immunoreacting with a particular antigen.

The term "oligonucleotide," as used herein is defined as a molecule comprised of two or more nucleotides, preferably more than three. Its exact size will depend upon many factors which, in turn, depend upon the ultimate function and use of the oligonucleotide.

As used herein, the phrase "pharmaceutically acceptable" refers to molecular entities and compositions that are physiologically tolerable and do not typically produce an unacceptable allergic or similar untoward reaction when administered to a human.

"Polynucleotide(s)" generally refers to any polyribonucleotide or polydeoxyribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules.

One of the molecules of a triple-helical region often is an oligonucleotide. As used herein, the term "polynucleotide (s)" includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 genetically encoded amino acids. "Polypeptide(s)" include those modified either by natural processes, such as processing and other post-translational modifications, but also by chemical modification techniques which are well known to the art. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains and the amino or carboxyl termini. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins such as arginylation, and ubiquitination. See, for instance Seifter et al., *Meth. Enzymol.* 182:626–646, 1990 and Rattan et al., *Ann. N.Y. Acad. Sci.* 663: 48–62, 1992. Polypeptides may be branched or cyclic, with or without branching. Cyclic, branched and branched circular polypeptides may result from post-translational natural processes and may be made by entirely synthetic methods, as well.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be substantially complementary to different strands of a particular target DNA sequence. This means that the primers must be sufficiently complementary to hybridize with their respective strands. Therefore, the primer sequence need not reflect the exact sequence of the template. For example, a noncomplementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

A "replicon" is a genetic element (e.g., plasmid, chromosome, virus) that functions as an autonomous unit of DNA replication in vivo, i.e., capable of replication under its own control.

As used herein, the terms "restriction endonucleases" and "restriction enzymes" refer to bacterial enzymes, each of which cuts double-stranded DNA at or near a specific palindromic nucleotide sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions or truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions or deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

A "vector" is a replicon, such as plasmid, phage or cosmid, to which another DNA segment may be attached so as to bring about the replication of the attached segment.

II. Nucleic Acid and Amino Acid Sequences

The nucleic acid sequences encoding SdrF, SdrG, and SdrH (as shown in FIGS. 2–4, respectively) or portions thereof, such as consensus or variable sequence amino acid motifs, are useful for the production of recombinant proteins or as nucleic acid probes for the detection of coagulase-negative staphylococci proteins in a sample or specimen with high sensitivity and specificity. The probes can be used to detect the presence of coagulase-negative staphylococci in the sample, diagnose infection with the disease, quantify the amount of coagulase-negative staphylococci in the sample, or monitor the progress of therapies used to treat the infection. The nucleic acid and amino acid sequences can also be useful as laboratory research tools to study the organism and the disease or to develop therapies and treatments for the disease.

It will be understood by those skilled in the art that the SdrF, SdrG, or SdrH proteins are also encoded by sequences substantially similar to the nucleic acid sequences provided in the Sequence Listing. Two DNA sequences are "substantially similar" when approximately 70% or more (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., *Molecular Cloning: A Laboratory Manual*, 1982; *DNA Cloning*, Vols. I & II, supra; *Nucleic Acid Hybridization*, [B. D. Hames & S. J. Higgins eds. (1985)]. By "substantially similar" is further meant a DNA sequence which, by virtue of the degeneracy of the genetic code, is not identical with that shown in any of the sequences shown in FIGS. 2–4, but which still encodes the same amino acid sequence; or a DNA sequence which encodes a different amino acid sequence that retains the activities of the proteins, either because one amino acid is replaced with a similar amino acid, or because the change (whether it be substitution, deletion or insertion) does not affect the active site of the protein. Two amino acid sequences or two nucleic acid sequences are "substantially similar" when approximately 70% or more (preferably at least about 80%, and more preferably at least about 90% or 95%) of the amino acids match over the defined length of the sequences.

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second generation molecule. The amino acid changes may be achieved by changing the codons of the DNA sequence, according to Table 1. It should be understood by one skilled in the art that the codons specified in Table 1 are for RNA sequences. The corresponding codons for DNA have a T substituted for U. In keeping with standard nomenclature (*J. Biol. Chem.*, 243:3552–3559, 1969), abbreviations for amino acid residues are further shown in Table 1.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | GAC | GAU | | |
| Glutamic acid | Glu | E | GAA | GAG | | | | |
| Phenylalanine | Phe | F | UUC | UUU | | | | |
| Glycine | Gly | G | GGA | GCG | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | GUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, *J. Mol Biol*, 157(1):105–132, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, supra, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+1.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

The polypeptides of the present invention can be can be chemically synthesized. The synthetic polypeptides are prepared using the well known techniques of solid phase, liquid phase, or peptide condensation techniques, or any combination thereof, and can include natural and unnatural amino acids. Amino acids used for peptide synthesis may be standard Boc ($N^{\alpha}$-amino protected $N^{\alpha}$-t-butyloxycarbonyl) amino acid resin with the standard deprotecting, neutralization, coupling and wash protocols of the original solid phase procedure of Merrifield (*J. Am. Chem. Soc.*, 85:2149–2154, 1963), or the base-labile $N^{\alpha}$-amino protected 9-fluorenylmethoxycarbonyl (Fmoc) amino acids first described by Carpino and Han (*J. Org. Chem.*, 37:3403–3409, 1972). Both Fmoc and Boc $N^{\alpha}$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other N -protecting groups that are familiar to those skilled in this art. Solid phase peptide synthesis may be accomplished by techniques familiar to those in the art and provided, for example, in Stewart and Young, 1984*, Solid Phase Synthesis*, Second Edition, Pierce Chemical Co., Rockford, Ill.; Fields and Noble, 1990*, Int. J. Pept Protein Res.* 35:161–214, or using automated synthesizers, such as sold by ABS. Thus, polypeptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated.

In a further embodiment, subunits of peptides that confer useful chemical and structural properties will be chosen. For example, peptides comprising D-amino acids will be resistant to L-amino acid-specific proteases in vivo. In addition, the present invention envisions preparing peptides that have more well defined structural properties, and the use of peptidomimetics and peptidomimetic bonds, such as ester bonds, to prepare peptides with novel properties. In another embodiment, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such peptides would provide ligands with unique function and activity, such as extended half-lives in vivo due to resistance to metabolic breakdown or protease activity. Furthermore, it is well known that in certain systems constrained peptides show enhanced functional activity (Hruby, *Life Sciences*, 31:189–199, 1982); (Hruby et al., *Biochem J*., 268:249–262, 1990).

The following non-classical amino acids may be incorporated in the peptide in order to introduce particular conformational motifs: 1,2,3,4-tetrahydroisoquinoline-3—carboxylate (Kazmierski et al., *J. Am. Chem. Soc.*, 113:2275–2283, 1991); (2S,3S)-methyl-phenylalanine, (2S, 3R)-methyl-phenylalanine, (2R,3S)-methyl-phenylalanine and (2R,3R)-methyl-phenylalanine (Kazmierski and Hruby, *Tetrahedron Lett*., 1991); 2-aminotetrahydronaphthalene-2-carboxylic acid (Landis, *Ph. D. Thesis, University of Arizona*, 1989); hydroxy-1,2,3,4-tetrahydro-isoquinoline-3-carboxylate (Miyake et al, *J. Takeda Res. Labs*., 43:53–76, 1989); β-carboline (D and L) (Kazmierski, *Ph. D. Thesis, University of Arizona*, 1988); HIC (histidine isoquinoline carboxylic acid) (Zechel et al, *Int. J. Pep. Protein Res*., 43, 1991); and HIC (histidine cyclic urea) (Dharanipragada).

The following amino acid analogs and peptidomimetics may be incorporated into a peptide to induce or favor specific secondary structures: LL-Acp (LL-3-amino-2- propenidone-6-carboxylic acid), a β-turn inducing dipeptide analog (Kemp et al., *J. Org. Chem.*, 50:5834–5838 (1985); β-sheet inducing analogs (Kemp et al., *Tetrahedron Lett.*, 29:5081–5082, 1988); β-turn inducing analogs (Kemp et al., *Tetrahedron Lett.*, 29:5057–5060, 1988); alpha-helix inducing analogs (Kemp et al., *Tetrahedron Lett.*, 29:4935–4938, 1988); γ-turn inducing analogs (Kemp et al., *J. Org. Chem.*, 54:109:115, 1989); and analogs provided by the following references: Nagai and Sato, *Tetrahedron Lett.*, 26:647–650 (1985); DiMaio et al., J. Chem. Soc. *Perkin Trans.*, p. 1687 (1989); also a Gly-Ala turn analog (Kahn et al., *Tetrahedron Lett.*, 30:2317, 1989); amide bond isostere (Jones et al., *Tetrahedron Lett.*, 29:3853–3856, 1989); tetrazole (Zabrocki et al., *J. Am. Chem. Soc.*, 110:5875–5880, 1988); DTC (Samanen et al., *Int. J. Protein Pep. Res.*, 35:501:509, 1990); and analogs taught in Olson et al., (*J. Am. Chem. Sci.*, 112:323–333, 1990) and Garvey et al., (*J. Org. Chem.*, 56:436, 1990). Conformationally restricted mimetics of beta turns and beta bulges, and peptides containing them, are described in U.S. Pat. No. 5,440,013, issued Aug. 8, 1995 to Kahn.

Also provided herein are sequences of nucleic acid molecules that selectively hybridize with nucleic acid molecules encoding the fibrinogen-binding proteins or portions thereof, such as consensus or variable sequence amino acid motifs, from coagulase-negative staphylococcal bacteria such as *S. epidermidis* described herein or complementary sequences thereof. By "selective" or "selectively" is meant a sequence which does not hybridize with other nucleic acids. This is to promote specific detection of sdrF, sdrG, or sdrH. Therefore, in the design of hybridizing nucleic acids, selectivity will depend upon the other components present in a sample. The hybridizing nucleic acid should have at least 70% complementarity with the segment of the nucleic acid to which it hybridizes. As used herein to describe nucleic acids, the term "selectively hybridizes" excludes the occasional randomly hybridizing nucleic acids, and thus, has the same meaning as "specifically hybridizing". The selectively hybridizing nucleic acids of the invention can have at least 70%, 80%, 85%, 90%, 95%, 97%, 98%, and 99% complementarity with the segment of the sequence to which they hybridize.

The invention contemplates sequences, probes and primers which selectively hybridize to the encoding DNA or the complementary, or opposite, strand of DNA as those specifically provided herein. Specific hybridization with nucleic acid can occur with minor modifications or substitutions in the nucleic acid, so long as functional species-specific hybridization capability is maintained. By "probe" is meant nucleic acid sequences that can be used as probes or primers for selective hybridization with complementary nucleic acid sequences for their detection or amplification, which probes can vary in length from about 5 to 100 nucleotides, or preferably from about 10 to 50 nucleotides, or most preferably about 18–24 nucleotides. Therefore, the terms "probe" or "probes" as used herein are defined to include "primers". Isolated nucleic acids are provided herein that selectively hybridize with the species-specific nucleic acids under stringent conditions and should have at least 5 nucleotides complementary to the sequence of interest as described by Sambrook et al., 1989. *Molecular Cloning: a Laboratory Manual*, 2nd ed. Cold Spring Harbor Laboratory, Cold Spring Harbor, N.Y.

If used as primers, the composition preferably includes at least two nucleic acid molecules which hybridize to different regions of the target molecule so as to amplify a desired region. Depending on the length of the probe or primer, the target region can range between 70% complementary bases and full complementarity and still hybridize under stringent conditions. For example, for the purpose of diagnosing the presence of the *S. epidermidis*, the degree of complementarity between the hybridizing nucleic acid (probe or primer) and the sequence to which it hybridizes (e.g., coagulase-negative staphylococcal DNA from a sample) is at least enough to distinguish hybridization with a nucleic acid from other bacteria.

The nucleic acid sequences encoding SdrF, SdrG, or SdrH proteins or portions thereof, such as consensus or variable sequence amino acid motifs, can be inserted into a vector, such as a plasmid, and recombinantly expressed in a living organism to produce recombinant SdrF, SdrG, or SdrH proteins or fragments thereof. For example, DNA molecules producing recombinant SdrF, SdrG, and SdrH have been produced in plasmids in accordance with the present invention.

Recombinant proteins are produced by methods well known to those skilled in the art. A cloning vector, such as a plasmid or phage DNA is cleaved with a restriction enzyme, and the DNA sequence encoding the SdrF, SdrG, or SdrH protein or fragments thereof, such as consensus or variable sequence amino acid motifs, is inserted into the cleavage site and ligated. The cloning vector is then inserted into a host to produce the protein or fragment encoded by the SdrF, SdrG, or SdrH encoding DNA. Suitable hosts include bacterial hosts such as *Escherichia coli, Bacillus subtilis*, yeasts and other cell cultures. Production and purification of the gene product may be achieved and enhanced using known molecular biology techniques.

III. Uses of Sdr Mucleic Acids

Methods of using the nucleic acids described herein to detect and identify the presence of coagulase-negative staphylococci are provided. The methods are useful for diagnosing coagulase-negative staphylococcal infections and other associated diseases such as catheter related infections, biomaterial related infections, upper respiratory tract infections (such as otitis media, bacterial tracheitis, acute epiglottitis, thyroiditis), lower respiratory infections (such as emphysema, lung abscess), cardiac (such as infective endocarditis), gastrointestinal (such as secretory diarrhea, splenic abscess, retroperitoneal abscess), central nervous system (such as cerebral abscess), ocular (such as blepharitis, conjunctivitis, keratitis, endophthalmitis, preseptal and orbital cellulitis, darcryocystitis), kidney and urinary tract (such as epididymitis, intrarenal and perinephric abscess, toxic shock syndrome), skin (such as impetigo, folliculitis, cutaneous abscesses, cellulitis, wound infection, bacterial myositis, bone and joint (such as septic arthritis, osteomyelitis), bovine mastitis, and canine pyoderma.

The method involves the steps of obtaining a sample suspected of containing coagulase-negative staphylococci. The sample may be taken from an individual, for example, from one's blood, saliva, tissues, bone, muscle, cartilage, or skin. The cells can then be lysed, and the DNA extracted, precipitated and amplified. Detection of DNA from coagulase-negative staphylococci is achieved by hybridizing the amplified DNA with a probe for coagulase-negative staphylococci that selectively hybridizes with the DNA as described above in the Detailed Description of the Invention. Detection of hybridization is indicative of the presence of coagulase-negative staphylococci.

Preferably, detection of nucleic acid (e.g. probes or primers) hybridization can be facilitated by the use of detectable moieties. For example, the probes can be labeled with biotin and used in a streptavidin-coated microtiter plate assay. Other detectable moieties include radioactive labeling, enzyme labeling, and fluorescent labeling, for example.

DNA may be detected directly or may be amplified enzymatically using polymerase chain reaction (PCR) or other amplification techniques prior to analysis. RNA or cDNA can be similarly detected. Increased or decrease expression of sdrF, sdrG, or sdrH can be measured using any of the methods well known in the art for the quantification of nucleic acid molecules, such as, for example, amplification, PCR, RT-PCR, RNase protection, Northern blotting, and other hybridization methods.

Diagnostic assays for SdrF, SdrG, or SdrH proteins or portions thereof, such as consensus or variable sequence amino acid motifs, or anti- SdrF, SdrG, or SdrH antibodies may also be used to detect the presence of a *Staphylococcus epidermidis* infection. Assay techniques for determining protein or antibody levels in a sample are well known to those skilled in the art and include methods such as radioimmunoasssay, Western blot analysis and ELISA assays.

IV. Uses of Sdr Protein or Antibody

The isolated, recombinant or synthetic proteins, or antigenic portions thereof (including epitope-bearing fragments), or fusion proteins thereof can be administered to animals as immunogens or antigens, alone or in combination with an adjuvant, for the production of antibodies reactive with SdrF, SdrG, or SdrH proteins or portions thereof, such as consensus or variable sequence amino acid motifs. In addition, the proteins can be used to screen antibodies or antisera for hyperimmune patients from whom can be derived specific antibodies having a very high affinity for the proteins.

Antibodies to SdrF, SdrG, or SdrH or to fragments thereof, such as consensus or variable sequence amino acid motifs, can be used to impart passive immunity are useful for the specific detection of coagulase-negative staphylococci proteins, for the prevention of a coagulase-negative staphylococcal infection, for the treatment of an ongoing infection or for use as research tools. The term "antibodies" as used herein includes monoclonal, polyclonal, chimeric, single chain, bispecific, simianized, and humanized or primatized antibodies as well as Fab fragments, including the products of an Fab immunoglobulin expression library. Generation of any of these types of antibodies or antibody fragments is well known to those skilled in the art.

Monoclonal antibodies are generated by methods well known to those skilled in the art. The preferred method is a modified version of the method of Kearney et al., *J. Immunol.* 123:1548–1558 (1979), which is incorporated by reference herein. Briefly, animals such as mice or rabbits are inoculated with the immunogen in adjuvant, and spleen cells are harvested and mixed with a myeloma cell line, such as P3X 63Ag8,653. The cells are induced to fuse by the addition of polyethylene glycol. Hybridomas are chemically selected by plating the cells in a selection medium containing hypoxanthine, aminopterin and thymidine (HAT). Hybridomas are subsequently screened for the ability to produce anti-SdrF, SdrG, or SdrH monoclonal antibodies. Hybridomas producing antibodies are cloned, expanded and stored frozen for future production.

Techniques for the production of single chain antibodies are known to those skilled in the art and described in U.S. Pat. No. 4,946,778 and can be used to produce single chain antibodies to the proteins described herein. Phage display technology may be used to select antibody genes having binding activities for SdrF, SdrG, or SdrH, or antigenic portions thereof, such as consensus or variable sequence amino acid motifs, from PCR-amplified genes of lymphocytes from humans screened for having antibodies to SdrF, SdrG, or SdrH or naive libraries. Bispecific antibodies have two antigen binding domains wherein each domain is directed against a different epitope.

Any of the above described antibodies may be labeled directly with a detectable label for identification and quantification of coagulase-negative staphylococci. Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA).

Alternatively, the antibody may be labeled indirectly by reaction with labeled substances that have an affinity for immunoglobulin. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art.

Antibodies to the extracellular matrix-binding proteins SdrF, SdrG, SdrH or portions thereof, such as consensus or variable sequence amino acid motifs, may also be used in production facilities or laboratories to isolate additional quantities of the proteins, such as by affinity chromatography. For example, antibodies to the fibrinogen-binding protein SdrG may be used to isolate additional amounts of fibrinogen.

The proteins, or active fragments thereof, and antibodies to the proteins are useful for the treatment and diagnosis of coagulase-negative staphylococci bacterial infections as described above with regard to diagnosis method, or for the development. of anti-coagulase-negative staphylococci vaccines for active or passive immunization. Further, when administered as pharmaceutical composition to a wound or used to coat medical devices or polymeric biomaterials in vitro and in vivo, both the proteins and the antibodies are useful as blocking agents to prevent or inhibit the binding of coagulase-negative staphylococci to the wound site or the biomaterials themselves. Preferably, the antibody is modified so that it is less immunogenic in the patient to whom it is administered. For example, if the patient is a human, the antibody may be "humanized" by transplanting the complimentarity determining regions of the hybridoma-derived antibody into a human monoclonal antibody as described by Jones et al., *Nature* 321:522–525 (1986) or Tempest et al. *Biotechnology* 9:266–273 (1991) and as mentioned above.

Medical devices or polymeric biomaterials to be coated with the antibodies, proteins and active fragments described herein include, but are not limited to, staples, sutures, replacement heart valves, cardiac assist devices, hard and soft contact lenses, intraocular lens implants (anterior chamber or posterior chamber), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, penile implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethral/ureteral/urinary devices (Foley catheters, stents, tubes and balloons), airway catheters (endotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

It will be understood by those skilled in the art that the term "coated" or "coating", as used herein, means to apply the protein, antibody, or active fragment to a surface of the device, preferably an outer surface that would be exposed to coagulase-negative staphylococcal infection. The surface of the device need not be entirely covered by the protein, antibody or active fragment.

V. Pharmaceutical Compositions

Immunological compositions, including vaccines, and other pharmaceutical compositions containing the SdrF, SdrG, or SdrH proteins or portions thereof, such as consensus or variable sequence amino acid motifs, are included within the scope of the present invention. One or more of the SdrF, SdrG, or SdrH proteins, or active or antigenic fragments thereof, or fusion proteins thereof can be formulated and packaged, alone or in combination with other antigens, using methods and materials known to those skilled in the art for vaccines. The immunological response may be used therapeutically or prophylactically and may provide antibody immunity or cellular immunity, such as that produced by T lymphocytes.

The immunological compositions, such as vaccines, and other pharmaceutical compositions can be used alone or in combination with other blocking agents to protect against human and animal infections caused by or exacerbated by coagulase-negative staphylococci. In particular, the compositions can be used to protect humans against endocarditis, toxic shock syndrome, osteomyelitis, epididymitis, cellulitis or many other infections. The compositions may also protect humans or ruminants against mastitis caused by coagulase-negative staphylococci infections. The vaccine can further be used to protect other species of animals, for example canine and equine animals, against similar coagulase-negative staphylococcal infections.

To enhance immunogenicity, the proteins may be conjugated to a carrier molecule. Suitable immunogenic carriers include proteins, polypeptides or peptides such as albumin, hemocyanin, thyroglobulin and derivatives thereof, particularly bovine serum albumin (BSA) and keyhole limpet hemocyanin (KLH), polysaccharides, carbohydrates, polymers, and solid phases. Other protein derived or non-protein derived substances are known to those skilled in the art. An immunogenic carrier typically has a molecular mass of at least 1,000 Daltons, preferably greater than 10,000 Daltons. Carrier molecules often contain a reactive group to facilitate covalent conjugation to the hapten. The carboxylic acid group or amine group of amino acids or the sugar groups of glycoproteins are often used in this manner. Carriers lacking such groups can often be reacted with an appropriate chemical to produce them. Preferably, an immune response is produced when the immunogen is injected into animals such as mice, rabbits, rats, goats, sheep, guinea pigs, chickens, and other animals, most preferably mice and rabbits. Alternatively, a multiple antigenic peptide comprising multiple copies of the protein or polypeptide, or an antigenically or immunologically equivalent polypeptide may be sufficiently antigenic to improve immunogenicity without the use of a carrier.

The SdrF, SdrG, or SdrH protein or portions thereof, such as consensus or variable sequence amino acid motifs, or combination of proteins may be administered with an adjuvant in an amount effective to enhance the immunogenic response against the conjugate. At this time, the only adjuvant widely used in humans has been alum (aluminum phosphate or aluminum hydroxide). Saponin and its purified component Quil A, Freund's complete adjuvant and other adjuvants used in research and veterinary applications have toxicities which limit their potential use in human vaccines. However, chemically defined preparations such as muramyl dipeptide, monophosphoryl lipid A, phospholipid conjugates such as those described by Goodman-Snitkoff et al. *J. Immunol.* 147:410–415 (1991) and incorporated by reference herein, encapsulation of the conjugate within a proteoliposome as described by Miller et al., *J. Exp. Med.* 176:1739–1744 (1992) and incorporated by reference herein, and encapsulation of the protein in lipid vesicles such as Novasome™ lipid vesicles (Micro Vescular Systems, Inc., Nashua, N.H.) may also be useful.

The term "vaccine" as used herein includes DNA vaccines in which the nucleic acid molecule encoding SdrF, SdrG, or SdrH, or antigenic portions thereof, such as any consensus or variable sequence amino acid motif, in a pharmaceutical composition is administered to a patient. For genetic immunization, suitable delivery methods known to those skilled in the art include direct injection of plasmid DNA into muscles (Wolff et al., *Hum. Mol. Genet.* 1:363, 1992), delivery of DNA complexed with specific protein carriers (Wu et al., *J. Biol. Chem.* 264:16985, 1989), coprecipitation of DNA with calcium phosphate (Benvenisty and Reshef, *Proc. Natl. Acad. Sci.* 83:9551, 1986), encapsulation of DNA in liposomes (Kaneda et al., *Science* 243:375, 1989), particle bombardment (Tang et al., *Nature* 356:152, 1992 and Eisenbraun et al., *DNA Cell Biol.* 12:791, 1993), and in vivo infection using cloned retroviral vectors (Seeger et al., *Proc. Natl. Acad. Sci.* 81:5849, 1984).

In another embodiment, the invention is a polynucleotide which comprises contiguous nucleic acid sequences capable of being expressed to produce a gene product upon introduction of said polynucleotide into eukaryotic tissues in vivo. The encoded gene product preferably either acts as an immunostimulant or as an antigen capable of generating an immune response. Thus, the nucleic acid sequences in this embodiment encode an immunogenic epitope, and optionally a cytokine or a T-cell costimulatory element, such as a member of the B7 family of proteins.

There are several advantages to immunization with a gene rather than its gene product. The first is the relative simplicity with which native or nearly native antigen can be presented to the immune system. Mammalian proteins expressed recombinantly in bacteria, yeast, or even mammalian cells often require extensive treatment to ensure appropriate antigenicity. A second advantage of DNA immunization is the potential for the immunogen to enter the MHC class I pathway and evoke a cytotoxic T cell response. Immunization of mice with DNA encoding the influenza A nucleoprotein (NP) elicited a $CD8^+$ response to NP that protected mice against challenge with heterologous strains of flu. (Montgomery, D. L. et al., *Cell Mol Biol*, 43(3):285–92, 1997 and Ulmer, J. et al., *Vaccine*, 15(8):792–794, 1997.)

Cell-mediated immunity is important in controlling infection. Since DNA immunization can evoke both humoral and cell-mediated immune responses, its greatest advantage may be that it provides a relatively simple method to survey a large number of *S. epidermidis* genes for their vaccine potential.

VI. Methods of Administration and Dosage of Pharmaceutical Compositions

Pharmaceutical compositions containing the SdrF, SdrG, or SdrH proteins or portions thereof, such as consensus or variable sequence amino acid motifs, nucleic acid molecules, antibodies, or fragments thereof may be formulated in combination with a pharmaceutical carrier such as saline, dextrose, water, glycerol, ethanol, other therapeutic compounds, and combinations thereof. The formulation should be appropriate for the mode of administration. The compositions are useful for interfering with, modulating, or inhibiting binding interactions between coagulase-negative staphylococci and fibrinogen on host cells.

The amount of expressible DNA or transcribed RNA to be introduced into a vaccine recipient will have a very broad dosage range and may depend on the strength of the transcriptional and translational promoters used. In addition, the magnitude of the immune response may depend on the level of protein expression and on the immunogenicity of the expressed gene product. In general, effective dose ranges of about 1 ng to 5 mg, 100 ng to 2.5 mg, 1 μg to 750 μg, and preferably about 10 μg to 300 μg of DNA is administered directly into muscle tissue. Subcutaneous injection, intradermal introduction, impression through the skin, and other modes of administration such as intraperitoneal, intravenous, or inhalation delivery are also suitable. It is also contemplated that booster vaccinations may be provided. Following vaccination with a polynucleotide immunogen, boosting with protein immunogens such as the SdrH gene product is also contemplated.

The polynucleotide may be "naked", that is, unassociated with any proteins, adjuvants or other agents which affect the recipient's immune system. In this case, it is desirable for the polynucleotide to be in a physiologically acceptable solution, such as, but not limited to, sterile saline or sterile buffered saline. Alternatively, the DNA may be associated with liposomes, such as lecithin liposomes or other liposomes known in the art, as a DNA-liposome mixture, or the DNA may be associated with an adjuvant known in the art to boost immune responses, such as a protein or other carrier. Agents which assist in the cellular uptake of DNA, such as, but not limited to, calcium ions, may also be used. These agents are generally referred to herein as transfection facilitating reagents and pharmaceutically acceptable carriers. Techniques for coating microprojectiles coated with polynucleotide are known in the art and are also useful in connection with this invention. For DNA intended for human use it may be useful to have the final DNA product in a pharmaceutically acceptable carrier or buffer solution. Pharmaceutically acceptable carriers or buffer solutions are known in the art and include those described in a variety of texts such as Remington's Pharmaceutical Sciences.

It is recognized by those skilled in the art that an optimal dosing schedule for a DNA vaccination regimen may include as many as five to six, but preferably three to five, or even more preferably one to three administrations of the immunizing entity given at intervals of as few as two to four weeks, to as long as five to ten years, or occasionally at even longer intervals.

Suitable methods of administration of any pharmaceutical composition disclosed in this application include, but are not limited to, topical, oral, anal, vaginal, intravenous, intraperitoneal, intramuscular, subcutaneous, intranasal and intradermal administration.

For topical administration, the composition is formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

In a preferred embodiment, a vaccine is packaged in a single dosage for immunization by parenteral (i.e., intramuscular, intradermal or subcutaneous) administration or nasopharyngeal (i.e., intranasal) administration. The vaccine is most preferably injected intramuscularly into the deltoid muscle. The vaccine is preferably combined with a pharmaceutically acceptable carrier to facilitate administration. The carrier is usually water or a buffered saline, with or without a preservative. The vaccine may be lyophilized for resuspension at the time of administration or in solution.

Microencapsulation of the protein will give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters, polyamides, poly (D,L-lactide-co-glycolide) (PLGA) and other biodegradable polymers. The use of PLGA for the controlled release of antigen is reviewed by Eldridge et al., *Current Topics in Microbiology and Immunology*, 146:59–66 (1989).

The preferred dose for human administration is from 0.01 mg/kg to 10 mg/kg, preferably approximately 1 mg/kg. Based on this range, equivalent dosages for heavier body weights can be determined. The dose should be adjusted to suit the individual to whom the composition is administered and will vary with age, weight and metabolism of the individual. The vaccine may additionally contain stabilizers or pharmaceutically acceptable preservatives, such as thimerosal (ethyl(2-mercaptobenzoate-S)mercury sodium salt) (Sigma Chemical Company, St. Louis, Mo.).

VII. Protein-Label Conjugates

When labeled with a detectable biomolecule or chemical, the fibrinogen-binding proteins described herein are useful for purposes such as in vivo and in vitro diagnosis of staphylococcal infections or detection of coagulase-negative staphylococci. Laboratory research may also be facilitated through use of such Sdr protein-label conjugates. Various types of labels and methods of conjugating the labels to the proteins are well known to those skilled in the art. Several specific labels are set forth below. The labels are particularly useful when conjugated to a protein such as an antibody or receptor.

For example, the protein can be conjugated to a radiolabel such as, but not restricted to, $^{32}P$, $^{3}H$, $^{14}C$, $^{35}S$, $^{125}I$, or $^{131}I$. Detection of a label can be by methods such as scintillation counting, gamma ray spectrometry or autoradiography.

Bioluminescent labels, such as derivatives of firefly luciferin, are also useful. The bioluminescent substance is covalently bound to the protein by conventional methods, and the labeled protein is detected when an enzyme, such as luciferase, catalyzes a reaction with ATP causing the bioluminescent molecule to emit photons of light.

Fluorogens may also be used to label proteins. Examples of fluorogens include fluorescein and derivatives, phycoerythrin, allo-phycocyanin, phycocyanin, rhodamine, and Texas Red. The fluorogens are generally detected by a fluorescence detector.

The protein can alternatively be labeled with a chromogen to provide an enzyme or affinity label. For example, the protein can be biotinylated so that it can be utilized in a biotin-avidin reaction, which may also be coupled to a label such as an enzyme or fluorogen. For example, the protein can be labeled with peroxidase, alkaline phosphatase or other enzymes giving a chromogenic or fluorogenic reaction upon addition of substrate. Additives such as 5-amino-2,3-dihydro-1,4-phthalazinedione (also known as Luminol®) (Sigma Chemical Company, St. Louis, Mo.) and rate enhancers such as p-hydroxybiphenyl (also known as p-phenylphenol) (Sigma Chemical Company, St. Louis, Mo.) can be used to amplify enzymes such as horseradish peroxidase through a luminescent reaction; and luminogeneic or fluorogenic dioxetane derivatives of enzyme substrates can also be used. Such labels can be detected using enzyme-linked immunoassays (ELISA) or by detecting a color change with the aid of a spectrophotometer. In addition, proteins may be labeled with colloidal gold for use in immunoelectron microscopy in accordance with methods well known to those skilled in the art.

The location of a ligand in cells can be determined by labeling an antibody as described above and detecting the label in accordance with methods well known to those skilled in the art, such as immunofluorescence microscopy using procedures such as those described by Warren and Nelson (*Mol. Cell. Biol.*, 7: 1326–1337, 1987).

VIII. Therapeutic Applications

In addition to the therapeutic compositions and methods described above, the SdrF, SdrG, or SdrH proteins or portions thereof, such as consensus or variable sequence amino acid motifs, nucleic acid molecules or antibodies are useful for interfering with the initial physical interaction between a pathogen and mammalian host responsible for infection, such as the adhesion of bacteria, particularly Gram-negative bacteria, to mammalian extracellular matrix proteins on in-dwelling devices or to extracellular matrix proteins in wounds; to block SdrF, SdrG, or SdrH protein-mediated mammalian cell invasion; to block bacterial adhesion between mammalian extracellular matrix proteins and bacterial SdrF, SdrG, or SdrH proteins or portions thereof, such as consensus or variable sequence amino acid motifs, that mediate tissue damage; and, to block the normal progression of pathogenesis in infections initiated other than by the implantation of in-dwelling devices or surgical techniques.

IX. Screening Methods

The SdrF, SdrG, or SdrH proteins, or fragments thereof, such as consensus or variable sequence amino acid motifs, are useful in a method for screening compounds to identifyr compounds that inhibit coagulase-negative staphylococci binding to host molecules. In accordance with the method, the compound of interest is combined with one or more of the SdrF, SdrG, or SdrH proteins or fragments thereof and the degree of binding of the protein to fibrinogen or other extracellular matrix proteins is measured or observed. If the presence of the compound results in the inhibition of protein-fibrinogen binding, for example, then the compound may be useful for inhibiting coagulase-negative staphylococci in vivo or in vitro. The method could similarly be used to identify compounds that promote interactions of coagulase-negative staphylococci with host molecules.

The method is particularly useful for identifying compounds having bacteriostatic or bacteriocidal properties.

For example, to screen for coagulase-negative staphylococci agonists or antagonists, a synthetic reaction mixture, a cellular compartment (such as a membrane, cell envelope or cell wall) containing one or more of the SdrF, SdrG, or SdrH proteins, or fragments thereof, such as consensus or variable sequence amino acid motifs, and a labeled substrate or ligand of the protein is incubated in the absence or the presence of a compound under investigation. The ability of the compound to agonize or antagonize the protein is shown by a decrease in the binding of the labeled ligand or decreased production of substrate product. Compounds that bind well and increase the rate of product formation from substrate are agonists. Detection of the rate or level of production of product from substrate may be enhanced by use of a reporter system, such as a calorimetric labeled substrate converted to product, a reporter gene that is responsive to changes in SdrF, SdrG, or SdrH nucleic acid or protein activity, and binding assays known to those skilled in the art. Competitive inhibition assays can also be used.

Potential antagonists include small organic molecules, peptides, polypeptides and antibodies that bind to a SdrF, SdrG, or SdrH nucleic acid molecules or proteins or portions thereof, such as consensus or variable sequence amino acid motifs, and thereby inhibit their activity or bind to a binding molecule (such as fibrinogen) to prevent the binding of the SdrF, SdrG, or SdrH nucleic acid molecules or proteins to its ligand. For example, a compound that inhibits SdrF, SdrG, or SdrH activity may be a small molecule that binds to and occupies the binding site of the SdrF, SdrG, or SdrH protein, thereby preventing binding to cellular binding molecules, to prevent normal biological activity. Examples of small molecules include, but are not limited to, small organic molecules, peptides or peptide-like molecules. Other potential antagonists include antisense molecules. Preferred antagonists include compounds related to and variants or derivatives of SdrF, SdrG, or SdrH proteins or portions thereof, such as consensus or variable sequence amino acid motifs.

The nucleic acid molecules described herein may also be used to screen compounds for antibacterial activity.

X. Detection Kits for Coagulase-Negative Staphylococci

The invention further contemplates a kit containing one or more sdrF, sdrG, or sdrH-specific nucleic acid probes, which can be used for the detection of coagulase-negative staphylococci or coagulase-negative staphylococcal Sdr proteins or portions thereof, such as consensus or variable sequence amino acid motifs, in a sample or for the diagnosis of coagulase-negative staphylococcal infections. Such a kit can also contain the appropriate reagents for hybridizing the probe to the sample and detecting bound probe.

In an alternative embodiment, the kit contains antibodies specific to one or more SdrF, SdrG, or SdrH protein or peptide portions thereof, such as consensus or variable sequence amino acid motifs, which can be used for the detection of coagulase-negative staphylococci.

In yet another embodiment, the kit contains one or more SdrF, SdrG, or SdrH-proteins, or active fragments thereof, which can be used for the detection of coagulase-negative staphylococci organisms or antibodies to coagulase-negative staphylococcal Sdr proteins in a sample.

The kits described herein may additionally contain equipment for safely obtaining the sample, a vessel for containing the reagents, a timing means, a buffer for diluting the sample, and a colorimeter, reflectometer, or standard against which a color change may be measured.

In a preferred embodiment, the reagents, including the protein or antibody, are lyophilized, most preferably in a single vessel. Addition of aqueous sample to the vessel results in solubilization of the lyophilized reagents, causing them to react. Most preferably, the reagents are sequentially lyophilized in a single container, in accordance with methods well known to those skilled in the art that minimize reaction by the reagents prior to addition of the sample.

EXAMPLES

The following examples are included to demonstrate preferred embodiments of the present invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Identification of Sdr Encoding Genes in Coagulase Negative Staphylococci

Five genes (clfA, clfB, sdrC, sdrD, sdrE) have been identified in *Staphylococcus aureus* that contain the dipeptide aspartic acid and serine (DS), encoded by an 18 bp repeat motif GAY TCN GAY TCN GAY AGY, where Y=pyrimidines and N=any base. This family of proteins has been named the Sdr's for serine-aspartic acid repeat. All of the 5 *S. aureus* sdr genes encode proteins that contain features that characterize them as surface associated proteins in Gram positive bacteria; namely at the N-terminus there is a secretory signal and at the C-terminus there are (i) several positive charged residues that serve as a stop signal for protein secretion, (ii) a hydrophobic transmembrane region and (iii) a wall-spanning region with an LPXTG motif that is required for accurate sorting and correct protein orientation in the cell wall. To identify novel genes that encode cell surface proteins in coagulase negative staphylococci we used the DS coding region of clfA as a gene probe to determine if homologs exist within various coagulase negative staphylococcal species. The coagulase negative staphylococcal species that we characterized were (1) *S. lugdunensis*, (2) *S. haemolyticus*, (3) *S. schleiferi* and (4) *S. epidermidis*. Each strain is listed below.

Ten strains each of *S. epidermidis, S. lugdunensis, S. schleiferi* and *S. haemolyticus* were obtained from Jerome Etienne (Lyon, France). In addition, Dr. Timothy Foster's strain collection contained *S. epidermidis* strains donated from other researchers. Southern hybridization analysis using genomic DNA isolated from all coagulase-negative staphylococcal strains was performed. Chromosomal DNA was cleaved with HindIII and the DS coding region of clfA was DIG-labeled (Boehringer) and used as a probe. Southern hybridization analysis of all ten *S. lugdunensis* strains revealed that a single HindIII fragment, of 9 kb, hybridized to the DS coding region of clfA. Analysis of *S. haemolyticus* strains with the DS-coding sequence of clfA revealed different sized fragments. Out of the ten strains tested, six strains gave a strongly hybridizing band between 18 kb and 10 kb. The possibility exists that more than one DS coding region is present on the HindIII fragment. After longer exposure of the autoradiogramn, the four remaining strains showed weak hybridization to the DS coding region of clfA. The clfA probe did not detect a DS coding region in the genomic DNA from *S. schleiferi*. All *S. epidermidis* strains characterized revealed at least two HindIII fragments that hybridized to the DS coding region of clfA. Strains tested:

*S. lugdunensis* Strains
1. *S. lugdunensis* N940113
2. *S. lugdunensis* N940164
3. *S. lugdunensis* N940135
4. *S. lugdunensis* N950232
5. *S. lugdunensis* N920143
6. *S. lugdunensis* N930432
7. *S. lugdunensis* N940084
8. *S. lugdunensis* N940025
9. *S. lugdunensis* N910319
10. *S. lugdunensis* N910320

*S. epidermidis* Strains
1. *S. epidermidis* ATCC 1499O (Kloos)
2. *S. epidermidis* KH11
3. *S. epidermidis* K28
4. *S. epidermidis* TU3298
5. *S. epidermidis* 9142
6. *S. epidermidis* 1457
7. *S. epidermidis* 8400
8. *S. epidermidis* RP62a
9. *S. epidermidis* N910102
10. *S. epidermidis* N910173
11. *S. epidermidis* N910191
12. *S. epidermidis* N910231
13. *S. epidermidis* N910249
14. *S. epidermidis* N910275
15. *S. epidermidis* N950190
16. *S. epidermidis* N950329
17. *S. epidermidis* N910308
18. *S. epidermidis* N910160

*S. haemolyticus* Strains
1. *S. haemolyticus* N97061
2. *S. haemolyticus* N960512
3. *S. haemolyticus* N910106
4. *S. haemolyticus* N91024
5. *S. haemolyticus* N920160
6. *S. haemolyticus* N910287
7. *S. haemolyticus* N92018
8. *S. haemolyticus* N930100
9. *S. haemolyticus* N950252
10. *S. haemolyticus* N93016

*S. schleiferi* Strains
1. *S. schleiferi* JCM7430
2. *S. schleiferi* N920247

3. *S. schleiferi* N910245
4. *S. schleiferi* N910017
5. *S. schleiferi* N960518
6. *S. schleiferi* N950242
7. *S schleiferi* N920162
8. *S. schleiferi* N92017
9. *S. schleiferi* N930047
10. *S. schleiferi* N920260

SdrF Homologues in Other *S. epidermidis* Strains 17 strains of *S. epidermidis* were examined for the presence of the sdrF gene by Southern hybridization. Chromosomal DNA of the individual strains was cleaved with HindIII and probed with a region A coding sequence of sdrF as a probe. This DNA probe was DIG-labeled by PCR using pC5 (described further below in Example 2) as a template. The sdrF gene was present on a HindIII fragment that varied from 4–10 kb and was present in 12 out of 16 strains tested. Using the region R coding sequence of clfA as a probe also identified a band of the same size indicating that sdrF homologues in other *S. epidermidis* strains also contain region R coding sequence.

SdrG Homologues in Other *S. epidermidis* Strains 16 strains of *S. epidermidis* were tested for the presence of the sdrG gene using a probe designed to the region A coding sequence of sdrG. Southern hybridization analysis revealed that sdrG was present on a 16 kb HindIII fragment and was present in all *S. epidermidis* strains examined. The primer sequence used for amplification of region A coding sequence of sdrG is as follows:

F1-sdrG: 5' GATGATGAATTATCAGAC 3' Seq. ID. No. 21

R.-sdrG: 5' CAGGAGGCAAGTCACCTTG 3' Seq. ID. No. 22)

(encompassing coordinates 195 to 1795 of sdrG)

DS-coding Region Homologues in *S. epidermidis* Strains

Chromosomal DNA was cleaved with HindIII and the DS-coding region of clfA was DIG labeled (Boehringer) and used a probe. Southern hybridization analysis revealed at least two HindIII fragments that hybridized to the DS-coding region of clfA. Ten strains hybridized to three HindIII fragments.

Example 2

Studies of the Sdr Genes in Coagulase Negative staphylococci, and Identification, Isolation, Sequencing and Expression of SdrF, SdrG and SdrH

Overview

*Staphylococcus epidermidis* strains can express three different cell surface-associated proteins that contain serine-aspartate dipeptide repeats. Proteins SdrF and SdrG are similar in sequence and structural organization to the Sdr proteins of *S. aureus*. They comprise 625 and 548 residue unique region As at their N termini, respectively, followed by a variable number of 110–119 residue region B repeats, an SD repeat region, and C-terminal LPXTG motifs and hydrophobic domains characteristic of surface proteins that are covalently anchored to peptidoglycan. In contrast, SdrH has a short 60 residue region A at the N terminus, followed by a SD repeat region, a unique 277 residue region C, and a C-terminal hydrophobic domain. SdrH lacks an LPXTG motif. DNA encoding each region A of SdrF, SdrG and SdrH was cloned into expression vectors in *E. coli*, and recombinant protein was expressed and purified. Specific antisera were raised in rabbits and used to identify the Sdr proteins expressed by *S. epidermidis*. Only SdrF was released from lysostaphin-generated protoplasts of cells grown to late exponential phase. SdrG and SdrH remained associated with the protoplast fraction and were thus not sorted and linked to peptidoglycan. In Southern hybridization analyses, the sdrG and sdrH genes were present in all sixteen strains tested, while sdrF was present in twelve strains. Antisera from fifteen patients that had recovered from *S. epidermidis* infections contained antibodies that reacted with recombinant region As of SdrF, SdrG and SdrH, suggesting that these proteins are expressed during infection.

Background

*S. epidermidis* is a common inhabitant of human skin and a frequent cause of foreign-body infections. Pathogenesis is facilitated by the ability of the organism to first adhere to, and subsequently form biofilms on, indwelling medical devices such as artificial valves, orthopedic devices, and intravenous and peritoneal dialysis catheters. Device-related infections jeopardize the success of medical treatment and significantly increase patient morbidity (11).

Adherence of *S. epidermidis* to synthetic surfaces has been corrolated with both surface hydrophobicity and cell-surface proteins. (2, 13). Protease treatment of *S. epidermidis* has been shown to reduce hydrophobicity and adherence (24), and a monoclonal antibody reactive to a 220 kDa cell-surface protein of *S. epidermidis* was able to partially block bacterial attachment to polystyrene (30). Polysaccharide expressed by the ica operon is crucial in formation of biofilm. One group suggested that the polysaccharide adhesin (PS/A) is sufficient for both adhesion and cell-cell interaction associated with the accumulation phase of biofilm formation. Another view is that adherence is mediated by a surface-associated protein while the polysaccharide is responsible only for the accumulation phase (5, 12, 19).

Like *S. epidermidis, S. aureus* can also adhere to medical-implant devices but this attachment is predominantly mediated by bacterial receptors specific for host fibrinogen and fibronectin that coat biomaterial surfaces shortly after implantation. *S. aureus* adhesins that mediate these interactions include the fibrinogen-binding proteins, ClfA and ClfB, and the fibronectin-binding proteins, FnbpA and FnbpB [reviewed in (3)]. Although *S. epidermidis* has the potential to interact with fibrinogen, fibronectin, vitronectin, and laminin (6, 25, 29), little is known of the specific adhesins mediating these interactions or of how these interactions influence bacterial adherence to biomaterials coated with host proteins.

The fibrinogen-binding clumping factor protein (or ClfA) of *S. aureus* (FIG. 1A) is distinguished by the presence of a serine-aspartate (SD) dipeptide repeat region (referred to as region R in previous studies) located between a ligand-binding region A and C-terminal sequences and associated with attachment to the cell-wall (16, 17). The SD-repeat region is predicted to span the cell wall and extend the ligand-binding region from the surface of the bacteria (4). ClfA is the predecessor of a SD-repeat (Sdr) protein family found in *S. aureus*. Additional members include ClfB (a second fibrinogen-binding clumping factor), SdrC, SdrD, and SdrE (FIG. 5A) (8, 21). SdrC, SdrD, and SdrE proteins contain additional repeats, termed region B repeats, located between the region A and SD repeats. Each B repeat is 110–113 amino acids in length and contains a putative $Ca^{2+}$-binding, EF-hand motif. Ca binding has been shown to be required for the structural integrity of the region B repeats (9). The functions of SdrC, SdrD, and SdrE are unknown, but the proteins are hypothesized to interact with host matrix molecules via their region As.

This example describes three Sdr proteins expressed by *S. epidermidis*. Two have sequence similarity to, and the same structural organization, as the Sdr proteins of *S. aureus*, while SdrH is distinct. The genes encoding these proteins are prevalent among *S. epidermidis* strains. The presence of antibodies reactive to each Sdr region A in convalescent patient antisera suggest that the proteins are expressed during infection.

Materaals and Methods

Bacterial Strains and Growth Conditions.

*E. coli* XL-1 Blue or JM109 were used as recombinant host strains. Strains XL-1 Blue or TOPP 3 (Stratagene, La Jolla, Calif.) cells were used for protein expression. Bacteria were routinely grown in Luria broth or agar (Gibco BRL, Gaithersburg, Md.) supplemented with 100 $\mu g\ ml^{-1}$ ampicillin (USB, Cleveland, Ohio). *S. epidermidis* strains (Table 2) were grown in tryptic soy broth (TSB) or agar (TSA) (Difco, Detroit, Mich.).

Cloning and Sequencing of the Sdr Genes

The sdrF gene was cloned from *S. epidermidis* strain 9491. HindIII-DNA fragments ranging from 6.5 to 7.5 kb in length were isolated from an agarose gel and ligated into a pBluescript SK+ cloning vector (Stratagene) digested with HindIII and treated with calf-intestine alkaline phosphatase (CIAP) (Promega, Madison, Wis.). One recombinant plasmid, pC5, was identified by PCR screening (27) with primers directed toward DNA encoding the SD-repeat region of ClfA (P3 and P4 primers, Table 3).

The sdrG gene was cloned from a λGem®-11 library of *S. epidermidis* strain K-28 generated with DNA that had been partially digested with Sau3A and ligated into the half-site XhoI arms of λGem®-11 (Promega). After packaging, a positive phage, designated E6-2, was identified by hybridization of a DNA probe representing the ClfA SD-repeat region. A SacI-KpnI DNA fragment from E6-2 was then subcloned into the *E. coli* plasmid vector, pZero (Invitrogen, Carlsbad, Calif.). This clone was then mapped with restriction endonucleases, and a 3.5 kb EcoRI-KpnI fragment containing DNA with homology to that encoding SD-repeat amino acids sequence was subcloned into pUC18 (Amersham Pharmacia Biotech, Piscataway, N.J.) to create pE6-2.

The sdrH gene was cloned as follows. HindIII fragments obtained from *S. epidermidis* strain 9491 genomic DNA were size fractionated on a 5–20% sucrose gradient. DNA from fractions containing 1.5–2.5 kb fragments were ligated into pBluescript digested with HindIII and dephosphorylated with CIAP (Promega). *E. coli* transformants containing the ligated products were screened by colony-blot hybridization with a DIG-labeled (Boehringer Mannheim, Indianapolis, Ind.) probe made to DNA encoding the ClfA SD-repeat region.

Automated dideoxy-DNA sequencing was performed on both strands of cloned DNA. In most cases, extension of DNA sequence on a given clone was achieved with primer walking. This method, however, could not cover the length of repeat DNA encoding the SD-repeats of SdrF. Therefore, this region of DNA was excised from pC5 with Sau3A, ligated into pBluescript, and used as a template for the construction of exonuclease deletion derivatives (Erase-a-base System, Promega). Appropriate deletions on both strands (not shown) were identified by PCR screening and restriction mapping.

TABLE 2

*S. epidermidis* strains used in this study

| Strains | Comments and properties | Source or reference |
|---|---|---|
| 9491 | SdrF and SdrH prototype strain | ATCC strain |
| ATCC14990 | Reference strain | W. Kloos |
| KH11 | | P. Vaudaux |
| K28 | SdrG prototype strain | P. Vaudaux |
| RP62a | | |
| TU3298 | Transformable strain | F. Gotz |
| 9142 | Biofilm former | D. Mack |
| 1457 | | D. Mack |
| 8400 | | |
| N910308 | Reference strain, Lyon, France | J. Etienne |
| N910160 | Reference strain, Lyon, France | J. Etienne |
| N910102 | Reference strain, Lyon, France | J. Etienne |
| N910173 | Reference strain, Lyon, France | J. Etienne |
| N910191 | Reference strain, Lyon, France | J. Etienne |
| N910231 | Reference strain, Lyon, France | J. Etienne |
| N910249 | Reference strain, Lyon, France | J. Etienne |

TABLE 3

Primers used in PCR amplification for DNA probes and protein expression constructs

| Regions amplified | Sequence | Vector destination | Template DNA |
|---|---|---|---|
| clfA SD repeat | F: GCCGGATCCCCAATTCCAGAGGATTCA(SEQ ID NO.23)<br>R: GCCAAGCTTATTGTTAGAACCTGACTC(SEQ ID NO.24) | na | pCF48 |
| SD repeats | P3: GATTCAGATAGCCATTC(SEQ ID NO.25)<br>P4: CTGAGTCACTGTCTGAG(SEQ ID NO.26) | na | sdr clones |
| sdrF region A | F: CCCGGATCCGCTGAAGACAATCAATTAG(SEQ ID NO.27)<br>R: CCCAAGCTTAATTATCCCCCTGTGCTG(SEQ ID NO.28) | pQE30 | strain 9491 |
| sdrG region A | F: CCCGGATCCGAGGAGAATACAGTACAAGACG(SEQ ID NO.29)<br>R: CCCGGTACCTAGTTTTTCAGGAGGCAAGTCACC(SEQ ID NO.30) | pQE30 | strain K28 |
| sdrH full length | F: CCCGGATCCGAAGGTAATCATCCTATTGAC(SEQ ID NO.31)<br>R: CCCAAGCTTACTTTTTTCTTCTAAAGATATATAGTC C(SEQ ID NO.32) | pQE30 | strain 9491 |
| sdrF region A | F: same as above<br>R: CCCGAATTCAATTATCCCCCTGTGCTGTTG(SEQ ID NO.33) | pGEX-2T | strain 9491 |
| sdrG region A | F: same as above<br>R: CCCGAATTCTAGTTTTTCAGGAGGCAAGTCACC(SEQ ID NO.34) | pGEX-2T | strain K28 |

TABLE 3-continued

Primers used in PCR amplification for DNA probes and protein expression constructs

| Regions amplified | Sequence | Vector destination | Template DNA |
|---|---|---|---|
| sdrH region A | F: GGCGGATCCGAAGGTAATCATCCTATTG(SEQ ID NO.35)<br>R: GGCAAGCTTCTAAATATGTGTCATTTTC(SEQ ID NO.36) | pGEX-KG | strain 9491 |

na: not applicable
underline: restriction endonuclease site used for cloning

Southern Hybridizations

Southern blot transfers and hybridizations have been described elsewhere (8). DNA probes were made from PCR products encoding the SD-repeat region of ClfA or each region A of SdrF, SdrG, and SdrH (Table 3). PCR products were generated with Taq DNA polymerase (Gibco BRL), and probes were digoxigenin (Boehringer Mannheim) or fluorescein (Amersham) labeled.

Protein Expression and Purification for Antisera Production

DNA encoding recombinant SdrF, SdrG, or SdrH region A was obtained by PCR amplification of genomic template DNA from *S. epidermidis* strains 9491 or K28 with appropriate primers (Table 3). The SdrF region A construct lacked the terminal residue, proline. PCR utilized Pfu DNA polymerase (Stratagene); specifications have been previously described (7). PCR products were digested with appropriate restriction endonucleases and ligated into the expression vectors pQE30 (Qiagen, Valencia, Calif.) to generate histidine-tagged proteins, or pGEX-2T (Pharmacia) or pGEX-KG to generate GST-tagged proteins. Proteins were expressed in *E. coli* by growing 4 liters of recombinant organisms to an optical density ($OD_{600}$) of 0.5 and inducing with 0.3 mM isopropyl-1-thio-β-D-galactoside (IPTG) (Gibco BRL) for two hours. The cells were harvested in PBS (150 mM NaCl, 4.3 mM $Na_2HPO_4$, 1 mM $NaH_2PO_4$) and frozen at −80° C. *E. coli* were passed through a French press and the supernatants of these lysates were filtered through a 0.45 μm membrane. Soluble histidine-tagged proteins, present in the supernatants, were initially purified by metal-chelating chromatography. The supernatants were applied to a 5 ml $Ni^{2+}$-charged HiTrap chelating column (Pharmacia Biotech Inc.) and bound proteins were eluted with 200 ml linear gradients of 0–200 mM imidazole in 4 mM Tris-HCl, 100 mM NaCl, pH 7.9 at a flow rate of 5 ml/min. Fractions containing recombinant proteins were identified by SDS-PAGE (see below), pooled, and dialyzed against 25 mM Tris-HCl, pH 8.0. Dialyzed proteins were concentrated and further purified by ion-exchange chromatography by applying the samples to a 5 ml HiTrap Q column (Pharmacia Biotech Inc.) and eluting bound proteins with 200 ml linear gradients of 0–0.5 M NaCl in 25 mM Tris-HCl, pH 8.0 at a flow rate of 5 ml/min. Fractions containing purified recombinant proteins were identified by SDS-PAGE. GST-tagged proteins were purified from *E. coli* lysates obtained as described above. Lysates were passed through 10 ml glutathione-agarose columns under gravity flow and washed with five column volumes of PBS. Proteins were eluted from the columns with freshly prepared 5 mM reduced glutathione (Sigma) in 50 mM Tris-HCl, pH 8.0. Purified proteins were used to raise antisera in New Zealand White rabbits using standard protocols issued by HTI Bioproducts (Romano, Calif.) or by the Biological Core Facility at the National University of Ireland (Dublin, Ireland).

SDS-PAGE and Western Blot Transfer

SDS-PAGE utilized trycine gels containing 10% acrylamide (28). Separated proteins were transferred to PVDF membrane (Immobilon-P, Millipore, Bedford, Mass.) with a semi-dry transfer cell (Bio-Rad Laboratories, Hercules, Calif.). All protein samples were heat denatured under reducing conditions. Purified proteins (1 μg each) were subjected to SDS-PAGE and stained with Coomassie brilliant blue. *E. coli* lysates or lysate fractions were obtained as follows: IPTG induced, recombinant *E. coli* were grown to an $OD_{600}$ of 2.0, washed and resuspended to original volume in PBS and prepared for SDS-PAGE. 10 μl of each preparation was loaded into individual wells of acrylamide gels. *S. epidermidis* strains were grown to early stationary phase in TSB containing 1.25 U per 10 ml of the endoproteinase inhibitor $\alpha_2$-Macroglobulin (Boehringer Mannheim). The cells were adjusted to an $OD_{600}$ of 2, washed, and resuspended in one half the original volume. Protease inhibitors (4 mM phenylmethylsulphonyl fluoride, 1 mM N-ethylmaleimide, and 25 mM aminohexanoic acid) and DNAse (10 μg $ml^{-1}$) were added prior to lysostaphin (100 μg $ml^{-1}$) and lysozyme (100 μg $ml^{-1}$). Enzymatic digestions were performed for 30 min. at 37° C. with shaking. Separation of cell-wall proteins from protoplasts utilized the same conditions in the presence of 30% raffinose. *S. epidermidis* lysates or lysate fractions were treated as those for *E. coli* and 30 μl aliquots of samples were placed into wells of acrylamide gels.

Immunoassays

Western immunoassays were performed as follows: Western blots were incubated in PBS containing 1% non-fat dry milk for 1 hr. The blots were then incubated with antisera (diluted in PBS-milk) for 1 hr. Monoclonal, anti-histidine antibody (Clonetech, Palo Alto, Calif.) was diluted to 1:3000. Anti-SdrFA antisera (immune, preimmune, and antigen-absorbed) were diluted to 1:30,000; anti-SdrGA antisera were diluted to 1:2000, and anti-SdrHA antisera were diluted to 1:1000. Antisera absorptions have been previously described (14). Briefly, anti-SdrFA and anti-SdrGA antisera were extensively absorbed, respectively, with GST-tagged SdrGA and SdrFA proteins present in insoluble fractions of induced *E. coli* that had been sonicated and then centrifuged. This procedure was used to remove potential cross-reactive antibodies present in each antiserum. Removal of immunoreactive anti-SdrFA, -SdrGA, and -SdrHA antibodies was accomplished by absorbing each antiserum with *E. coli* lysates containing, respectively, GST-tagged SdrFA, SdrGA, and SdrHA. Following antisera incubation, Western blots were washed three times with PBS and incubated with a 1:2000 dilution of goat, anti-rabbit or anti-mouse IgG conjugated to alkaline phosphatase (Bio-Rad Laboratories) for 30 min. The blots were then washed and developed in chromogenic substrate (150 μg $ml^{-1}$ 5-bromo-4-chloro-3-indolyl phosphate p-toluidine salt and 300 μg $ml^{-1}$ p-nitro blue tetrazolium chloride in bicarbonate buffer) (Bio-Rad) for 10–15 min.

Reactivity of convalescent patient IgG to recombinant proteins has been previously described (1). Antisera from fifteen individuals recovering from *S. epidermidis* infections were collected and IgG was purified using protein-A sepharose chromatography. An enzyme-linked immunosorbent assay (ELISA) was used to demonstrate reactivity of IgG (2 μg per well) to recombinant proteins (1 μg per well of histidine-tagged SdrFA or SdrGA, or GST-tagged SdrHA) coated on microtiter plates.

Results

Identification of the SdrF, SdrG, and SdrH Genes

Preliminary Southern hybridization analysis of *S. epidermidis* DNA revealed the presence of several loci hybridizing with DNA encoding the SD repeats of the *S. aureus* Sdr protein family (unpublished observations). To further define these loci, we cloned three DNA fragments from *S. epidermidis* strains 9491 and K28. Two clones, pC5 and pC28, were obtained from strain 9491 by direct ligation of HindIII-DNA fragments into *E. coli* plasmid vectors. A third clone, E6-2, was obtained from a λGem®-11 genomic library made from strain K28. A segment of the E6-2 insert DNA was subcloned into an *E. coli* plasmid vector to form pE6-2. pC5, pE6-2, and pC28 were found to have 6.8, 6.0, and 2.0 kb DNA inserts, respectively (not shown).

DNA sequence analysis revealed the presence of single open reading frames (ORF) in each plasmid. The ORFs, designated sdrF, sdrG, and sdrH, were 5199, 2793, and 1461 base pairs (bp) in length, respectively. A leucine, rather than a methionine, codon is predicted to act as a translational start codon for sdrG. A potential ribosome binding site (GGAG) (SEQ ID NO. 37) was identified 7–12 bp 5' of each ORF. DNA sequences of 500–1000 bp flanking the sdrF, sdrG, and sdrH ORFs were not similar, suggesting that they are not tandemly linked like the sdrC, sdrD, and sdrE genes of *S. aureus* (data not shown).

The Deduced Amino Acids Sequences of SdrF, SdrG, and SdrH.

Figure 5:
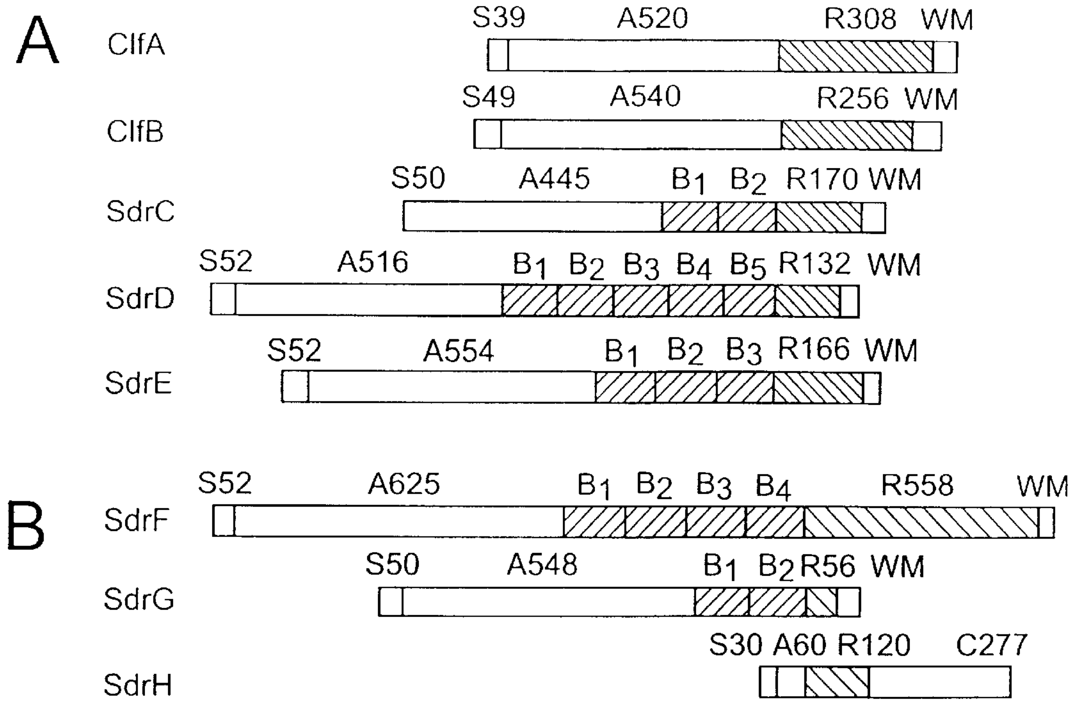
FIG. 5 shows the relationships between the Sdr proteins of *S. aureus* and *S. epidermidis* as follows.

The amino acid structural organization of the *S. epidermidis* SdrF and SdrG proteins are similar to the *S. aureus* Sdr proteins and thus have features typical of cell-surface proteins that are covalently anchored to the peptidoglycan of Gram-positive bacteria. These cell-surface features include positively-charged residues at the extreme C terminus preceded by a hydrophobic membrane spanning region, and an LPXTG (SEQ ID NO. 17) motif. The SD repeat regions are located N-terminal of the LPXTG (SEQ ID NO. 17) motif and are proposed to traverse the cell wall (4, 10). SdrF and SdrG contain predicted signal sequences at their N-termini (52 and 50 residues, respectively) and residues associated with cell wall linkage at their C-termini (FIG. 5B, 5C). The SD-repeat regions of SdrF and SdrG (see below) end seven and thirteen residues, respectively, proximal to the LPXTG motifs. The SD-repeat regions of SdrF and SdrG contain 558 and 56 residues, respectively (FIG. 5B). The dipeptide composition of SdrG does not diverge from serine and aspartate, whereas in SdrF, 26 alanine residues occur within the SD-repeat region. The predicted molecular masses of the mature proteins (with loss of the signal sequences) are 179 kDa for SdrF and 97.6 kDa for SdrG.

The Sdr proteins of *S. aureus* each possess a structurally distinct, known or putative ligand-binding domain at their N terminus called region A (8, 16, 21). The N termini of mature SdrF and SdrG possess 625 and 548 amino acid region As, respectively. Pairwise comparisons reveal that the amino acid sequences of SdrF and SdrG region As are 22% identical to each other and 20–35% (mean=23%) identical to the region As of the *S. aureus* Sdr proteins.

Amino acid sequence motifs have been reported in the region As of *S. aureus* Sdr proteins, and these include a putative $Ca^{2+}$-binding EF-hand motif in ClfA, a cation-coordinating MIDAS motif in ClfB, and a common Sdr protein motif, TYTFTDYVD (SEQ ID NO. 16), of unknown function (8, 23). The region As of SdrF and SdrG both contain a TYTFTDYVD (SEQ ID NO. 38) motif, and an EF-hand motif (DYSEYEDVTNDDY) (SEQ ID NO. 16) was found in the region A of SdrG.

Three Sdr proteins of *S. aureus* (SdrC, SdrD, and SdrE) contain variable numbers of 110–113 amino acid segments called region B repeats (FIG. 5A), and each repeat contains a putative $Ca^{2+}$-binding EF-hand motif (8, 9). Likewise, SdrF contains four region B repeats (of 119, 110, 111, and 111 residues), and SdrG contains two region B repeats (of 113 and 111 residues) (FIG. 5B). Each repeat contains a putative EF-hand motif with a consensus sequence of DX(N/D)X(D/N)GXX(DIN/G)XX(E/D). The region B repeats of SdrF and SdrG have 43–85% (mean=55%) identity with each other and 39–73% (mean=54%) identity to the region B repeats found in the *S. aureus* Sdr proteins.

The structural organization of SdrH at the amino acid sequence level is considerably different than that of SdrF and SdrG. Following a potential 30 residue signal sequence at its N terminus, SdrH has a unique 60 residue stretch (region A) followed by a 120-residue SD-repeat region and a 277-residue segment, region C, that contains a hydrophobic sequence at its C terminus but lacks an appropriately placed LPXTG motif. The sequence LGVTG, however, occurs within the hydrophobic region. (FIG. 1B, 1C). SdrH contained no region B repeats. The region A and region C of SdrH have no amino acid sequence similarities with other known Sdr proteins or protein sequences from various databases. Motifs common to other Sdr proteins were not found. The mature molecular mass of SdrH is predicted to be 50.5 kDa.

Together, these result suggest that *S. epidermidis* has the capacity to express two proteins related to the *S. aureus* Sdr protein family, as well as a third Sdr protein with novel structure.

Distribution of SdrF, SdrG, and SdrH in *S. epidermidis* Strains.

Figure 6A:
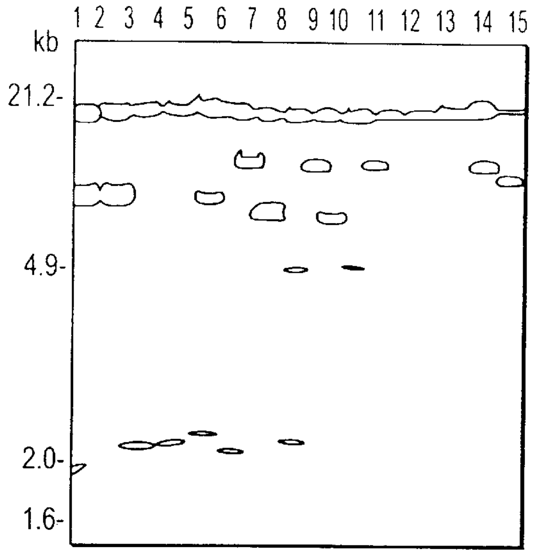
FIG. 6 illustrates the prevalence of the sdr genes in *S. epidermidis* strains and shows Southern blots containing *S. epidermidis* genomic DNA hybridizing to DNA probes encoding the: (A) the SD-repeat region; (B) the SdrH region A; (C) the SdrG region A; and (D) the SdrG and SdrF region As. Strains are as follows: lane 1, ATCC14990; lane 2, KH11; lane 3, K28; lane 4, RP62a; lane 5, TU3298; lane 6, 9142; lane 7 1457; lane 8, 8400; lane 9, N910308; lane 10, N910160; lane 11, N910102; lane 12, N910173; lane 13, N910191; lane 14, N910231; lane 15, N950249. Strain 9491 is not shown. Kilobases (kb) size markers are shown at the left of panels A–D.
Figure 6B:
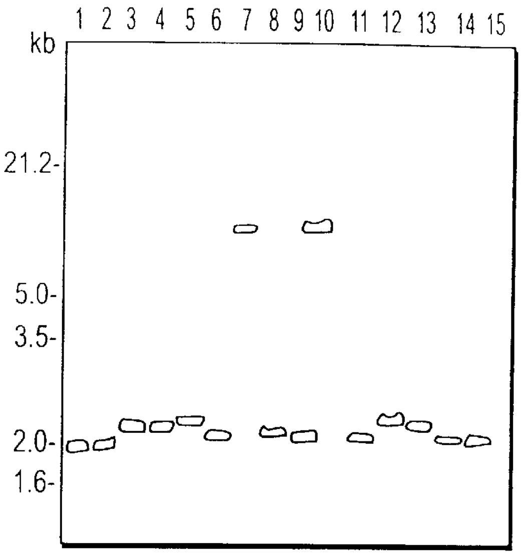
Figure 6C:
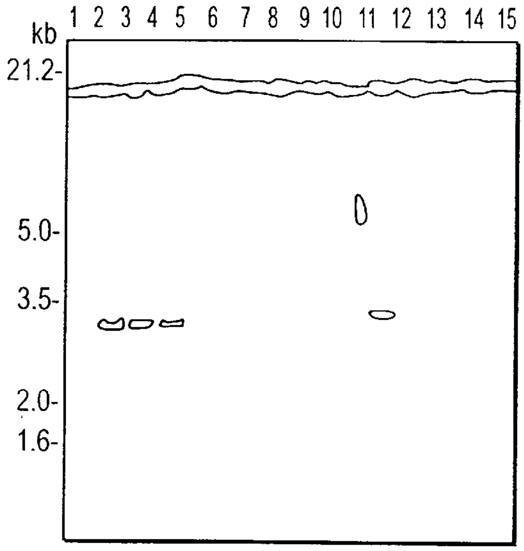
Figure 6D:
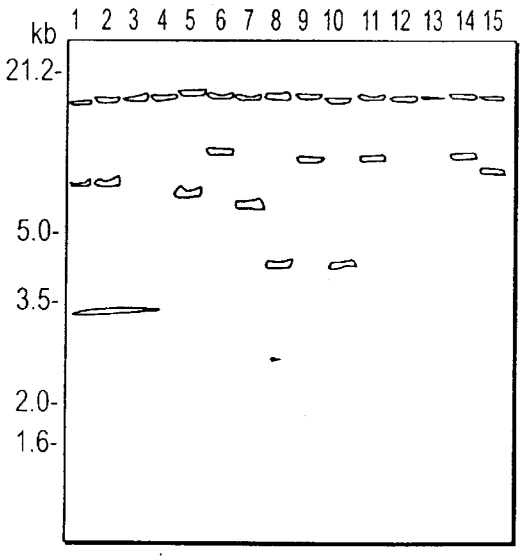

In Southern hybridization analysis, a DNA probe representing the encoding region of the ClfA SD-repeats hybridized to several genomic HindIII fragments in sixteen *S. epidermidis* strains (FIG. 6A). Three hybridizing fragments were observed in most strains, presumably representing the sdrF, sdrG, and sdrH genes. To confirm this and determine the frequency of the genes within these strains, additional analyses were performed with probes specific for DNA encoding each region A. The sdrH probe hybridized to fragments between 1.8–6.5 kb in all strains (FIG. 6B). The sdrG probe hybridized to a 16-kb fragment in all strains examined (FIG. 6C). In addition, the probe hybridized to HindIII fragments of 3.4 kb in four of the sixteen strains (KH11, K28, RP62a, and N910102). The same 3.4 kb fragments, however, did not hybridize with a probe specific for DNA encoding SD-repeats (FIG. 6A), suggesting the presence of a gene with similarity to the sdrG region A that lacks a SD-repeat region. FIG. 6D shows a Southern blot probed with both sdrG and sdrF region A DNA. The sdrF probe hybridized to HindIII-DNA fragments between 4.5 kb and 10 kb in twelve out of sixteen strains (strains K28, RP62a, N910173, and N910191 lacked a hybridizing band). These results suggest that the sdrF, sdrG, and sdrH genes are prevalent in *S. epidermidis* strains.

Expression of SdrF, SdrG, and SdrH in *S. epidermidis*.

Figure 7A:
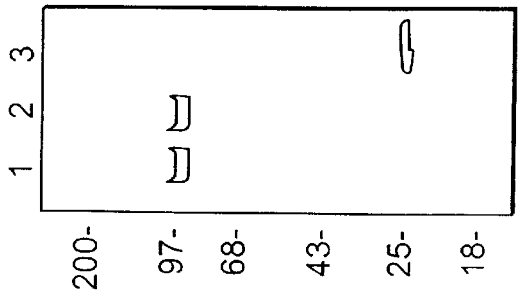
FIG. 7 shows the recombinant Sdr region A proteins and the specificity of their respective antisera as evidenced by: (A) Coomassie-stained SDS-PAGE of purified proteins used to raise rabbit polyclonal antisera. Lanes 1 and 2, histidine-tagged SdrFA and SdrGA, respectively; lane 3, GST-tagged SdrHA; (B) Left panel: Reactivity of pooled anti-SdrFA, -SdrGA, and -SdrHA antisera to *E. coli* lysates expressing GST-tagged SdrFA (lane 1), SdrGA (lane 2), and SdrHA (lane 3). Middle and right panels: Reactivity of anti-SdrFA and -SdrGA antisera, respectively, to the same proteins; and (C) Left panel: Reactivity of anti-histidine monoclonal antibody to *E. coli* lysates expressing histidine-tagged SdrFA (lane 1), SdrGA (lane 2) and full-length SdrH (lane 3). Right panel: Reactivity of anti-SdrHA antiserum to the same proteins. Kilodalton (kDa) size markers are shown at the left of panels A, B, and C.
Figure 7B:
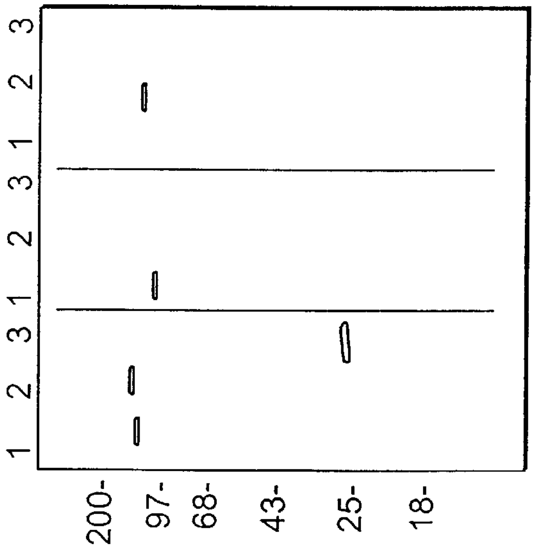
Figure 7C:
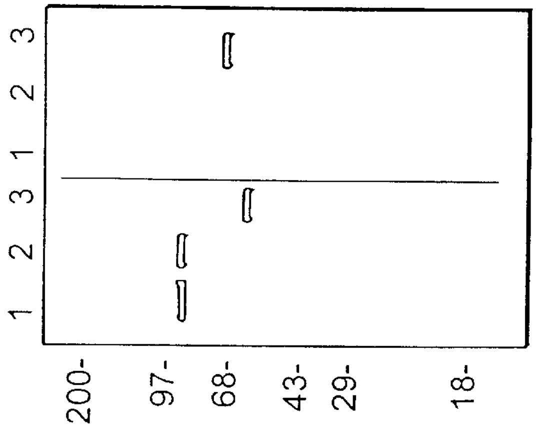

Immunologic methods were used to determine if SdrF, SdrG, and SdrH are expressed by *S. epidermidis*. Specific rabbit antisera were raised to recombinant fusion proteins representing different region As (designated SdrFA, SdrGA, and SdrHA). SdrFA and SdrGA were fused to polyhistidine ($His_n$), and SdrHA was fused to GST (FIG. 7A). Monospecificity of the antisera was confirmed against a panel of recombinant proteins containing different protein fusions. Specifically, antisera raised to $His_n$-SdrFA and -SdrGA did not, respectively, cross react with GST-SdrGA and -SdrFA (FIG. 7B). In addition, these same antisera did not cross react to GST-SdrHA (FIG. 7B). Antiserum raised to GST-SdrHA reacted to a full-length, $His_n$-SdrH protein but not to $His_n$-SdrFA or -SdrGA proteins (FIG. 7C).

Figure 8C:
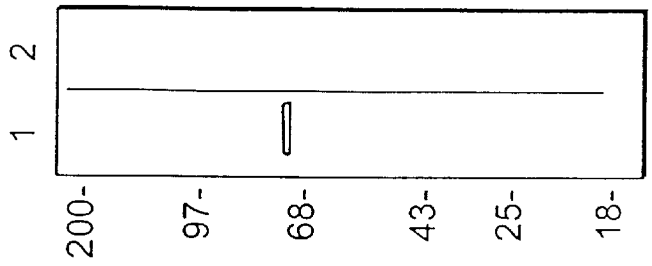
FIG. 8 depicts immunoblot analyses of Sdr protein expression in *S. epidermidis*, including: (A) Reactivity of anti-SdrFA antisera to a lysate of *S. epidermidis* 9491. Lane 1, immune antiserum; lane 2, preimmune antiserum; and lane 3, SdrFA-absorbed immune antiserum; (B) Reactivity of anti-SdrGA immune (lane 1), preimmune (lane 2), and SdrGA-absorbed immune (lane 3) antisera to a lysate of *S. epidermidis* strain K28; and (C) Reactivity of anti-SdrHA immune (lane 1) and SdrHA-absorbed immune (lane 2) antisera to a lysate of *S. epidermidis* 9491. kDa size markers are shown to the left of A, B, and C.
Figure 8B:
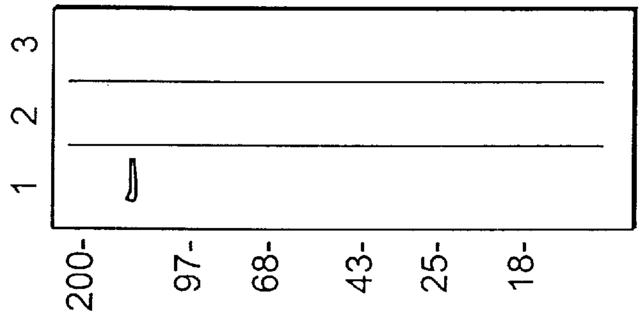
Figure 8A:
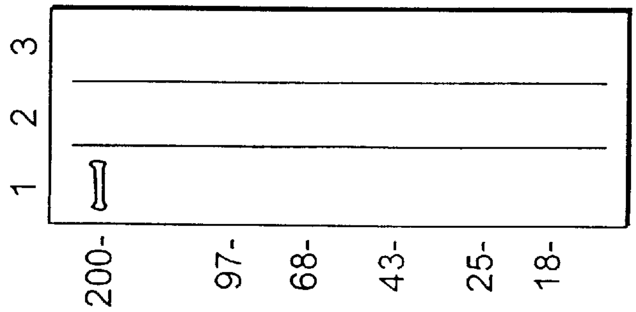

The region A-specific antisera were used to identify native SdrF, SdrG, and SdrH in lysates of their cognate *S. epidermidis* strains by Western immunoblotting. The anti-SdrFA antiserum reacted with a ca 230 kDa band from strain 9491 (FIG. 8A). This band was not present with Western blots reacted with preimmune antiserum or with anti-SdrFA antiserum that had been absorbed with *E. coli* lysates expressing a GST-SdrFA fusion protein (FIG. 8A). The anti-SdrGA antiserum reacted to a 170 kDa band in a lysate of *S. epidermidis* strain K28. This band was not present with preimmune antiserum or with anti-SdrGA antiserum that had been absorbed with an *E. coli* lysate expressing a GST-SdrGA fusion protein (FIG. 8B). Antiserum to SdrHA recognized a 75 kDa band in strain 9491, and this reactivity could be removed by absorbing the antiserum with recombinant SdrH present in an *E. coli* lysate (FIG. 8C). The apparent molecular masses of the anti-SdrFA, -SdrGA, and -SdrHA immunoreactive bands are larger than the masses predicted from the deduced amino acid sequences (179, 97, and 50 kDa, respectively). Decreased migration on SDS-PAGE has been previously noted for two *S. aureus* Sdr proteins, ClfA and ClfB, where up to a 50–100% increase in predicted mass was observed. The acidic nature of the Sdr proteins has been suggested to account for these observations.

Differences in Molecular Mass of SdrH in *S. epidermidis* Strains.

Figure 9A:
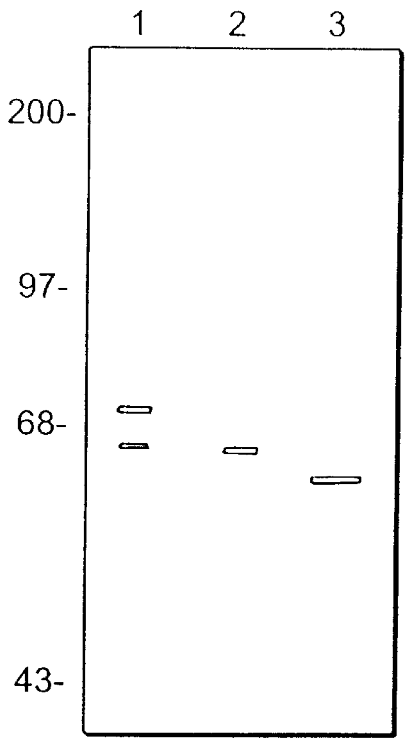
FIG. 9 shows the genetic analysis of SdrH protein size variation among *S. epidermidis* strains, including: (A) Reactivity of anti-SdrHA antiserum to different *S. epidermidis* strain lysates which reveal strain variations in the molecular mass of SdrH. Lane 1–3: Strains 9491, 8400, and KH11, respectively; and (B) PCR products representing DNA encoding the SdrH SD-repeat regions (lanes 1–3) or the region Cs (lanes 4–6) of the same strains. kDa and kb size markers are shown at the left of A and B, respectively.
Figure 9B:
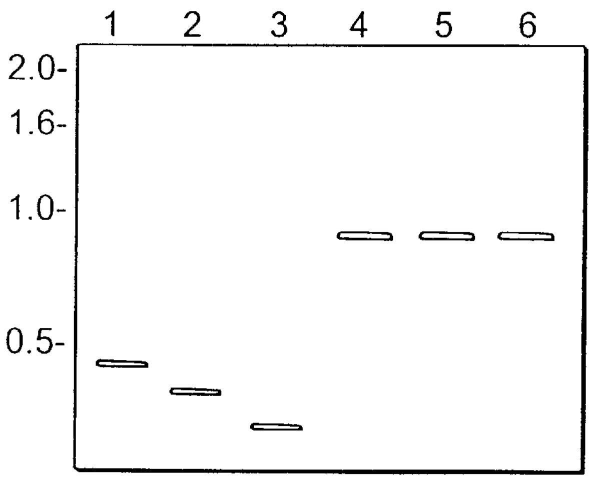

Western immnunoblot analysis, different strains of *S. epidermidis* possessed SdrH with apparent molecular masses that varied between 60 and 75 kDa (FIG. 9A). Variations in the molecular mass of ClfA has been previously correlated with the length of the SD-repeat region (15). PCR analysis of the sdrH genes from the *S. epidermidis* strains used above revealed that variations in the size of DNA encoding the SD-repeat regions correlated with the different masses of the SdrH proteins on Western blots. In contrast, PCR products of DNA encoding the region C of each SdrH were similar in size (FIG. 9B).

Analyses of SdrF, SdrG, and SdrH in Cell Wall Extracts and Protoplasts.

Figure 10C:
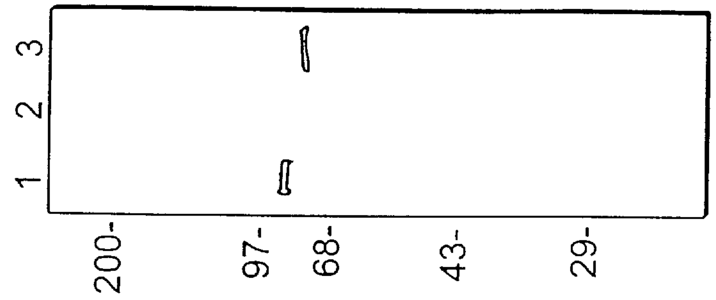
FIG. 10 represents analyses of Sdr proteins in cell-wall extracts and protoplasts, including: (A) Reactivity of anti-SdrFA antiserum to *S. epidermidis* strain 9491 lysates (lane 1), cell-wall extracts (lane 2), and purified protoplasts (lane 3); and (B) and (C) Reactivity of anti-SdrGA and -SdrHA antisera, respectively, to the same samples. KDa size markers are shown at the left of A, B, and C.
Figure 10B:
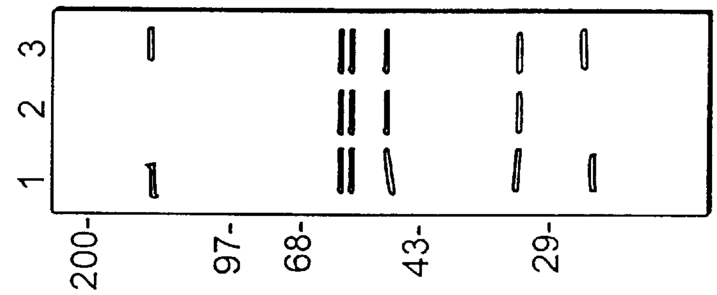
Figure 10A:
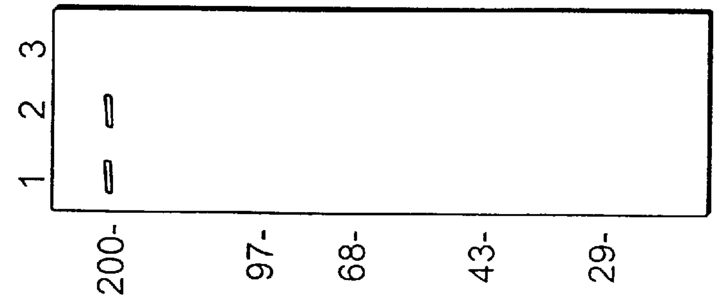

The presence of a LPXTG motif in both SdrF and SdrG suggests that these proteins are anchored in the cell wall and would therefore be present in cell-wall extracts of lysostaphin-treated *S. epidermidis*. Western blot analyses of early stationary phase, lysostaphin-digested *S. epidermidis* strain 9491 with anti-SdrFA antiserum revealed the presence of the 230 kDa SdrF band in both the whole-cell lysate and the cell-wall extract but not in the protoplast fraction (FIG. 10A). In contrast, analysis of the same samples with anti-SdrGA antiserum revealed the presence of SdrG (170 kDa) in the lysate and protoplast fraction but not in the cell-wall extract (FIG. 10B). Similar results were observed with blots containing lysostaphin-treated strain K28 (not shown). Further analysis of 9491 lysostaphin fractions with anti-SdrHA antiserum revealed an immunoreactive band in both the cell-wall lysate and protoplast fraction (FIG. 10C). These results suggest that, under these in vitro conditions, SdrF is localized and anchored to the cell wall, and that SdrG (despite its LPXTG motif) and SdrH are either associated with the cytoplasmic membrane or located inside the cell.

Reactivity of Convalescent Patient Antisera to SdrF, SdrG, and SdrH.

Figure 11:
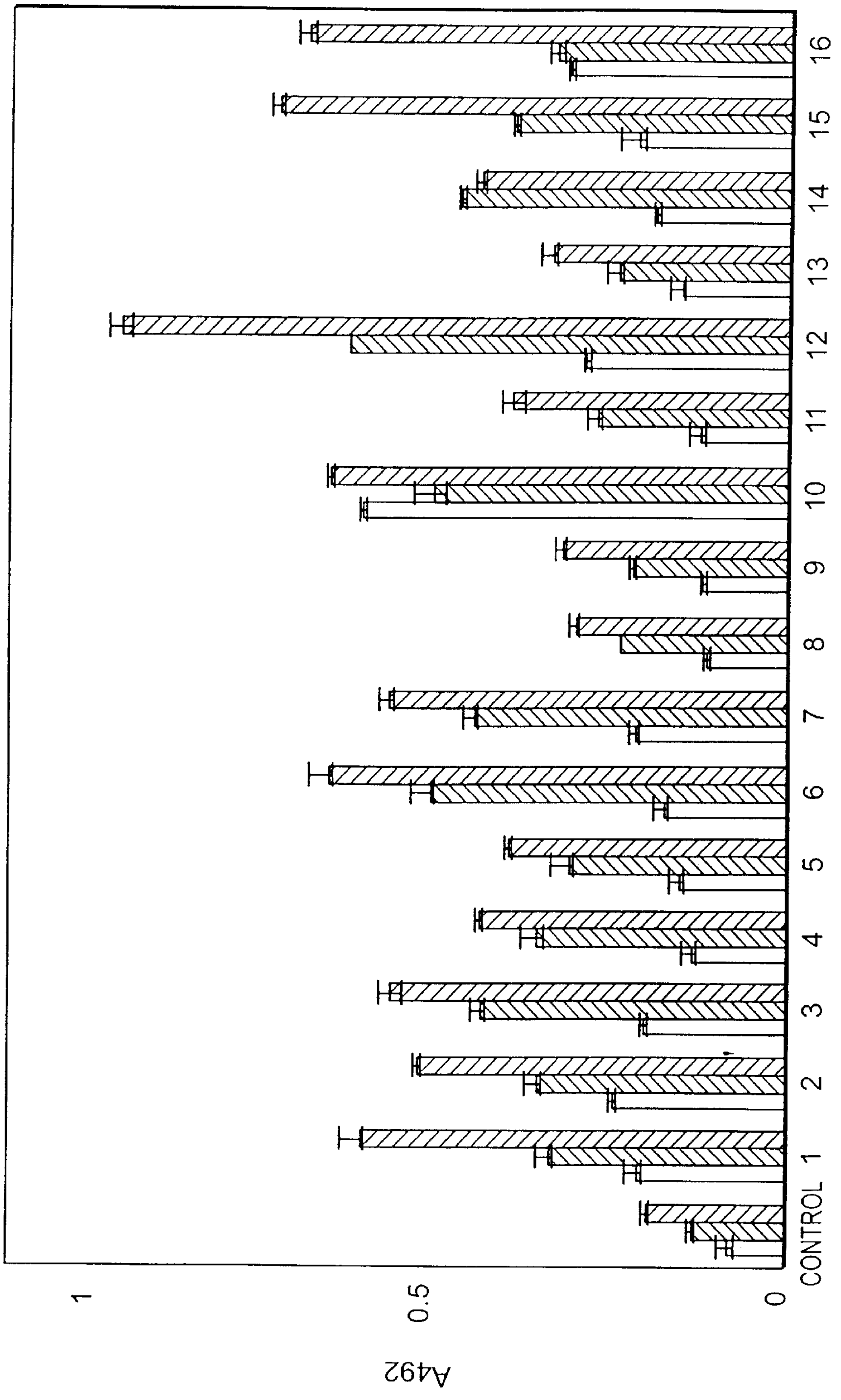
FIG. 11 shows the reactivity of IgG from patients convalescing from *S. epidermidis* infections to recombinant SdrFA (open bars), SdrGA (gray bars), and SdrHA (black bars) coated in an ELISA microtiter plate. Pooled IgG from two-year-old children was used as a comparative control. Error bars reflect standard deviations.

Recently, IgG from patients recovering from *S. aureus* infections has been shown to react with the fibronectin binding protein (FnbpA), suggesting that FnbpA is expressed by *S. aureus* during infection (1). Here, IgG purified from the antisera of fifteen patients recovering from various *S. epidermidis* infections was tested by ELISA for reactivity with the recombinant SdrF, SdrG, and SdrH region A proteins. FIG. 11 shows that IgG from patients' antisera had a higher titer to SdrFA, SdrGA, and SdrHA compared to that of IgG purified from pooled children antisera. The patients' IgG was often more reactive with SdrGA and SdrHA than with SdrFA. These results suggest that the Sdr proteins are expressed during *S. epidermidis* infection in humans.

Discussion

*S. epidermidis* infections in humans are associated with foreign-body devices that become rapidly coated with matrix proteins when introduced into the patient (26). Although mechanisms (encoded by the ica operon) have been proposed to mediate adherence and biofilm formation on uncoated polymer surfaces, specific factors mediating adherence to surfaces coated with host proteins have been poorly defined. The presence of Sdr proteins in *S. epidermidis* suggest that *S. epidermidis* may bind protein-coated matrix devices in a manner similar to *S. aureus* which utilizes ClfA and ClfB to mediate adherence to prosthetic devices coated with fibrinogen (21, 31). In this regard, a recombinant protein, expressed from cloned *S. epidermidis* DNA and similar to SdrG, has been shown to bind fibrinogen (22).

The *S. epidermidis* Sdr proteins may play a role in pathogenic processes apart from initial adherence. Experiments showing that proteolytic cleavage of the fibronectin-binding protein, Fnbp, from the surface of *S. aureus* produces a soluble, active protein, and this cleavage has been proposed to initiate release and dissemination of *S. aureus* from solid-phase fibronectin (18). Analogously, native SdrF and SdrG undergo rapid degradation in in vitro culture conditions in the absence of protease inhibitors (unpublished observations), and this proteolysis may provide a mechanism by which the bacteria can be detached from a substrate.

SdrF fractionates with cell-wall anchored proteins released by lysostaphin digestion, suggesting that it is present on the-cell surface. In contrast, SdrG, which contains an LPXTG, cell-wall sorting motif similar to SdrF, was found only in the protoplast fraction. The apparent lack of SdrG in the cell-wall fraction may be influenced by the bacterial growth phase or by proteolytic enzymes expressed during various growth phases. For instance, SdrG was found to be absent or diminished in lysates of strain K28 in early exponential phase. In addition, a number of *S. epidermidis* strains grown to late stationary phase did contain SdrG in the cell-wall extracts while other strains (including K28 and 9491) contained only potential degradation products of SdrG (unpublished results). Further studies are warranted to detail the regulation of SdrG anchorage to the cell wall and localization at the cell surface. Similarly, additional studies are required for SdrH, which contains features of cell-wall proteins but lacks a clear LPXTG motif.

As mentioned above, a protein similar to SdrG (designated Fbe) has been identified as a *S. epidermidis* protein capable of binding fibrinogen (22). Fbe was reported to have a region A directly adjacent to a SD-repeat region, but structures similar to region B repeats were not described. We have found that Fbe contains two region B repeats with 99% amino acids identity to the region B repeats of SdrG (unpublished results). In the reported sequence of Fbe, these repeats begin at amino acid 601 and end at the beginning of the SD-repeats. The original region A of Fbe was reported to contain a minimal fibrinogen-binding region between residues 269 . 599. With respect to the newly identified region B repeats, the minimal fibrinogen-binding region would be positioned at the extreme C terminus of region A. This is similar to ClfA which contains a minimal fibrinogen-binding region at its C terminus (McDevitt, 1995). The region As of Fbe and SdrG are 93% identical in amino acid sequence, and the predicted minimal-binding regions are 98% identical.

SdrH is unique among the eight described members of the Sdr protein family (from *S. aureus* and *S. epidermidis*) in that it possesses a divergent putative domain organization. The position of the SD-repeat region at the N terminus, a novel region C, and the lack of definitive cell-wall association sequences suggest that this protein functions differently than the known Sdr MSCRAMMs. Further studies on the bacterial localization and ligand-binding potential of SdrH are in progress.

The SD-repeat regions of SdrF and SdrG represent the longest and shortest SD repeats (558 and 56 residues, respectively) of the eight known Sdr proteins. Although the SD-repeats do not participate in fibrinogen binding, wild-type levels of functional ClfA expression were found to require a SD-repeat region with more than 40 residues (72 residues from the end of region A to the LPXTG motif) (4). This expanse of amino acids was postulated to span the cell wall and present a functional region A. Although SdrG contains 73 residues from the end of the region B repeats to the LPXTG motif, the two region B repeats may also affect the structure and function of the ligand-binding region A. The purpose of an extremely large SD-repeat region in SdrF is unknown. Given the interaction of the SD-repeat region with the cell wall, the differences in length of the SD-repeat regions between SdrF and SdrG may be associated with the localization differences observed in cell-wall fractions of these proteins. Variations in the length of SD-repeats in SdrH have been described. The SdrH protein from strain KH11 (the smallest SdrH observed) was found by DNA sequence analysis to contain 64 residues (unpublished results). The role of the SD repeats in SdrH is unknown but we speculate that this region, like other Sdr proteins, may be partially associated with the cell wall.

Genes encoding Sdr proteins of *S. epidermidis* are present in most of the clinical isolates examined to date. These strains were isolated from a broad range of disease outcomes in patients of diverse geographic locations. In addition, patients recovering from a variety of *S. epidermidis* infections have SdrF-, SdrG-, and SdrH-reactive IgG in their antisera. Similar traits have been observed for the five reported Sdr proteins of *S. aureus* [(8, 17) and unpublished results]. These studies suggest that the Sdr proteins are important constituents in *S. epidermidis* infectivity and growth. Interestingly, loci with homology to DNA encoding SD-repeat regions are also prevalent in strains of *S. haemolyticus, S. lugdunensis*, and *S. intermedius*, additional staphylococci capable of producing disease in humans and other mammals (unpublished results).

References Cited in Example 2

1. Casolini, F., L. Visai, D. Joh, P. G. Conaldi, A. Toniolo, M. Höök, and P. Speziale. 1998. Antibody response to fibronectin-binding adhesin FnbpA in patients with *Staphylococcus aureus* infections. Infect Immun. 66:5433–5442.
2. Fleer, A., and J. Verhoef. 1989. An evaluation of the role of surface hydrophobicity and extracellular slime in the pathogenesis of foreign-body-related infections due to coagulase-negative staphylococci. J Invest Surg. 2:391–6.
3. Foster, T. J., and M. Höök. 1998. Surface protein adhesins of *Staphylococcus aureus*. Trends Microbiol. 6:484–488.
4. Hartford, O., P. Francois, P. Vaudaux, and T. J. Foster. 1997. The dipeptide repeat region of the fibrinogen-binding protein (clumping factor) is required for functional expression of the fibrinogen-binding domain on the *Staphylococcus aureus* cell surface. Mol Microbiol. 25:1065–1076.
5. Heilmann, C., O. Schweitzer, C. Gerke, N. Vanittanakom, D. Mack, and F. Götz. 1996. Molecular basis of intercellular adhesion in the biofilm-forming *Staphylococcus epidermidis*. Mol Microbiol. 20:1083–1091.
6. Herrmann, M., P. E. Vaudaux, D. Pittet, R. Auckenthaler, P. D. Lew, F. Schumacher-Perdreau, G. Peters, and F. A. Waldvogel. 1988. Fibronectin, fibrinogen, and laminin act as mediators of adherence of clinical staphylococcal isolates to foreign material. J Infect Dis. 158:693–701.
7. Joh, H. J., K. House-Pompeo, J. M. Patti, S. Gurusiddappa, and M. Höök. 1994. Fibronectin receptors from Gram-positive bacteria: Comparison of active sites. Biochem. 33:6086–6092.
8. Josefsson, E., K. W. McCrea, D. Ni Eidhin, D. O'Connell, Cox. J., M. Höök, and T. J. Foster. 1998. Three new members of the serine-aspartate repeat protein multigene family of *Staphylococcus aureus*. Microbiology. 144:3387–3395.
9. Josefsson, E., D. O'Connell, T. J. Foster, I. Durussel, and J. A. Cox. 1998. The binding of calcium to the B-repeat segment of SdrD, a cell surface protein of *Staphylococcus aureus*. J Biol Chem. 273:31145–31152.
10. Kehoe, M. A. 1994. Cell-Wall-Associated Proteins in Gram-Positive Bacteria. In J. M. Ghuysen, and R. Hakenbeck (ed.), Bacterial Cell Wall. p.217–61.
11. Kloos, W. E., and T. L. Bannerman. 1994. Update on clinical significance of coagulase-negative staphylococci. Clin Microbiol Rev. 7:117–140.
12. Mack, D., M. Nedelmann, A. Krokotsch, A. Schwarzkopf, J. Heesemann, and R. Laufs. 1994. Characterization of transposon mutants of biofilm producing *Staphylococcus epidermidis* impaired in the accumulative phase of biofilm production: genetic identification of a hexosamine-containing polysaccharide intercellular adhesin. Infect Immun. 62:3244–3253.
13. Martin, M. A., M. A. Pfaller, R. M. Massanari, and R. P. Wenzel. 1989. Use of cellular hydrophobicity, slime production, and species identification markers for the clinical significance of coagulase-negative staphylococcal isolates. Am J Infect Control. 17:130–135.
14. McCrea, K. W., W. J. Watson, J. R. Gilsdorf, and C. F. Marrs. 1997. Identification of two minor subunits in the pilus of *Haemophilus influenzae*. J Bacteriol. 179:4227–4231.
15. McDevitt, D., and T. J. Foster. 1995. Variation in the size of the repeat region of the fibrinogen receptor (clumping factor) of *Staphylococcus aureus* strains. Microbiology. 141:937–43.
16. McDevitt, D., P. Francois, P. Vaudaux, and T. J. Foster. 1995. Identification of the ligand-binding domain of the surface-located fibrinogen receptor (clumping factor) of *Staphylococcus aureus*. Mol Microbiol. 16:895–907.

17. McDevitt, D., P. Francois, P. Vaudaux, and T. J. Foster. 1994. Molecular characterization of the clumping factor (fibrinogen receptor) of *Staphylococcus aureus*. Mol Microbiol. 11:237–248.
18. McGavin, M. J., C. Zahradka, K. Rice, and J. E. Scott. 1997. Modification of the *Staphylococcus aureus* fibronectin binding phenotype by V8 protease. Infect Immun. 65:2621–2628.
19. McKenney, D., J. Hubner, E. Muller, Y. Wang, D. A. Goldmann, and G. B. Pier. 1998. The ica locus of *Staphylococcus epidermidis* encodes production of the capsular polysaccharide/adhesin. Infect Immun. 66:4711–4720.
20. Moreillon, P., J. M. Entenza, P. Francioli, D. McDevitt, T. J. Foster, P. Francois, and P. Vaudaux. 1995. Role of *Staphylococcus aureus* coagulase and clumping factor in pathogenesis of experimental endocarditis. Infect Immun. 63:4738–4743.
21. Ni Eidhin, D., S. Perkins, P. Francois, P. Vaudaux, M. Höök, and T. J. Foster. 1998. Clumping factor B (ClfB), a new surface-located fibrinogen-binding adhesin of *Staphylococcus aureus*. Mol Microbiol. 30:245–257.
22. Nilsson, M., L. Frykberg, J. I. Flock, L. Pei, M. Lindberg, and B. Guss. 1998. A fibrinogen-binding protein of *Staphylococcus epidermidis*. Infect Immun. 66:2666–2673.
23. O'Connell, D. P., T. Nanavaty, D. McDevitt, S. Gurusiddappa, M. Höök, and T. J. Foster. 1998. The fibrinogen-binding MSCRAMM (clumping factor) of *Staphylococcus aureus* has a $Ca^{2+}$-dependent inhibitory site. J Biol Chem. 273:6821–6829.
24. Pascual, A., A. Fleer, N. A. Westerdaal, and J. Verhoef. 1986. Modulation of adherence of coagulase-negative staphylococci to Teflon catheters in vitro. Eur J Clin Microbiol. 5:518–22.
25. Paulsson, M., A. Ljungh, and T. Wadström. 1992. Rapid identification of fibronectin, vitronectin, laminin, and collagen cell surface binding proteins on coagulase-negative staphylococci by particle agglutination assays. J Clin Microbiol. 30:2006–2012.
26. Pitt, W. G., B. R. Young, K. Park, and S. L. Cooper. 1988. Plasma protein adsorption: in vitro and ex vivo observations. Macromol. Chem. Macromol. Symp. 17:435–465. (Abstract).
27. Rapley, R., and M. Walker. 1992. PCR screening of DNA cloned into polylinker-containing vectors with M13 sequencing primers. Biotechniques. 12:516.
28. Schägger, H., and G. von Jagow. 1987. Tricine-sodium dodecyl sulfate-polyacrylamide gel electrophoresis for the separation of proteins in the range from 1 to 100 kDa. Anal Biochem. 166:368–79.
29. Switalski, L. M., C. Ryden, K. Rubin, A. Ljungh, M. Höök, and T. Wadström. 1983. Binding of fibronectin to Staphylococcus strains. Infect Immun. 42:628–633.
30. Timmerman, C. P., A. Fleer, J. M. Besnier, L. De Graaf, F. Cremers, and J. Verhoef. 1991. Characterization of a proteinaceous adhesin of *Staphylococcus epidermidis* which mediates attachment to polystyrene. Infect Immun. 59:4187–4192.
31. Vaudaux, P. E., P. Francois, R. A. Proctor, D. McDevitt, T. J. Foster, R. M. Albrecht, D. P. Lew, H. Wabers, and S. L. Cooper. 1995. Use of adhesion-defective mutants of *Staphylococcus aureus* to define the role of specific plasma proteins in promoting bacterial adhesion to canine arteriovenous shunts. Infect Immun. 63:585–590.

What is claimed is:

1. An isolated nucleic acid molecule encoding a fibrinogen-binding protein, wherein the fibrinogen-binding protein is isolated from coagulase-negative *Staphylococcus epidermidis* and wherein the nucleic acid encodes SdrG and comprises SEQ ID NO:7.

2. The isolated nucleic acid molecule of claim 1, wherein the protein has an amino acid sequence comprising SEQ ID NO:10.

3. An isolated nucleic acid comprising a sequence that selectively hybridizes to the nucleic acid sequence of SEQ ID NO:7.

4. The isolated nucleic acid of claim 1 in a vector.

5. An isolated nucleic acid molecule encoding a fibrinogen-binding protein that is cell wall-associated, exhibits cation-dependent ligand-binding and has a highly conserved motif of which the consensus sequence is TYTFTDYVD (SEQ ID NO: 16), wherein the protein is isolated from coagulase-negative *Staphylococcus epidermidis* and wherein the nucleic acid encodes SdrG (SEQ ID NO: 10).

6. The isolated nucleic acid of claim 5, comprising the nucleic acid sequence of SEQ ID NO:7.

7. The isolated nucleic acid of claim 5 in a vector.

8. The isolated nucleic acid molecule of claim 1, wherein the nucleic acid encodes the ligand binding A region of SdrG.

9. The isolated nucleic acid molecule of claim 5, wherein the nucleic acid encodes the ligand binding A region of SdrG.

10. The isolated nucleic acid molecule of claim 1 comprising the nucleic acid sequence of nucleotides 102 to 2894 in SEQ ID NO:7.

* * * * *